United States Patent [19]

Diamond et al.

[11] 3,941,821

[45] Mar. 2, 1976

[54] 2-THIOSULFO BIPHENYLYLACETIC ACIDS

[75] Inventors: Julius Diamond, Lafayette Hill; Norman Julian Santora, Roslyn, both of Pa.

[73] Assignee: William H. Rorer, Inc., Fort Washington, Pa.

[22] Filed: Mar. 8, 1974

[21] Appl. No.: 449,548

Related U.S. Application Data

[60] Division of Ser. No. 152,366, June 11, 1971, Pat. No. 3,821,268, which is a continuation-in-part of Ser. No. 34,870, May 5, 1970.

[52] U.S. Cl.. 260/453 R; 260/290 HL; 260/293.62; 260/293.73; 260/295 AM; 260/295.5 A; 260/332.2 C
[51] Int. Cl.$^2$.................................... C07C 161/05

[58] Field of Search........................ 260/453 R, 516

[56]  References Cited
UNITED STATES PATENTS

| | | | |
|---|---|---|---|
| 2,934,552 | 4/1960 | Gaertner | 260/453 R |
| 3,624,142 | 11/1971 | Shen et al. | 260/516 |
| 3,786,085 | 1/1974 | Dickel et al. | 260/516 |

*Primary Examiner*—Glennon H. Hollrah
*Attorney, Agent, or Firm*—Erich M. H. Radde

[57]  ABSTRACT

Novel α-mercapto-p-biphenylylacetic acids and their derivatives have been prepared. Compounds of this invention possess useful anti-inflammatory, analgesic and antipyretic properties.

11 Claims, No Drawings

3,941,821

2-THIOSULFO BIPHENYLYLACETIC ACIDS

CROSS REFERENCES TO RELATED APPLICATIONS

This is a division, of application Ser. No. 152,366, filed June 11, 1971 now U.S. Pat. 3,821,268, which is a continuation-in-part application of Ser. No. 34,870, filed May 5, 1970.

SUMMARY OF THE INVENTION

This invention describes certain α-mercapto-p-biphenylylacetic acids and their derivatives and their use in therapeutic compositions. In addition, this invention relates to the preparation of these α-mercapto-p-biphenylylacetic acids. When the compounds of this invention are administered to mammals, they afford significant treatment of inflammation and associated pain and fever.

They further provide analgesic and antipyretic methods for the relief and treatment of pain and fever associated with inflammation.

BACKGROUND OF THE INVENTION

There has been continued efforts in research to develop drugs which would significantly inhibit the development of inflammation and relieve the pain and fever associated with it. Much of these efforts have been carried on in the field of steroids. While many of these compounds have been effective, they have had the drawback of causing many side effects.

We have unexpectedly found that α-mercapto-p-biphenylylacetic acid compounds and their derivatives have valuable pharmacologic properties.

We have found that α-mercapto-p-biphenylylacetic acid compounds and their derivatives possess useful anti-inflammatory, analgesic and antipyretic properties.

We have also found a series of anti-inflammatory compounds which are non-steroidal.

We have further found that these α-mercapto-p-biphenylylacetic acid compounds and their derivatives are novel.

We have also found that the compounds of this invention are useful in effectively providing a method for the inhibition of inflammation and the treatment of associated pain and fever.

We have still further found an entirely new class of anti-inflammatory, analgesic and antipyretic pharmaceutical compositions containing the α-mercapto-p-biphenylylacetic acids and derivatives of this invention as active ingredient.

We have again found a convenient method for synthesizing these compounds.

DESCRIPTION AND PREFERRED EMBODIMENT

This invention comprises a class of novel chemical compounds which contain a phenyl or substituted phenyl radical which is attached to a substituted phenyl or phenyl-α-mercaptoacetic acid in the para-position. This invention further comprises derivatives of said acetic acids and the method of preparing the same.

This invention also describes a new method of treating inflammation and associated pain and fever as well as novel therapeutic compositions.

The compounds of this invention can be represented by the generic structure which is described by the general formula I where:
$R_\alpha$ is hydrogen or loweralkyl;
$R'$ and $R$ are hydrogen or not more than one of R or R' at the same time is
  halo,
  nitro,
  amino,
  acylamino,
  mono- & diloweralkylamino,
  mercapto,
  acylthio,
  loweralkylthio,
  loweralkylsulfinyl,
  loweralkylsulfonyl,
  hydroxy,
  loweralkoxy,
  acyloxy,
  haloloweralkyl,
  cyano,
  acetyl or
  loweralkyl;
X is
  mercapto,
  acylthio,
  carboxyacylthio,
  aroylthio,
  carboxyaroylthio,
  loweralkoxythiocarbonylthio,
  loweralkoxycarbonylthio,
  arloweralkoxycarbonylthio,
  amidinothio,
  thiocyanato,
  thiosulfo,
  thioacylthio,
  diloweralkylthiocarbamylthio,
  carbamylthio,
  loweralkylcarbamylthio,
  diloweralkylcarbamylthio,
  loweralkylthio,
  loweralkylsulfinyl,
  lower alkylsulfonyl,
  sulfino or
  sulfo; and
Z is
  —OH,
  loweralkoxy,
  arloweralkoxy,
  —NH₂,
  loweralkylamino,
  diloweralkylamino,
  cycloloweralkylamino,
  —N͡A
  (where A is loweralkylidenyl or heteroloweralkylidenyl),
  —NHOH,
  —NHNH₂ or
  —OM (where M is an alkali, alkaline earth or aluminum metal or an ammonium salt).

The compounds of this invention contain an asymmetric carbon atom in the alpha-position of the acetic acid side chain. As a result, the above compounds of formula I may be obtained as racemic mixtures of their dextro (+) and levorotatory (−) isomers. It is to be understood that said *d* and *l* isomers as well as the dl mixtures thereof are embraced within the scope of this invention.

More specifically, the chemical compounds of this invention which have particular usefulness as anti-inflammatory, analgesic and antipyretic agents are described by formulae II–IV

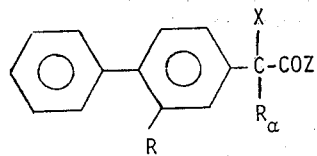

II

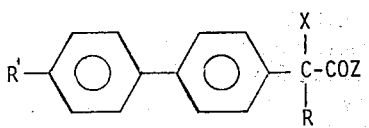

III

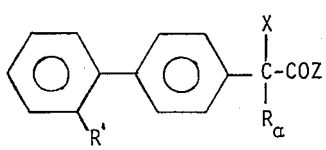

IV where:
R, R', $R_\alpha$, X and Z are as described above.

Those compounds whose properties are even more preferred are described by formula IV where:
$R_\alpha$ is hydrogen or loweralkyl;
R' is
　halo,
　nitro,
　loweralkylsulfonyl,
　haloloweralkyl or
　cyano;
X is
　mercapto,
　acylthio,
　aroylthio,
　loweralkoxythiocarbonylthio,
　loweralkoxycarbonylthio,
　amidinothio,
　thiocyanato,
　thiosulfo,
　carbamylthio,
　loweralkylcarbamylthio,
　diloweralkylcarbamylthio,
　loweralkylthio,
　loweralkylsulfinyl,
　loweralkylsulfonyl,
　sulfino or
　sulfo; and
Z is
　—OH,
　loweralkoxy,
　arloweralkoxy,
　—NH₂,
　loweralkylamino or
　—OM.

A special embodiment of this invention which describes novel compounds that are effective in inhibiting inflammation and the treatment of pain and fever associated with inflammation as well as having analgesic and antipyretic effectiveness for the relief and treatment of pain and fever not symptomatically related to an inflammation indication are described by formula V

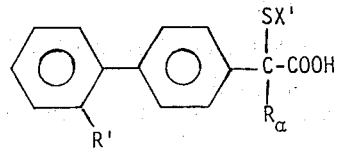

V where:
$R_\alpha$ is
　hydrogen,
　methyl or ethyl;
R' is
　chloro,
　bromo,
　nitro,
　methylsulfonyl,
　trifluoromethyl or
　cyano;
X' is
　hydrogen,
　acyl,
　aroyl,
　loweralkoxythiocarbonyl,
　loweralkoxycarbonyl,
　sulfo,
　carbamyl,
　loweralkylcarbamyl,
　diloweralkylcarbamyl; and
the salts thereof.

Included within the scope of this further special embodiment are the racemic mixtures as well as the dextro and levorotatory isomers thereof.

In the descriptive portions of this invention, the following definitions apply:

The term "loweralkyl" refers to a loweralkyl hydrocarbon group containing from 1 to about 6 carbon atoms which may be straight chained or branched.

The "acyl" radical may be any organic radical derived from an organic acid by the removal of its hydroxyl group such as formyl, acetyl, propionyl, 3-carboxypropionyl, 3-carboxy-2-propenoyl, camphoryl, benzoyl, toluoyl or heteroyl such as pyridinoyl, piperidinoyl, thenoyl, etc.

"Loweralkoxy" signifies an alkoxy group containing from 1 to about 6 carbon atoms which may be straight chained or branched.

The preferred "aroyl" is benzoyl, loweralkylbenzoyl such as toluoyl or halobenzoyl such as p-chlorobenzoyl, 2-carboxybenzoyl, etc.

The term "loweralkylidenyl" refers to a loweralkylidenyl hydrocarbon group containing from 2 to about 6 carbon atoms.

"Heteroloweralkylidenyl" refers to a loweralkylidenyl hydrocarbon group containing from about 2 to 5 carbon atoms and having one or more hetero atoms in the chain selected from O, N or S, such as piperidinyl, morpholinyl, etc.

The preferred "alkali" or "alkaline earth" metals are sodium, potassium, calcium and magnesium.

The term "ammonium salt" refers to the cation formed when ammonia or an organic amine react with the carboxyl group to form ammonium salts of the structure given in the formula. The ammonium salts are formed with a (1) loweralkylamines such as methylamine, diethylamine, triethylamine; (2) hydroxyloweralkylamines such as β-hydroxyethylamine; (3) heterocyclic amines such as 2-aminopyridine, piperazine, piperidine; (4) aralkylamines such as α-methylbenzylamine, phenethylamine; (5) cycloalkylamines such as cyclohexylamine; (6) alkaloids such as quinine, cinchonidine, cinchonine, ephedrine.

Representative compounds of this invention which are particularly useful are as follows:

α-mercapto-3-chloro-4-biphenylylacetic acid
α-acetylthio-3-chloro-4-biphenylylacetic acid
α-propionylthio-3-chloro-4-biphenylylacetic acid
α-butyrylthio-3-chloro-4-biphenylylacetic acid
α-butenoylthio-3-chloro-4-biphenylylacetic acid
α-benzoylthio-3-chloro-4-biphenylylacetic acid
α-(σ-toluoylthio)-3-chloro-4-biphenylylacetic acid
α-(σ-carboxybenzoylthio)-3-chloro-4-biphenylylacetic acid
α-methoxythiocarbonylthio-3-chloro-4-biphenylylacetic acid
α-ethoxythiocarbonylthio-3-chloro-4-biphenylylacetic acid
α-methoxycarbonylthio-3-chloro-4-biphenylylacetic acid
α-ethoxycarbonylthio-3-chloro-4-biphenylylacetic acid
α-benzyloxycarbonylthio-3-chloro-4-biphenylylacetic acid
α-thioformylthio-3-chloro-4-biphenylylacetic acid
α-amidinothio-3-chloro-4-biphenylylacetic acid
α-thiocyanato-3-chloro-4-biphenylylacetic acid
α-thiosulfo-3-chloro-4-biphenylylacetic acid
α-carbamylthio-3-chloro-4-biphenylylacetic acid
α-ethylcarbamylthio-3-chloro-4-biphenylylacetic acid
α-dimethylcarbamylthio-3-chloro-4-biphenylylacetic acid
α-diethylcarbamylthio-3-chloro-4-biphenylylacetic acid
α-methylthio-3-chloro-4-biphenylylacetic acid
α-ethylthio-3-chloro-4-biphenylylacetic acid
α-propylthio-3-chloro-4-biphenylylacetic acid
α-i-propylthio-3-chloro-4-biphenylylacetic acid
α-methylsulfinyl-3-chloro-4-biphenylylacetic acid
α-methylsulfonyl-3-chloro-4-biphenylylacetic acid
α-sulfino-3-chloro-4-biphenylylacetic acid
α-sulfo-3-chloro-4-biphenylylacetic acid
α-mercapto-4'-chloro-4-biphenylylacetic acid
α-acetylthio-4'-chloro-4-biphenylylacetic acid
α-propionylthio-4'-chloro-4-biphenylylacetic acid
α-butyrylthio-4'-chloro-4-biphenylylacetic acid
α-butenoylthio-4'-chloro-4-biphenylylacetic acid
α-benzoylthio-4'-chloro-4-biphenylylacetic acid
α(τ-toluoylthio)-4'-chloro-4-biphenylylacetic acid
α-(τ-carboxybenzoylthio)-4'-chloro-4-biphenylylacetic acid
α-methoxythiocarbonylthio-4'-chloro-4-biphenylylacetic acid
α-ethoxythiocarbonylthio-4'-chloro-4-biphenylylacetic acid
α-methoxycarbonylthio-4'-chloro-4-biphenylylacetic acid
α-ethoxycarbonylthio-4'-chloro-4-biphenylylacetic acid
α-benzyloxycarbonylthio-4'-chloro-4-biphenylylacetic acid
α-thioformylthio-4'-chloro-4-biphenylylacetic acid
α-amidinothio-4'-chloro-4-biphenylylacetic acid
α-thiocyanato-4'-chloro-4-biphenylylacetic acid
α-thiosulfo-4'-chloro-4-biphenylylacetic acid
α-carbamylthio-4'-chloro-4-biphenylylacetic acid
α-ethylcarbamylthio-4'-chloro-4-biphenylylacetic acid
α-dimethylcarbamylthio-4'-chloro-4-biphenylylacetic acid
α-diethylcarbamylthio-4'-chloro-4-biphenylylacetic acid
α-methylthio-4'-chloro-4-biphenylylacetic acid
α-ethylthio-4'-chloro-4-biphenylylacetic acid
α-propylthio-4'-chloro-4-biphenylylacetic acid
α-i-propylthio-4'-chloro-4-biphenylylacetic acid
α-methylsulfinyl-4'-chloro-4-biphenylylacetic acid
α-methylsulfonyl-4'-chloro-4-biphenylylacetic acid
α-sulfino-4'-chloro-4-biphenylylacetic acid
α-sulfo-4'-chloro-4-biphenylylacetic acid
α-mercapto-2'-chloro-4-biphenylylacetic acid
α-acetylthio-2'-chloro-4-biphenylylacetic acid
α-propionylthio-b 2'-chloro-4-biphenylylacetic acid
α-butyrylthio-2'-chloro-4-biphenylylacetic acid
α-butenoylthio-2'-chloro-4-biphenylylacetic acid
α-benzoylthio-2'-chloro-4-biphenylylacetic acid
α-(τ-toluoylthio)-2'-chloro-4-biphenylylacetic acid
α-(τ-carboxybenzoylthio)-2'-chloro-4-biphenylylacetic acid
α-methoxythiocarbonylthio-2'-chloro-4-biphenylylacetic acid
α-ethoxythiocarbonylthio-2'-chloro-4-biphenylylacetic acid
α-methoxycarbonylthio-2'-chloro-4-biphenylylacetic acid
α-ethoxycarbonylthio-2'-chloro-4-biphenylylacetic acid
α-benzyloxycarbonylthio-2'-chloro-4-biphenylylacetic acid
α-thioformylthio-2'-chloro-4-biphenylylacetic acid
α-amidinothio-2'-chloro-4-biphenylylacetic acid
α-thiocyanato-2'-chloro-4-biphenylylacetic acid
α-thiosulfo-2'-chloro-4-biphenylylacetic acid
α-carbamylthio12'-chloro-4-biphenylylacetic acid
α-ethylcarbamylthio-2'-chloro-4-biphenylylacetic acid
α-dimethylcarbamylthio-2'-chloro-4-biphenylylacetic acid
α-diethylcarbamylthio-2'-chloro-4-biphenylylacetic acid
α-methylthio-2'-chloro-4-biphenylylacetic acid
α-ethylthio-2'-chloro-4-biphenylylacetic acid
α-propylthio-2'-chloro-4-biphenylylacetic acid
α-i-propylthio-2'-chloro-4-biphenylylacetic acid
α-methylsulfinyl-2'-chloro-4-biphenylylacetic acid
α-methylsulfonyl-2'-chloro-4-biphenylylacetic acid
α-sulfino-2'-chloro-4-biphenylacetic acid
α-sulfo-2'-chloro-4-biphenylylacetic acid
α-acetylthio-2'-fluoro-4-biphenylylacetic acid
α-acetylthio-2'-bromo-4-biphenylylacetic acid
α-acetylthio-2'-iodo-4-biphenylylacetic acid
α-acetylthio-2'-nitro-4-biphenylylacetic acid
α-acetylthio-2'-trifluoromethyl-4-biphenylylacetic acid
α-acetylthio-2'-mercapto-4-biphenylylacetic acid α-acetylthio-2'-acetylthio-4-biphenylylacetic acid
α-acetylthio-2'-methylmercapto-4-biphenylylacetic acid
α-acetylthio-2'-methylsulfinyl-4-biphenylylacetic acid
α-acetylthio-2'-methylsulfonyl-4-biphenylylacetic acid
α-acetylthio-2'-cyano-4-biphenylylacetic acid
α-acetylthio-2'-carboxy-4-biphenylylacetic acid
α-acetylthio-2'-carbethoxy-4-biphenylylacetic acid
α-acetylthio-2'-amino-4-biphenylylacetic acid
α-acetylthio-2'-acetylamino-4-biphenylylacetic acid
α-acetylthio-2'-methylamino-4-biphenylylacetic acid
α-acetylthio-2'-dimethylamino-4-biphenylylacetic acid
α-acetylthio-2'-hydroxy-4-biphenylylacetic acid
α-acetylthio-2'-acetyloxy-4-biphenylacetic acid
α-acetylthio-2'-methoxy-4-biphenylylacetic acid
α-acetylthio-2'-acetoxy-4-biphenylylacetic acid
α-acetylthio-2'-methyl-4-biphenylylacetic acid
α-mercapto-2'-fluoro-4-biphenylylacetic acid
α-propionylthio-2'-bromo-4-biphenylylacetic acid
α-butyrylthio-2'-nitro-4-biphenylylacetic acid
α-butenoylthio-2'-trifluoromethyl-4-biphenylylacetic acid
α-benzoylthio-2'-cyano-4-biphenylylacetic acid
α,2'-dimethylsulfonyl-4-biphenylylacetic acid
α-benzoylthio-2'-fluoro-4-biphenylylacetic acid
α-benzoylthio-2'-bromo-4-biphenylylacetic acid
α-sulfino-2'-nitro-4-biphenylylacetic acid
α-sulfo-2'-trifluoromethyl-4-biphenylylacetic acid
α-amidinothio-2'-cyano-4-biphenylylacetic acid
methyl α-acetylthio-2'-chloro-4-biphenylylacetic acid
ethyl α-acetylthio-2'-chloro-4-biphenylylacetic acid
benzyl α-acetylthio-2'-chloro-4-biphenylylacetic acid
N-methyl α-acetylthio-2'-chloro-4-biphenylylacetic acid
N,N-dimethyl α-acetylthio-2'-chloro-4-biphenylylacetic acid
N,N-diethyl α-acetylthio-2'-chloro-4-biphenylylacetic acid
N,N-ethylmethyl α-acetylthio-2'-chloro-4-biphenylylacetic acid
N-isopropyl α-acetylthio-2'-chloro-4-biphenylylacetic acid
N-cyclopropyl α-acetylthio-2'-chloro-4-biphenylylacetic acid
N,N-pentamethylene α-acetylthio-2'-chloro-4-biphenylylacetic acid
N,N-oxydiethylene α-acetylthio-2'-chloro-4-biphenylylacetic acid
N,N-methylaminoethylenetrimethylene α-acetylthio-2'-chloro-4-biphenylylacetic acid
N,N-thiotrimethylene α-acetylthio-2'-chloro-4-biphenylylacetic acid
α-acetylthio-2'-chloro-4-biphenylylacetic acid, sodium salt
α-acetylthio-2'-chloro-4-biphenylylacetic acid, potassium salt
α-acetylthio-2'-chloro-4-biphenylylacetic acid, calcium salt
α-acetylthio-2'-chloro-4-biphenylylacetic acid, aluminum salt
α-acetylthio-2'-chloro-4-biphenylylacetic acid, dimethylammonium salt
α-acetylthio-2'-chloro-4-biphenylylacetic acid, diethylammonium salt
α-acetylthio-2'-chloro-4-biphenylylacetic acid, β-hydroxyethylammonium salt
α-acetylthio-2'-chloro-4-biphenylylacetic acid, piperazinium salt
α-acetylthio-2'-chloro-4-biphenylylacetic acid, piperidinium salt
α-acetylthio-2'-chloro-4-biphenylylacetic acid, methylbenzylammonium salt
α-mercapto-α-methyl-2'-chloro-4-biphenylylacetic acid
α-acetylthio-α-methyl-2'-chloro-4-biphenylylacetic acid
α-propionylthio-α-methyl-2'-chloro-4-biphenylylacetic acid
α-butyrylthio-α-methyl-2'-chloro-4-biphenylylacetic acid
α-butenoylthio-α-methyl-2'-chloro-4-biphenylylacetic acid
α-benzylthio-α-methyl-2'-chloro-4-biphenylylacetic acid
α-methoxythiocarbonylthio-α-methyl-2'-chloro-4-biphenylylacetic acid
α-methoxycarbonylthio-α-methyl-2'-chloro-4-biphenylylacetic acid
α-benzyloxycarbonylthio-α-methyl-2'-chloro-4-biphenylylacetic acid
α-thioformylthio-α-methyl-2'-chloro-4-biphenylylacetic acid
α-amidinothio-α-methyl-2'-chloro-4-biphenylylacetic acid
α-thiocyanato-α-methyl-2'-chloro-4-biphenylylacetic acid
α-thiosulfo-α-methyl-2'-chloro-4-biphenylylacetic acid
α-carbamylthio-α-methyl-2'-chloro-4-biphenylylacetic acid
α-diethylcarbamylthio-α-methyl-2'-chloro-4-biphenylylacetic acid
α-ethylthio-α-methyl-2'-chloro-4-biphenylylacetic acid
α-methylsulfinyl-α-methyl-2'-chloro-4-biphenylylacetic acid
α-methylsulfonyl-α-methyl-2'-chloro-4-biphenylylacetic acid
α-sulfino-α-methyl-2'-chloro-4-biphenylylacetic acid
α-sulfo-α-methyl-2'-chloro-4-biphenylylacetic acid
α-acetylthio-α-ethyl-2'-chloro-4-biphenylylacetic acid
α-acetylthio-α-propyl-2'-chloro-4-biphenylylacetic acid
α-acetylthio-α-methyl-2'-fluoro-4-biphenylylacetic acid
α-acetylthio-α-methyl-2'-bromo-4-biphenylylacetic acid
α-acetylthio-α-methyl-2'-nitro-4-biphenylylacetic acid
α-acetylthio-α-methyl-2'-trifluoromethyl-4-biphenylylacetic acid
α-acetylthio-α-methyl-2'-cyano-4-biphenylylacetic acid
α-acetylthio-α-methyl-2'-methylsulfonyl-4-biphenylylacetic acid
α-acetylthio-α-methyl-3-chloro-4-biphenylylacetic acid
α-propionylthio-α-methyl-3-chloro-4-biphenylylacetic acid α-methoxythiocarbonylthio-α-methyl-3-chloro-4-biphenylylacetic acid
α-methoxycarbonylthio-α-methyl-3-chloro-4-biphenylylacetic acid
α-diethylcarbamylthio-α-methyl-3-chloro-4-biphenylylacetic acid
α-methylsulfonyl-α-methyl-3-chloro-4-biphenylylacetic acid
α-acetylthio-α-ethyl-3-chloro-4-biphenylylacetic acid
α-acetylthio-α-propyl-3-chloro-4-biphenylylacetic acid
α-acetylthio-α-methyl-3-fluoro-4-biphenylylacetic acid
α-acetylthio-α-methyl-3-bromo-4-biphenylylacetic acid
α-acetylthio-α-methyl-3-nitro-4-biphenylylacetic acid
α-acetylthio-α-methyl-3-trifluoromethyl-4-biphenylylacetic acid
α-acetylthio-α-methyl-3-cyano-4-biphenylylacetic acid
α-acetylthio-α-methyl-3-methylsulfonyl-4-biphenylylacetic acid
α-acetylthio-α-methyl-4'-chloro-4-biphenylylacetic acid
α-propionylthio-α-methyl-4'-chloro-4-biphenylylacetic acid
α-methoxythiocarbonylthio-α-methyl-4'-chloro-4-biphenylylacetic acid
α-methoxycarbonylthio-α-methyl-4'-chloro-4-biphenylylacetic acid
α-thioformylthio-α-methyl-4'-chloro-4-biphenylylacetic acid
α-diethylcarbamylthio-α-methyl-4'-chloro-4-biphenylylacetic acid
α-methylsulfonyl-α-methyl-4'-chloro-4-biphenylylacetic acid
α-acetylthio-α-ethyl-4'-chloro-4-biphenylylacetic acid
α-acetylthio-α-propyl-4'-chloro-4-biphenylylacetic acid
α-acetylthio-α-methyl-4'-fluoro-4-biphenylylacetic acid
α-acetylthio-α-methyl-4'-bromo-4-biphenylylacetic acid
α-acetylthio-α-methyl-4'-nitro-4-biphenylylacetic acid
α-acetylthio-α-methyl-4'-trifluoromethyl-4-biphenylylacetic acid
α-acetylthio-α-methyl-4'-cyano-4-biphenylylacetic acid
α-acetylthio-α-methyl-4'-methylsulfonyl-4-biphenylylacetic acid
d α-acetylthio-2'-fluoro-4-biphenylylacetic acid
l α-acetyltio-2'-fluoro-4-biphenylylacetic acid
d α-acetylthio-2'-chloro-4-biphenylylacetic acid
l α-acetylthio-2'-chloro-4-biphenylylacetic acid
d α-acetylthio-2'-bromo-4-biphenylylacetic acid
l α-acetylthio-2'-bromo-4-biphenylylacetic acid
d α-acetylthio-2'-nitro-4-biphenylylacetic acid
l α-acetylthio-2'-nitro-4-biphenylylacetic acid
d α-acetylthio-2'-trifluoromethyl-4-biphenylylacetic acid
l α-acetylthio-2'-trifluoromethyl-4-biphenylylacetic acid
d α-acetylthio-2'-cyano-4-biphenylylacetic acid
l α-acetylthio-2'-cyano-4-biphenylylacetic acid
d α-acetylthio-3'-methylsulfonyl-4-biphenylylacetic acid
l α-acetylthio-3'-methylsulfonyl-4-biphenylylacetic acid
d α-acetylthio-3-chloro-4-biphenylylacetic acid
l α-acetylthio-3-chloro-4-biphenylylacetic acid
d α-acetylthio-4'-chloro-4-biphenylylacetic acid
l α-acetylthio-4'-chloro-4-biphenylylacetic acid
d α-acetylthio-α-methyl-2'-chloro-4-biphenylylacetic acid
l α-acetylthio-α-methyl-2'-chloro-4-biphenylylacetic acid
d α-acetylthio-α-methyl-4'-chloro-4-biphenylylacetic acid
l α-acetylthio-α-methyl-4'-chloro-4-biphenylylacetic acid
d α-acetylthio-α-methyl-3-chloro-4-biphenylylacetic acid
l α-acetylthio-α-methyl-3-chloro-4-biphenylylacetic acid
d α-mercapto-2'-chloro-4-biphenylylacetic acid
l α-mercapto-2'-chloro-4-biphenylylacetic acid
d α-butyrylthio-2'-nitro-4-biphenylylacetic acid
l α-butyrylthio-2'-nitro-4-biphenylylacetic acid
d α-diethylcarbamylthio-2'-chloro-4-biphenylylacetic acid
l α-diethylcarbamylthio-2'-chloro-4-biphenylylacetic acid
d α-i-propylthio-2'-chloro-4-biphenylylacetic acid
l α-i-propylthio-2'-chloro-4-biphenylylacetic acid
d α-propionylthio-2'-chloro-4-biphenylylacetic acid
l α-propionylthio-2'-chloro-4-biphenylylacetic acid
d α-sulfino-2'-chloro-4-cyclohexylphenylacetic acid
l α-sulfino-2'-chloro-4-cyclohexylphenylacetic acid
d α-methylsulfinyl-2'-chloro-4-biphenylylacetic acid
l α-methylsulfinyl-2'-chloro-4-biphenylylacetic acid
d α-(τ-carboxybenzoylthio)-2'-chloro-4-biphenylylacetic acid
l α-(τ-carboxybenzoylthio)-2'-chloro-4-biphenylylacetic acid
d methyl α-acetylthio-2'-chloro-4-biphenylylacetic acid
l methyl α-acetylthio-2'-chloro-4-biphenylylacetic acid
d benzyl α-acetylthio-2'-chloro-4-biphenylylacetic acid
l benzyl α-acetylthio-2'-chloro-4-biphenylylacetic acid
d N-methyl α-acetylthio-2'-chloro-4-biphenylylacetic acid
l N-methyl α-acetylthio-2'-chloro-4-biphenylylacetic acid
d N,N-diethyl α-acetylthio-2'-chloro-4-biphenylylacetic acid
l N,N-diethyl α-acetylthio-2'-chloro-4-biphenylylacetic acid
d N,N-pentamethylene α-acetylthio-2'-chloro-4-biphenylylacetic acid
l N,N-pentamethylene α-acetylthio-2'-chloro-4-biphenylylacetic acid
d N,N-oxydiethylene α-acetylthio-2'-chloro-4-biphenylylacetic acid
l N,N-oxydiethylene α-acetylthio-2'-chloro-4-biphenylylacetic acid
d α-acetylthio-2'-chloro-4-biphenylylacetic acid, sodium salt
l α-acetylthio-2'-chloro-4-biphenylylacetic acid, sodium salt d α-acetylthio-2'-chloro-4-biphenylylacetic acid, diethylammonium salt l α-acetylthio-2'-chloro-4-biphenylylacetic acid, diethylammonium salt d α-acetylthio-2'-chloro-4-biphenylylacetic acid, piperazinium salt l α-acetylthio-2'-chloro-4-biphenylylacetic acid, piperazinium salt The compounds of this invention may be prepared by the following general procedures.

Condensation of a biphenyl compound with a loweralkyl or aralkyl oxalyl chloride in the presence of anhydrous aluminum chloride results in a biphenylylglyoxylate. This may then be reacted with an alkyl Grignard reagent to form the α-alkylbiphenylylglycolate or it may be reduced to the biphenylylglycolate by catalytic hydrogenation with platinum oxide or under sodium borohydride conditions. It is convenient to start with a substituted biphenyl compound and in this manner the resultant product would be the corresponding substituted α-alkylbiphenylylglycolate or the biphenylylglycolate.

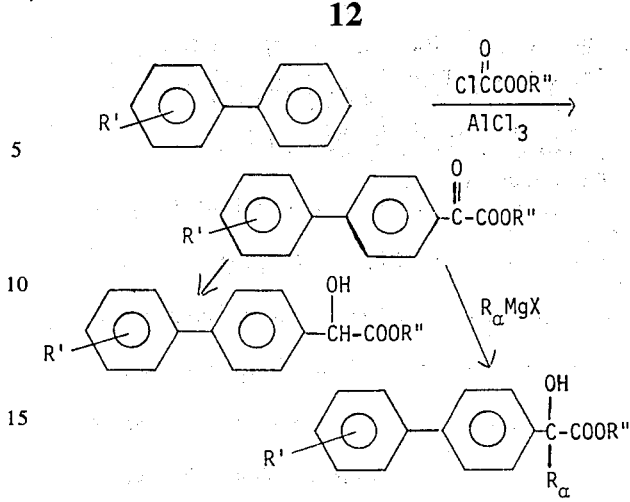

In the preferred aspect of this invention, it is convenient to start with a 2 or 4-nitro or halobiphenyl compound. This results in the corresponding 2' or 4'-nitro or halobiphenylylglycolate.

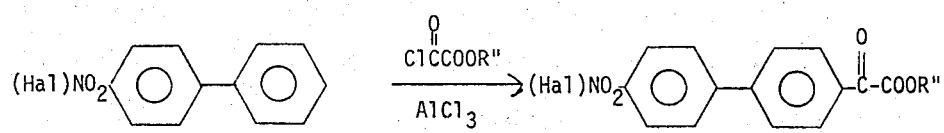

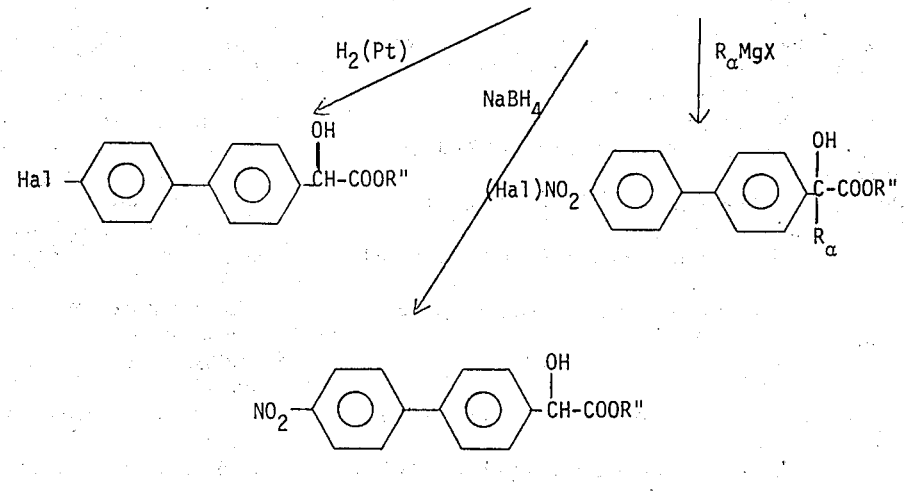

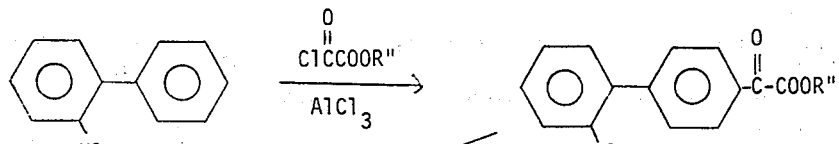

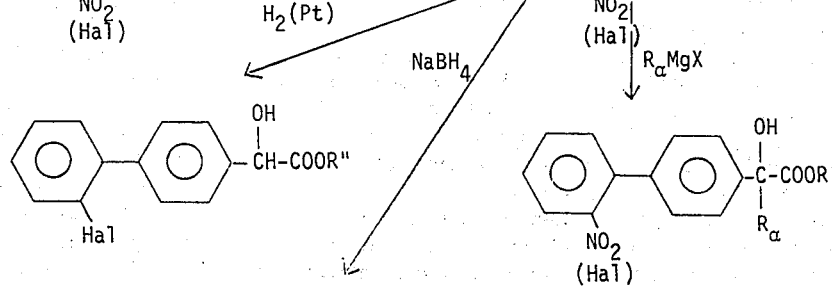

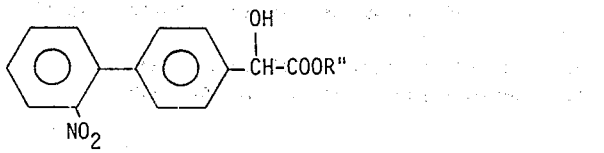

Compounds having substituents in the other ring may be prepared by carrying out a Friedel-Crafts, as above, with an alkyl or aralkyl oxalyl chloride on biphenyl. The resultant 4-biphenylylglyoxylate is then reacted with an alkyl Grignard reagent to form the α-alkyl-4-biphenylylglycolate or reduced to the glycolate by catalytic hydrogenation with platinum oxide or under sodium borohydride conditions. The glycolate may then be alkylated, halogenated or nitrated.

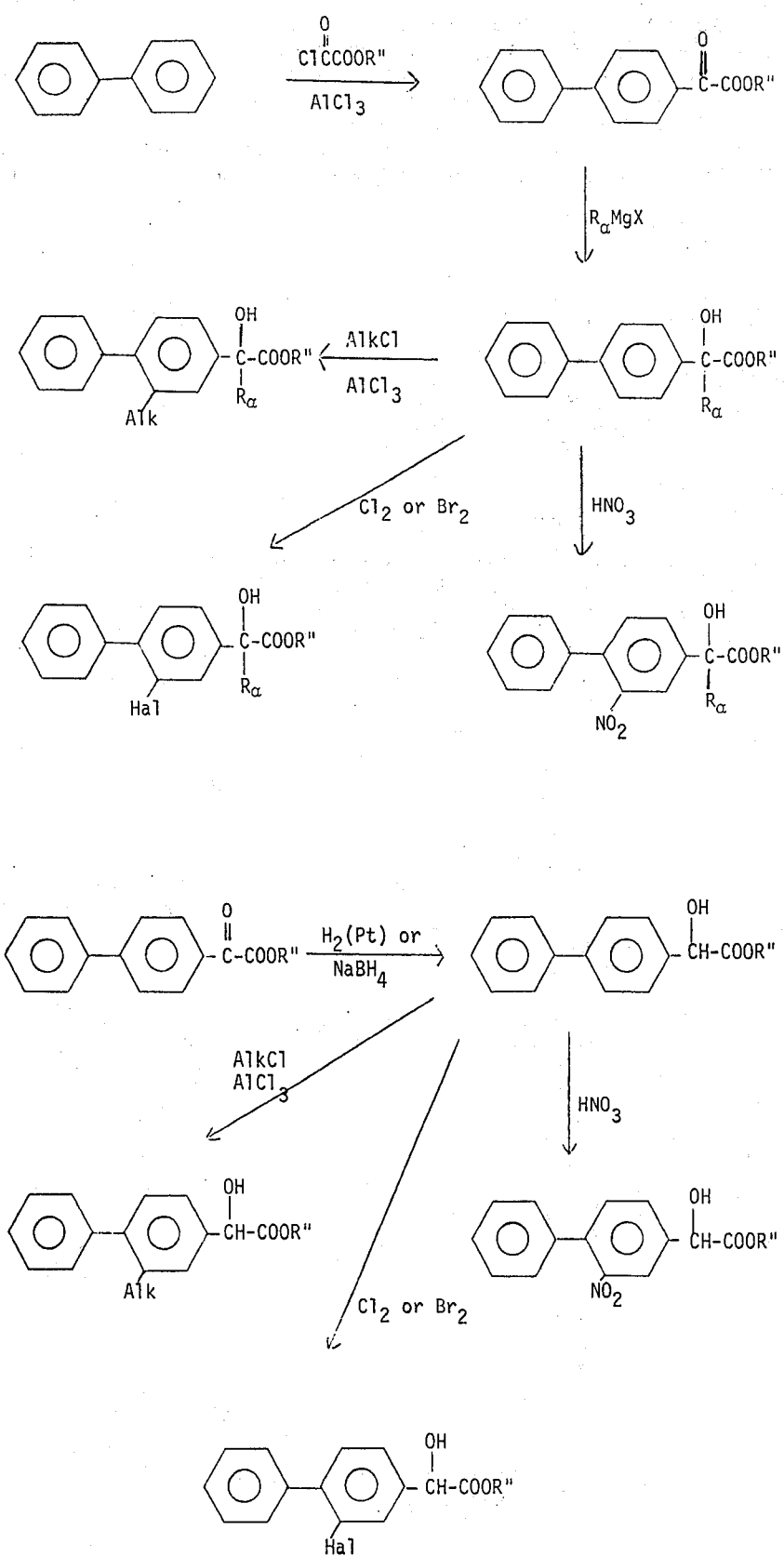

Chlorination or bromination may be carried out in the presence of a small amount of iodine dissolved in an inert solvent such as carbon tetrachloride. A solution of chlorine or bromine is then added while the temperature is held near 0°C. Nitration is carried out with fuming nitric acid at about 0°C. Alkylation is carried out under Friedel-Crafts conditions with an alkyl halide and aluminum chloride.

Appropriately desired end products having various R or R' substituents can be prepared by using suitable reactions in order to convert one group to another. Thus, for example, a 2'-halo-4-biphenylylglycolate in which halo is chloro, bromo or iodo may be a. reacted with cuprous cyanide in quinoline at about 150°C to produce a 2'-cyano-4-biphenylylglycolate:

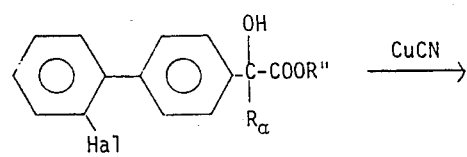

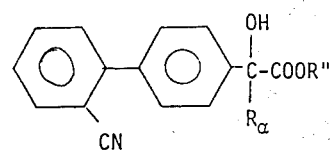

b. reacted with trifluoromethyliodide and copper powder at about 150°C in dimethylformamide to obtain a 2'-trifluoromethyl-4-biphenylylglycolate: [as described in Tetrahedron Letters: 47,4095 (1959)]

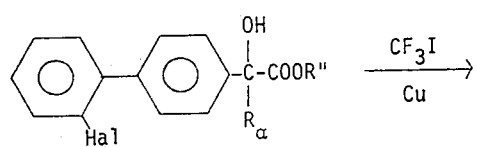

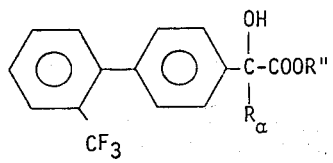

c. reacted with cuprous methanesulfinate in quinoline at about 150°C to obtain a 2'-methylsulfonyl-4-biphenylylglycolate:

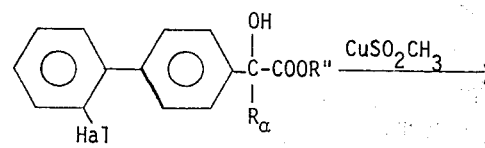

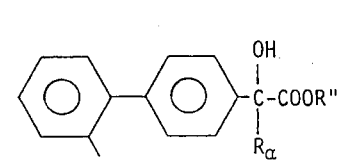

A 2'-nitro-4-biphenylylglycolate may be selectively hydrogenated to the corresponding amine.

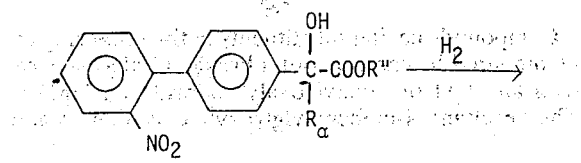

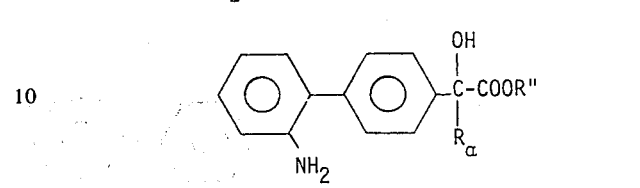

A 3-amino-4-biphenylylglycolate may then be a. mono- or dialkylated with loweralkyl halides or sulfates or acylated with loweracyl chlorides or anhydrides,

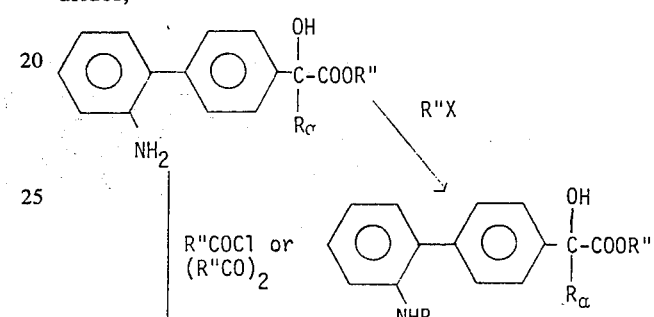

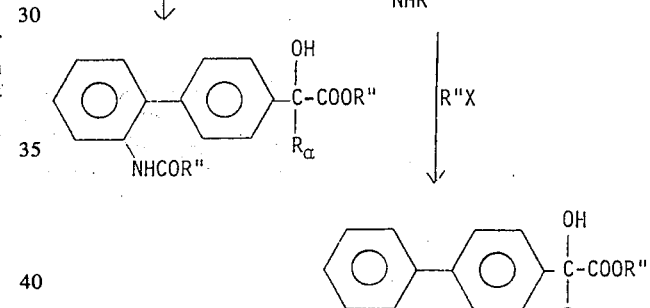

b. diazotized to the diazonium fluroborate which is then thermally decomposed to the 3-fluoro-4-biphenylylglycolate,

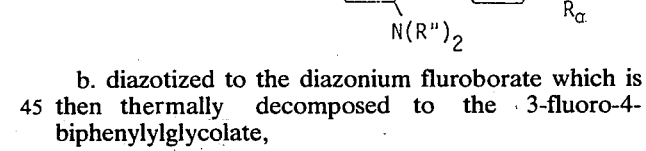

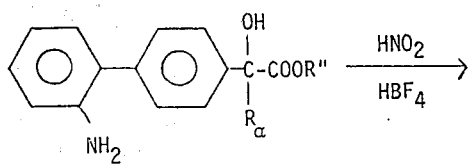

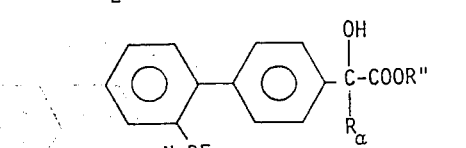

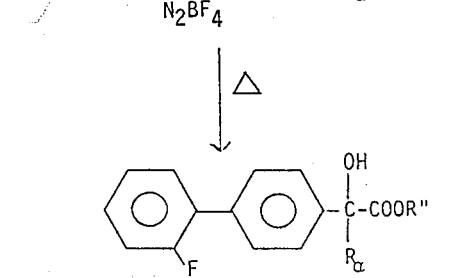

c. diazotized and heated in an aqueous medium to form the 3-hydroxy-4-biphenylylglycolate or heated in an alcohol to form the 3-alkoxy-4-biphenylylglycolate. The hydroxyl group may also be alkylated with loweralkyl halides or sulfates to the alkoxyl group or acylated with loweracyl chlorides or anhydrides to the acyloxy compound in the presence of a tertiary amine such as pyridine,

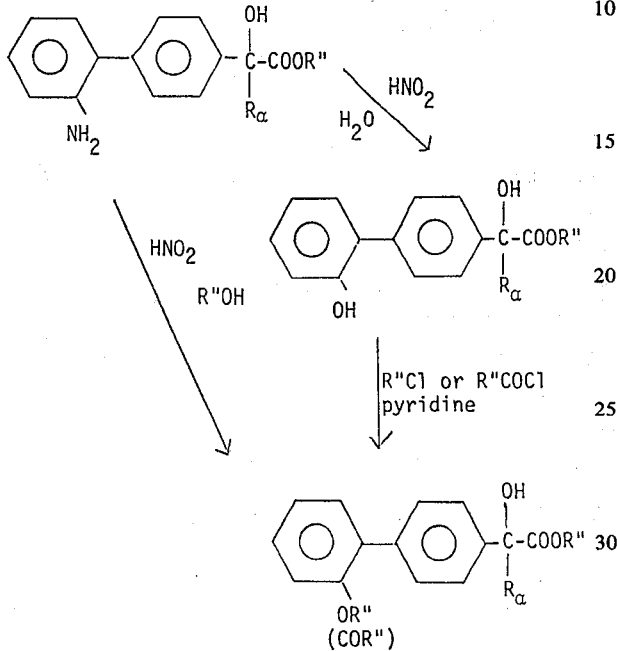

d. diazotized followed by a Sandmeyer type reaction to yield the halo group,

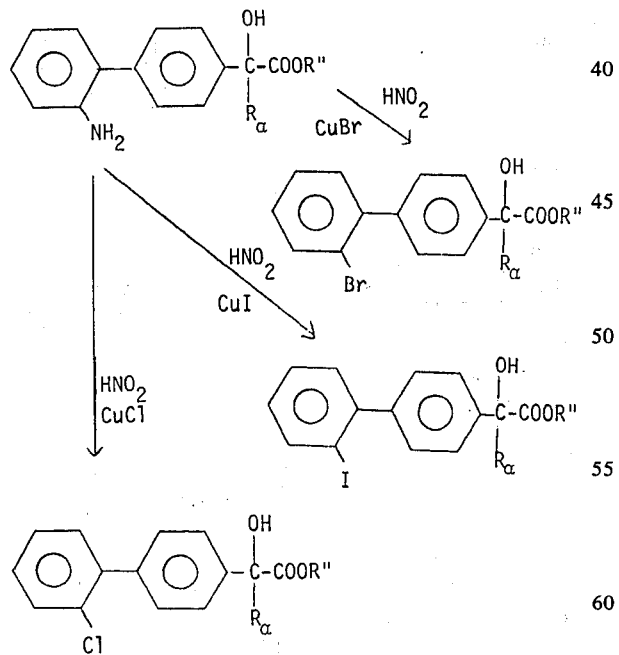

e. diazotized and heated with an aqueous solution of potassium iodide to prepare the 3-iodo-4-biphenylylglycolate, f. diazotized followed by reaction with potassium ethylxanthate followed by hydrolysis to obtain 3-mercapto-4-biphenylylglycolic acid which can be esterified to 9 3-mercapto-4-biphenylylglycolate. This in turn can be lower alkylated to the lower alkylthio and oxidized to the loweralkylsulfinyl and loweralkylsulfonyl groups or acylated to the acylthio compounds.

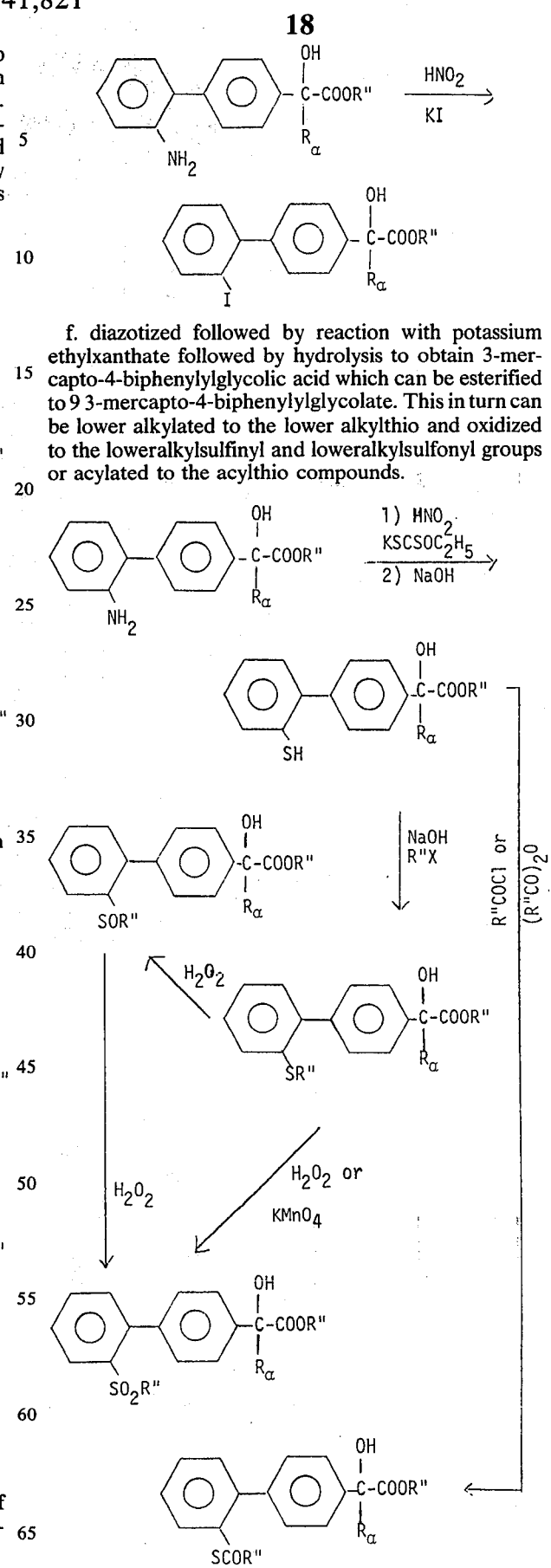

In a similar manner the 3 or 4' halo or nitro compounds may be converted to desired substituents.
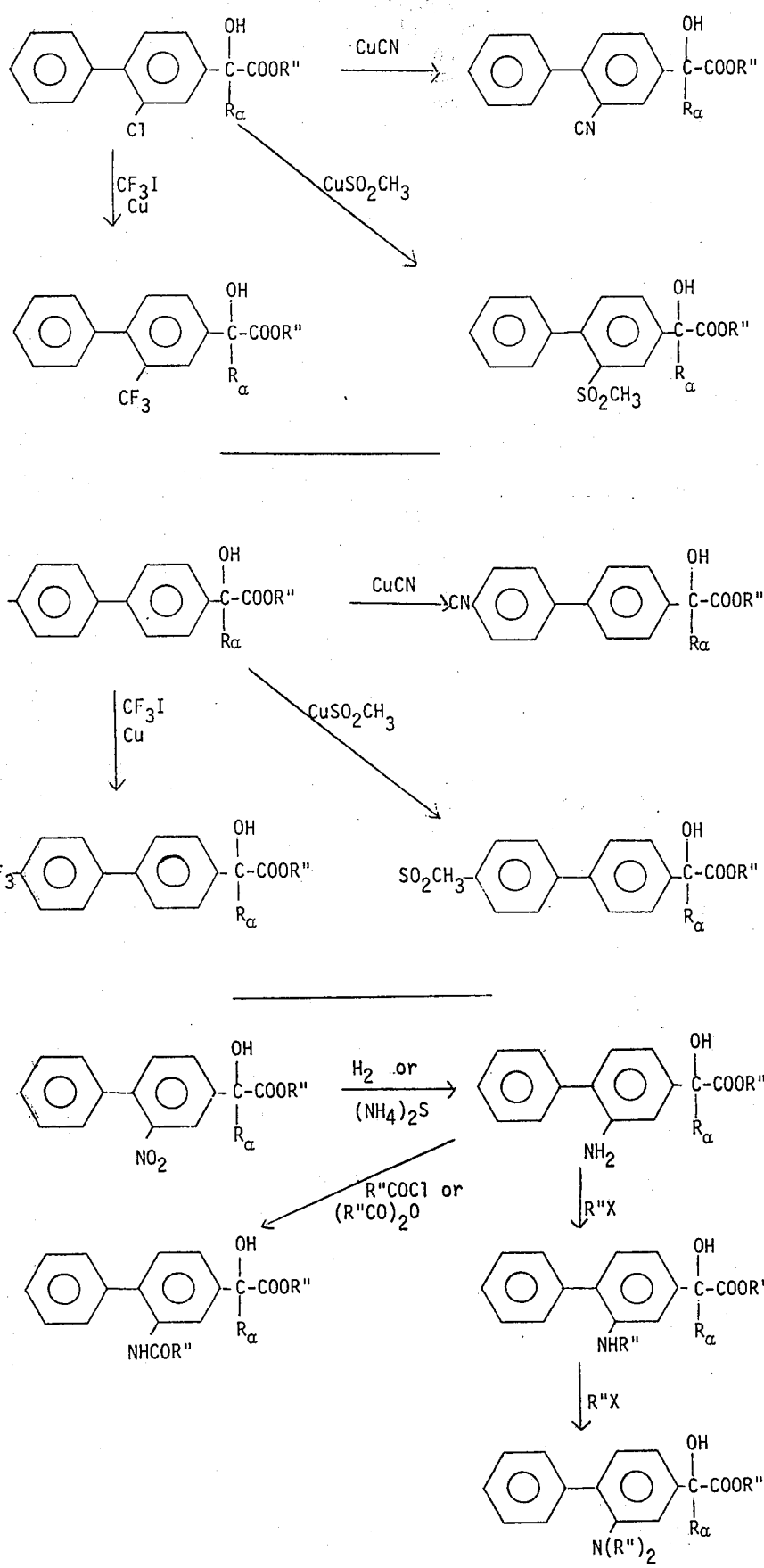

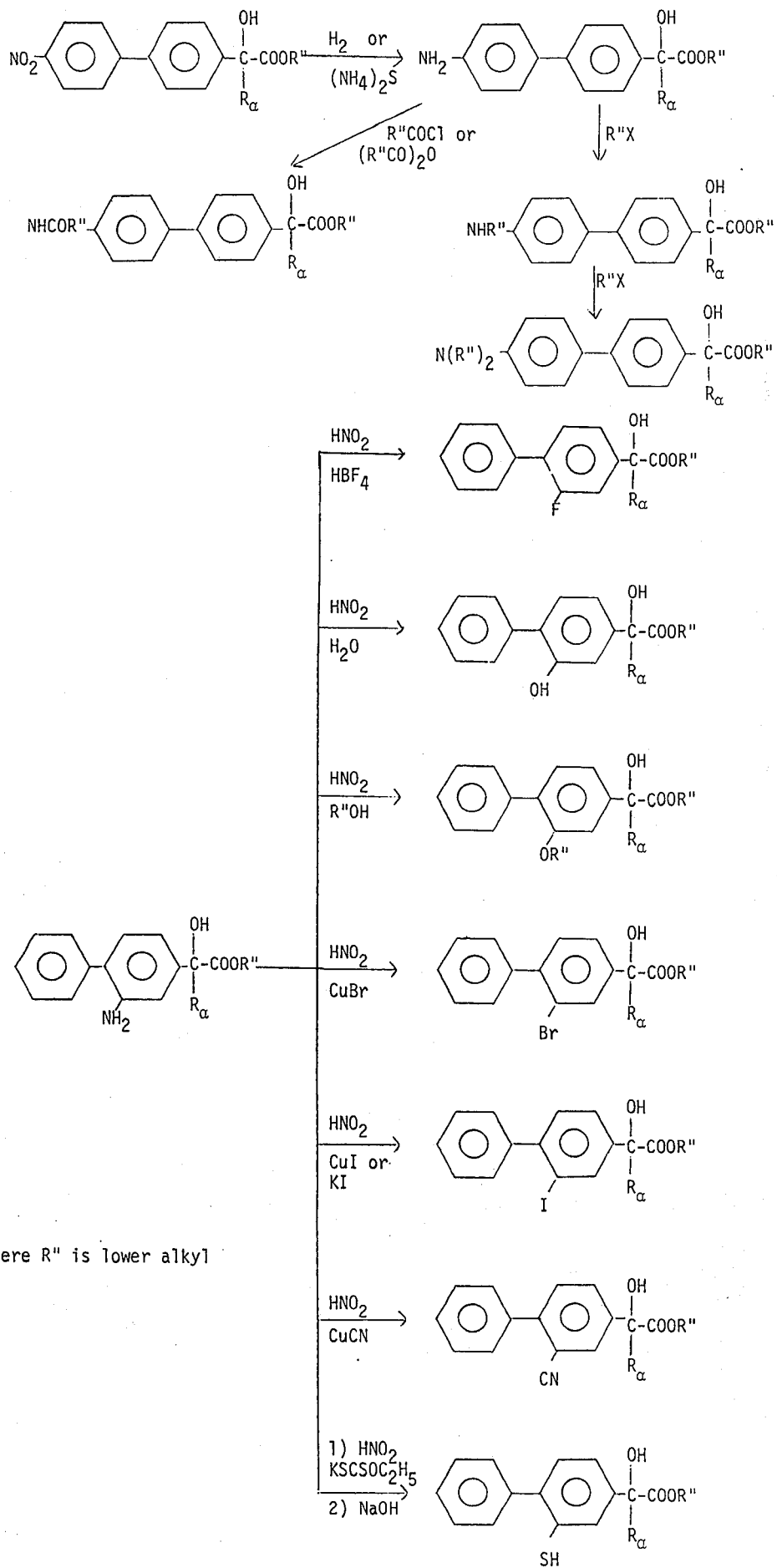
where R'' is lower alkyl

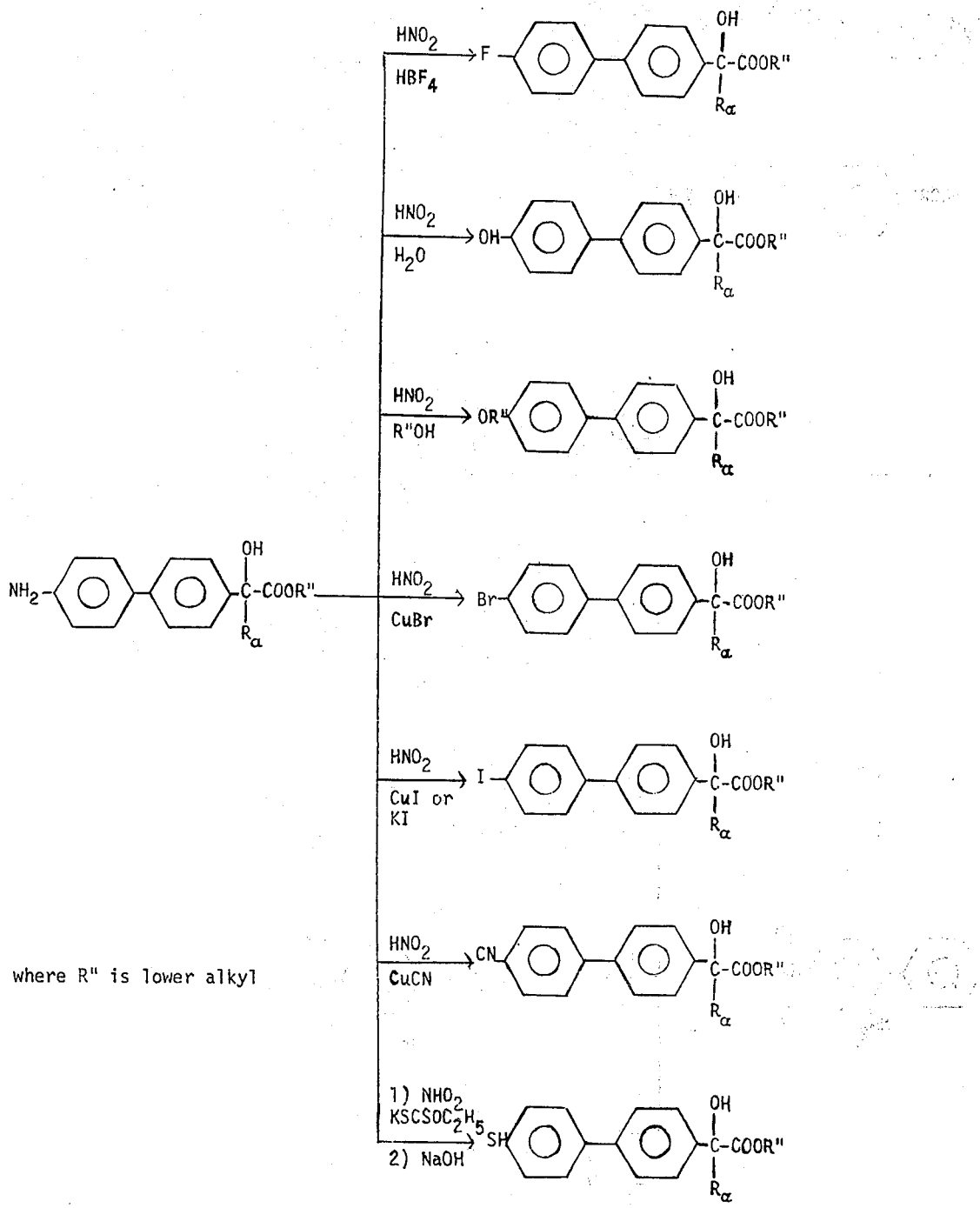
where R" is lower alkyl
Reaction of a substituted p-biphenylylglycolate ester with a nitrogen base such as ammonia, loweralkylamine, diloweralkylamine, cycloloweralkylamine, a nitrogen containing hetero compound such as piperidine, morpholine, piperazine, hydroxylamine and hydrazine gives the corresponding amide, hydroxamic acid, or hydrazide.

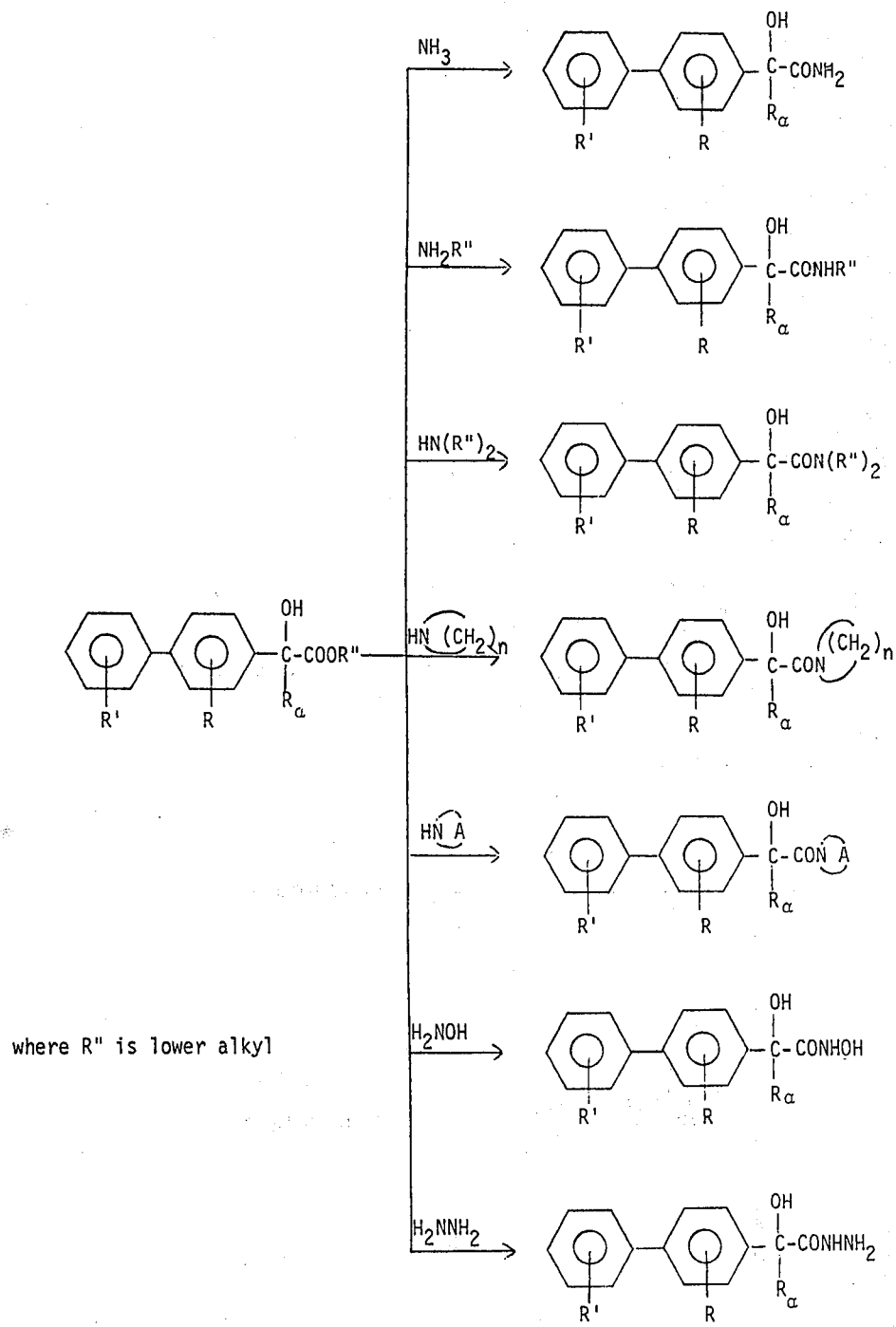

where R" is lower alkyl

The glycolate esters may be hydrolyzed to the corresponding p-biphenylylglycolic acid. Reaction of the glycolate ester or glycolic acid with an acid chloride YCl or acid anhydride YOY in the presence of a tertiary amine such as pyridine, picoline, or quinoline results in the formation of an hydroxy derivative of the glycolate. Examples of YCl and YOY include acetyl chloride, acetic anhydride, propionyl chloride, butyryl chloride, succinic anhydride, maleic anhydride, phthalic anhydride, benzoyl chloride, benzoic anhydride, benzyl chlorocarbonate, ethyl chlorocarbonate, dimethylcarbamyl chloride, dibutylcarbamyl chloride, benzenesulfonyl chloride, methanesulfonyl chloride.

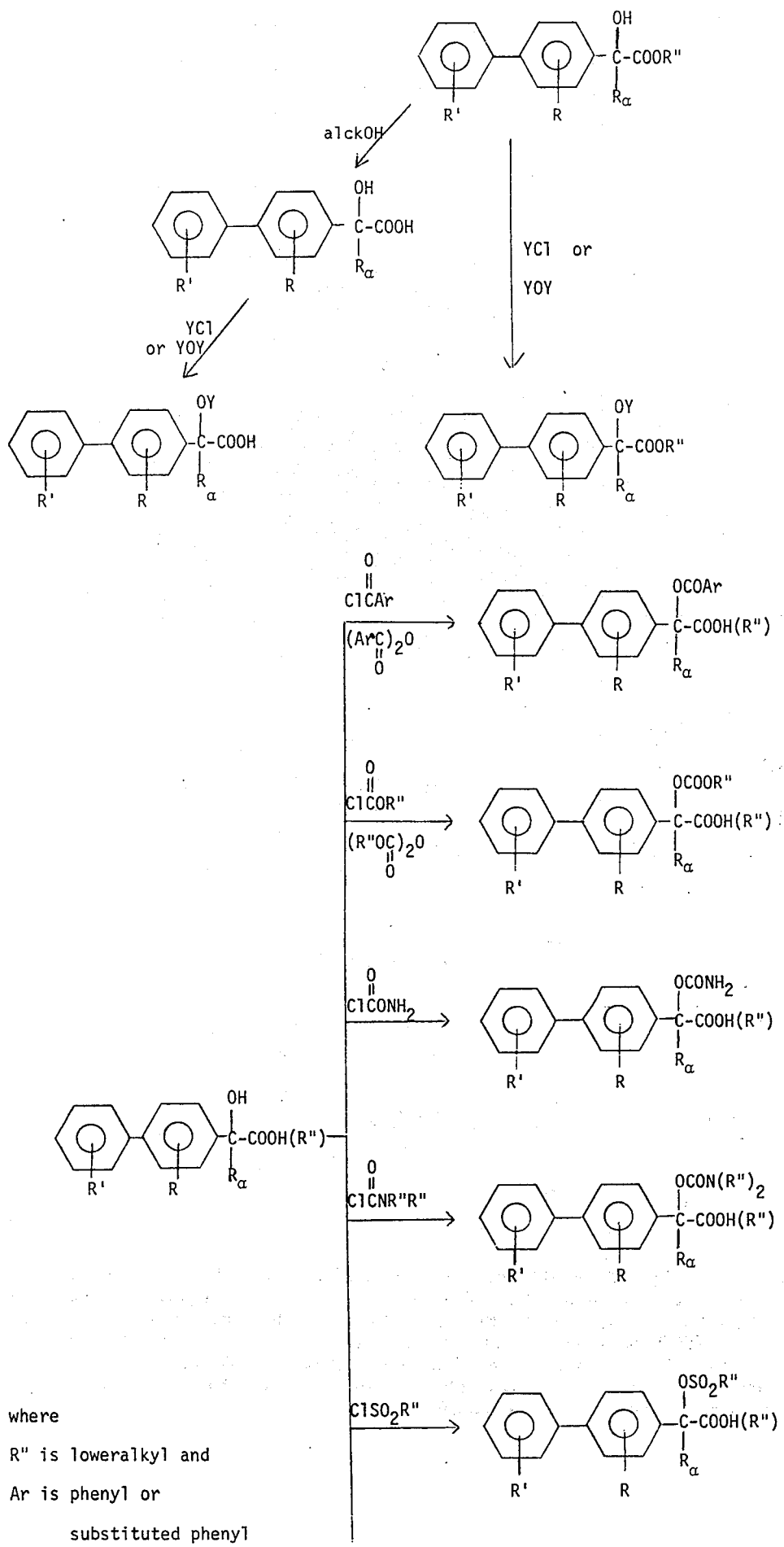
where
R" is loweralkyl and
Ar is phenyl or
substituted phenyl

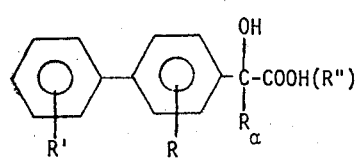
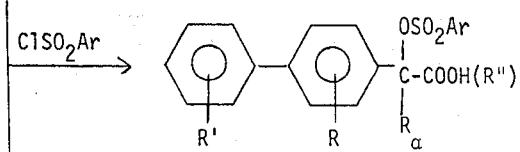
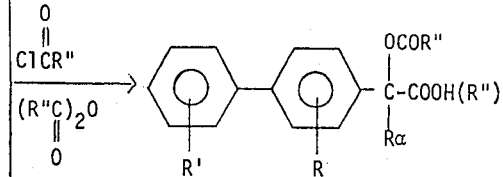
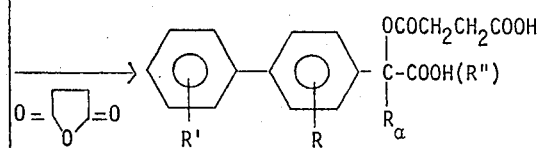
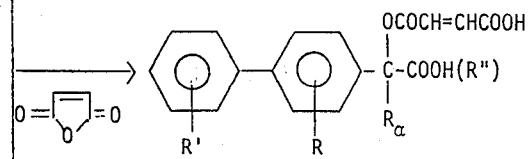
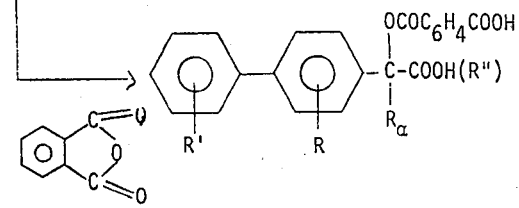
where
R″ is lower alkyl When a substituted 4-biphenylylglycolate is reacted with a phosphorus trihalide, phosphorus pentahalide, phosphorus oxyhalide, sulfurylhalide, thionyl halide, or sulfur halide, the corresponding substituted α-halo-4-biphenylylacetate is prepared.

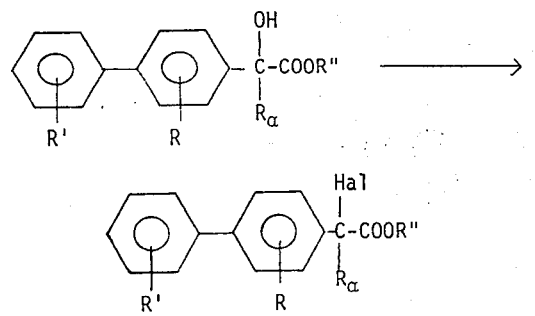

where R'' is lower alkyl;
where Hal is chloro, bromo or iodo.

Reaction of an α-sulfonate with a metal halide (preferably an alkali halide) results in the corresponding α-halo compound.

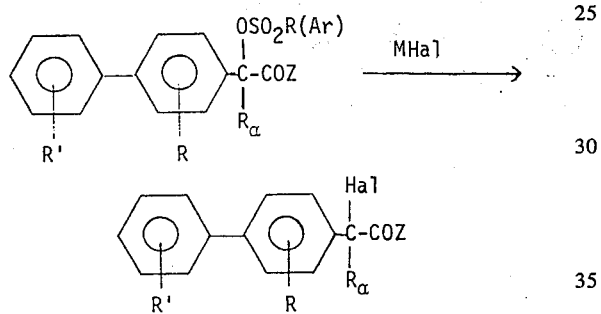

where Z is as described on page 4.

The corresponding α-haloacetic acid may be prepared by heating the ester with acetic acid containing the corresponding hydrogen halide.

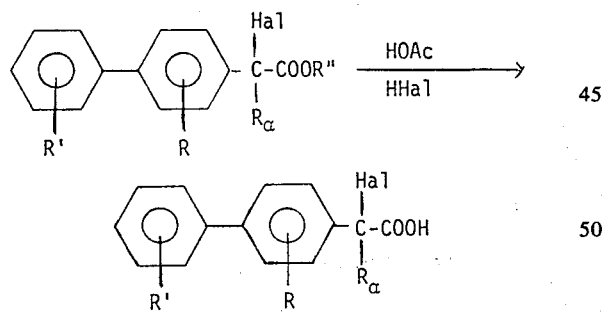

where R'' is lower alkyl.

The acid addition salts may then be formed by the action of one equivalent of a suitable base with the substituted α-halo-4-biphenylylacetic acid. Suitable bases thus include for example the alkali metal alkoxides such as sodium methoxide, etc., and the alkali metal and alkaline earth metal hydroxides, carbonates, bicarbonates, etc. (such as sodium hydroxide, potassium hydroxide, calcium hydroxide, potassium carbonate, sodium bicarbonate, magnesium bicarbonate, etc.). Also, the aluminum salts of the instant products may be obtained by treating the corresponding sodium salt with an appropriate aluminum complex such as aluminum hydroxy chloride hexahydrate, etc. The ammonium salts may be made by reaction with the corresponding amine such as methylamine, diethylamine, β-hydroxyethylamine, piperazine, piperidine, α-methylbenzylamine, cyclohexylamine, triethylamine, phenethylamine, etc.

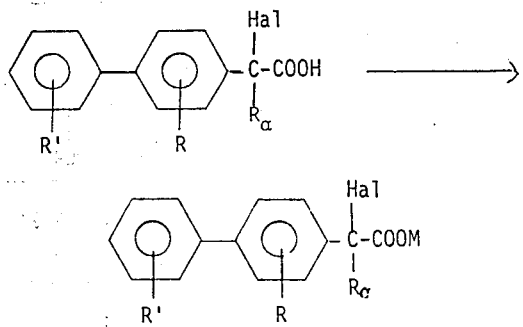

Reaction of a substituted α-halo-p-biphenylylacetate ester with a nitrogen base such as ammonia, loweralkylamine, diloweralkylamine, cycloloweralkylamine, a nitrogen containing hetero compound such as piperidine, morpholine, piperazine results in the corresponding amide. The acetate ester with hydroxylamine gives the corresponding hydroxamic acid, and with hydrazine gives the corresponding hydrazide.

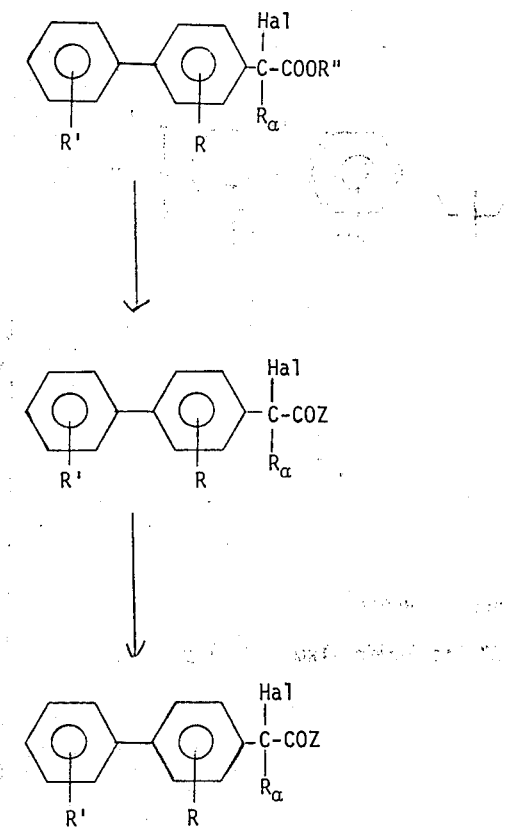

where:
Z
is -NH$_2$,
loweralkylamine.
diloweralkylamino,
cycloloweralkylamino,
—N̲A (where A is loweralkylidenyl or heteroloweralkylidenyl),
—NHOH or
—NHNH$_2$.

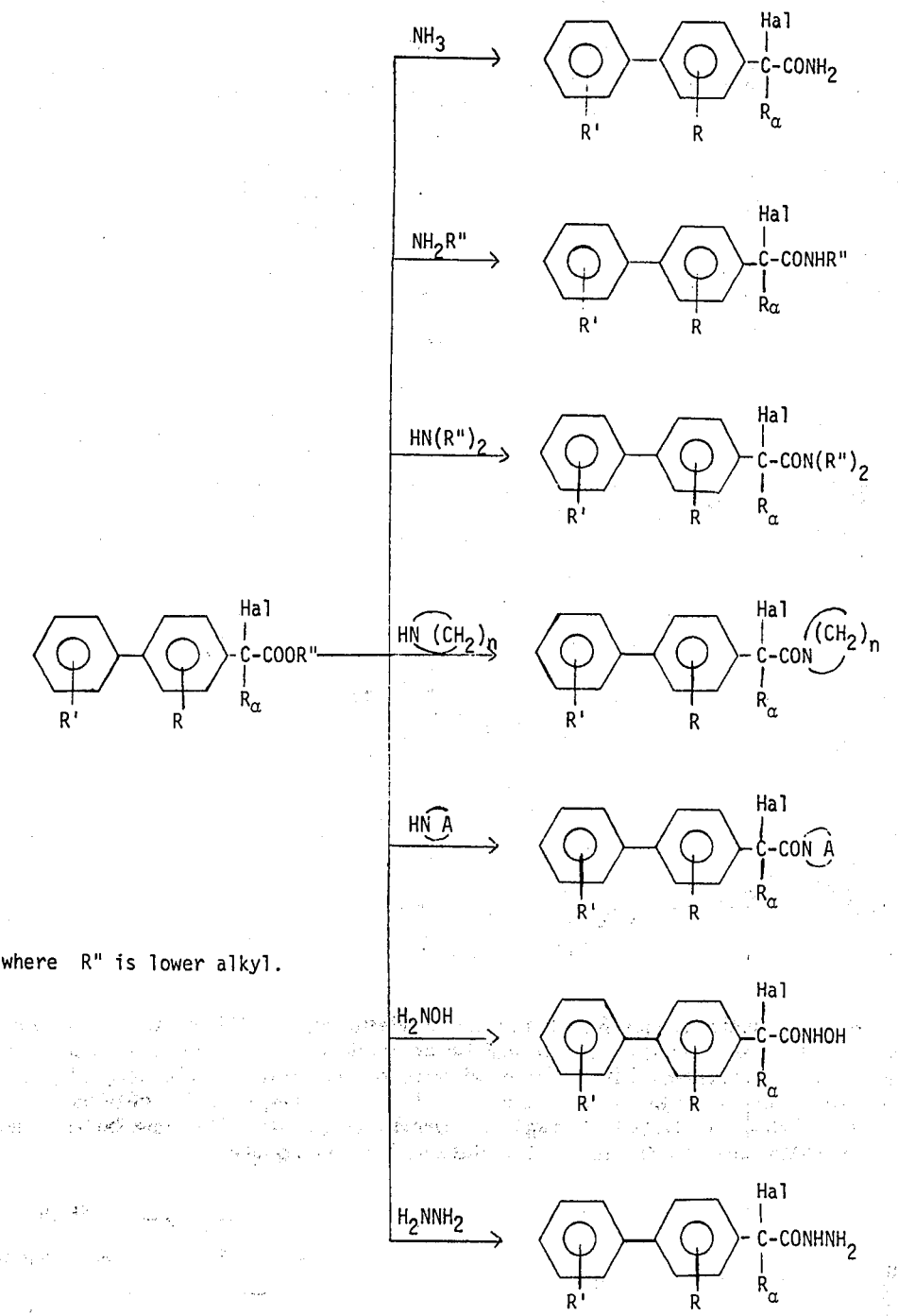
where R" is lower alkyl.
The α-halo-p-biphenylylacetamides, acethydroxamic acids, or acethydrazides can be prepared from the corresponding p-biphenylylglycolamides with thionyl halides according to the method of I. A. Smith, Chem. Berichte 71B:634 (1938).
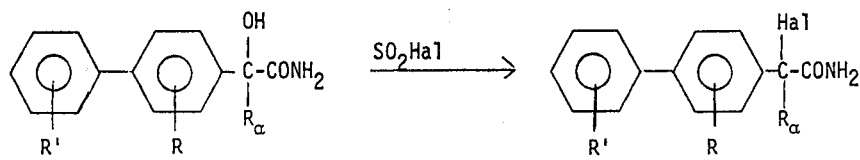

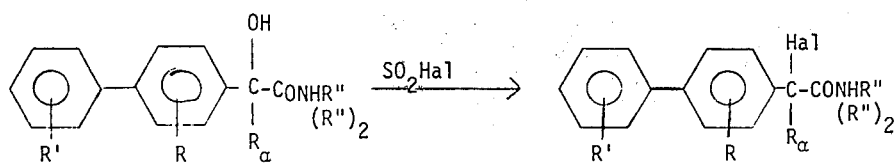

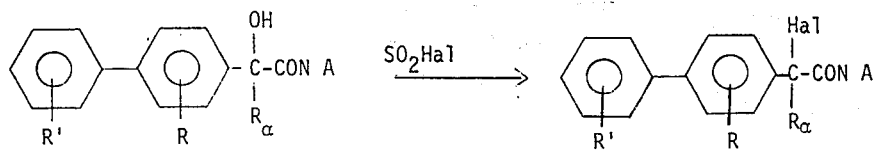

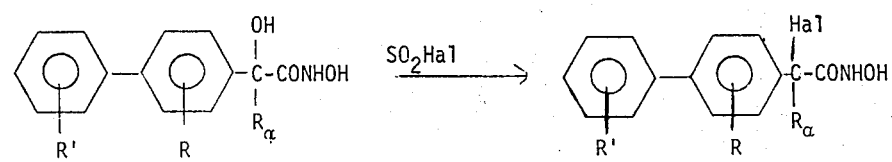

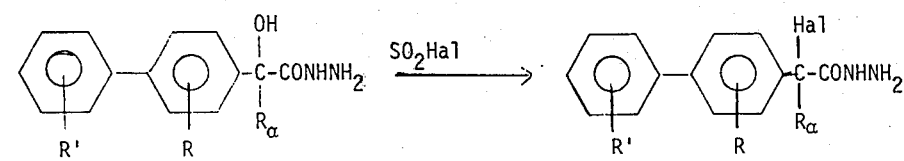

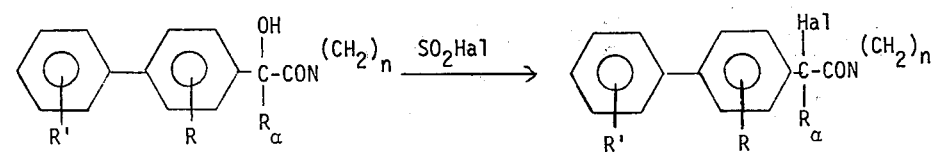

The substituted α-halo-p-biphenylylacetic acids and acid derivatives such as their salts, amides or esters may be reacted with various nucleophilic reagents which will replace the α-halogen group. Thus, for example, an alkali hydrosulfide, alkali thioalkanoate, alkali thiobenzoate, alkali loweralkylxanthate, thiourea, alkali thiocyanate, alkali thiosulfate, alkali loweralkylmercaptide, alkali sulfite or an alkali sulfinate may be reacted with the α-chloro, α-bromo or α-iodo-p-biphenylylacetic acid to form the corresponding derivative of the α-mercapto-p-biphenylylacetic acid. This may also be carried out on the α-sulfonate compounds.

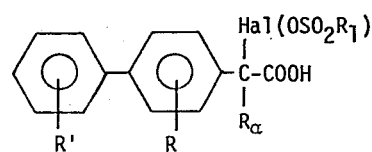

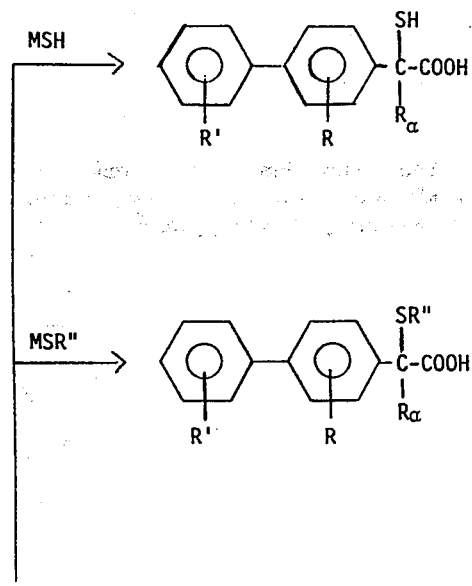

where:
$R_1$ is alkyl or aryl.
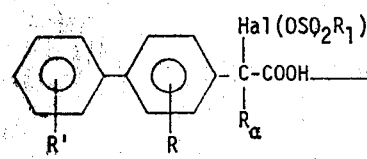
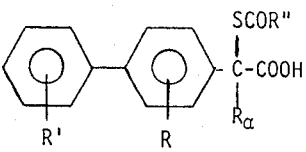 MSCOR″
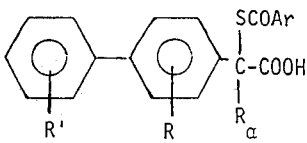 MSCOAr
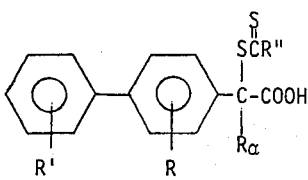 $\underset{\text{MSCR″}}{\overset{\text{S}}{\|}}$
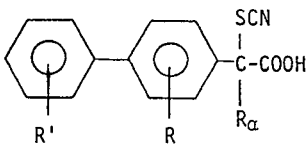 MSCN
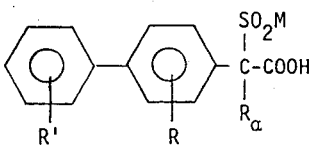 $MSO_2M$
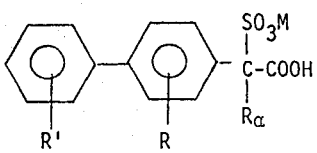 $MSO_3M$
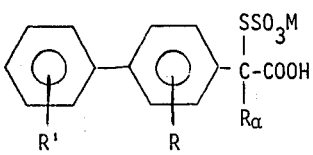 $MSSO_3M$
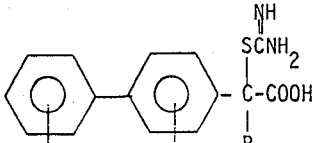 $\underset{HSCNH_2}{NH}$
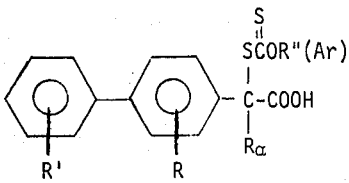 $\underset{MSCOR″(Ar)}{\overset{S}{\|}}$ The α-mercapto-p-biphenylylacetic acid may then be reacted with a loweralkyl chlorocarbonate, an alkali isocyanate in the presence of hydrogen chloride, a acid may also be reacted with succinic anhydride, maleic anhydride or phthalic anhydride to form the corresponding derivative.

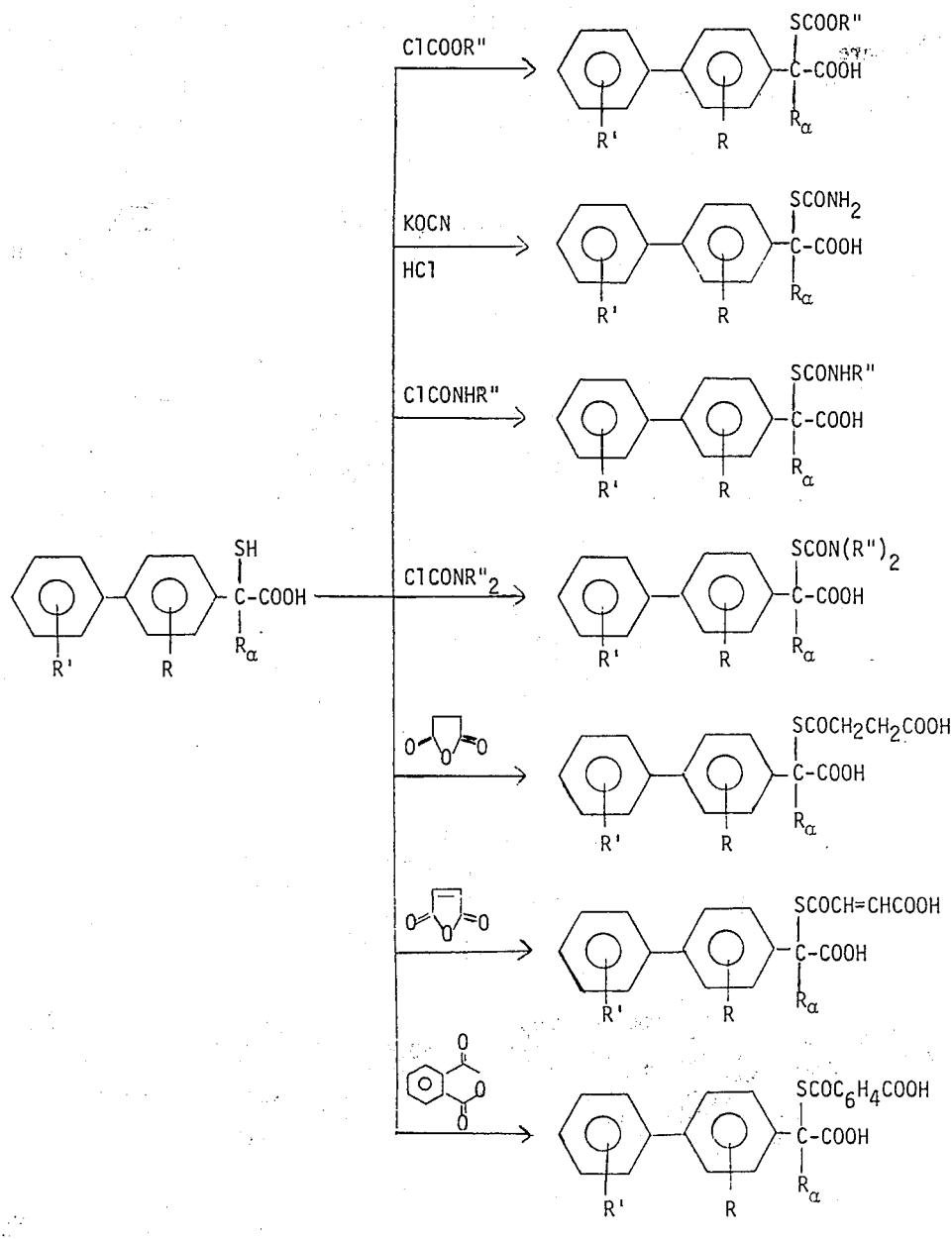

loweralkylcarbamyl chloride or a diloweralkylcarbonyl chloride to form the corresponding α-mercaptoacetic acid derivative. The α-mercapto-p-biphenylylacetic The α-loweralkylmercapto-p-biphenylylacetic acid may further be oxidized to the loweralkylsulfinyl and loweralkylsulfonyl groups.

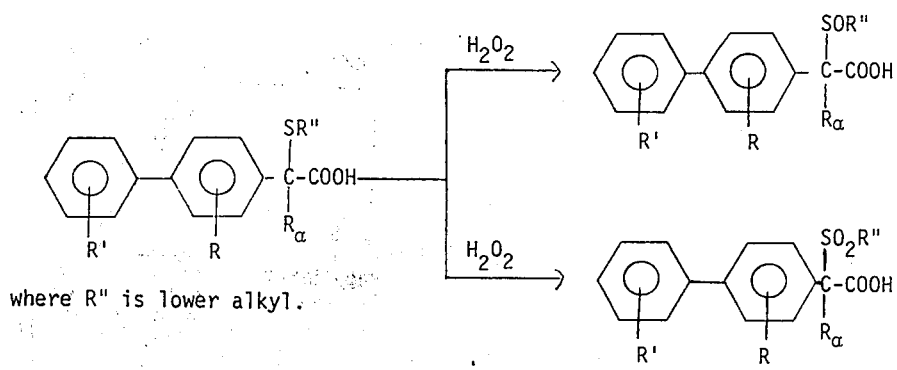

where R" is lower alkyl.

In an analogous manner the various α-mercaptoacetates, α-mercaptoamides and the α-mercaptoacetic acid salts may be prepared from the corresponding α-haloacetates, α-haloacetamides, α-haloacetic acid salts.
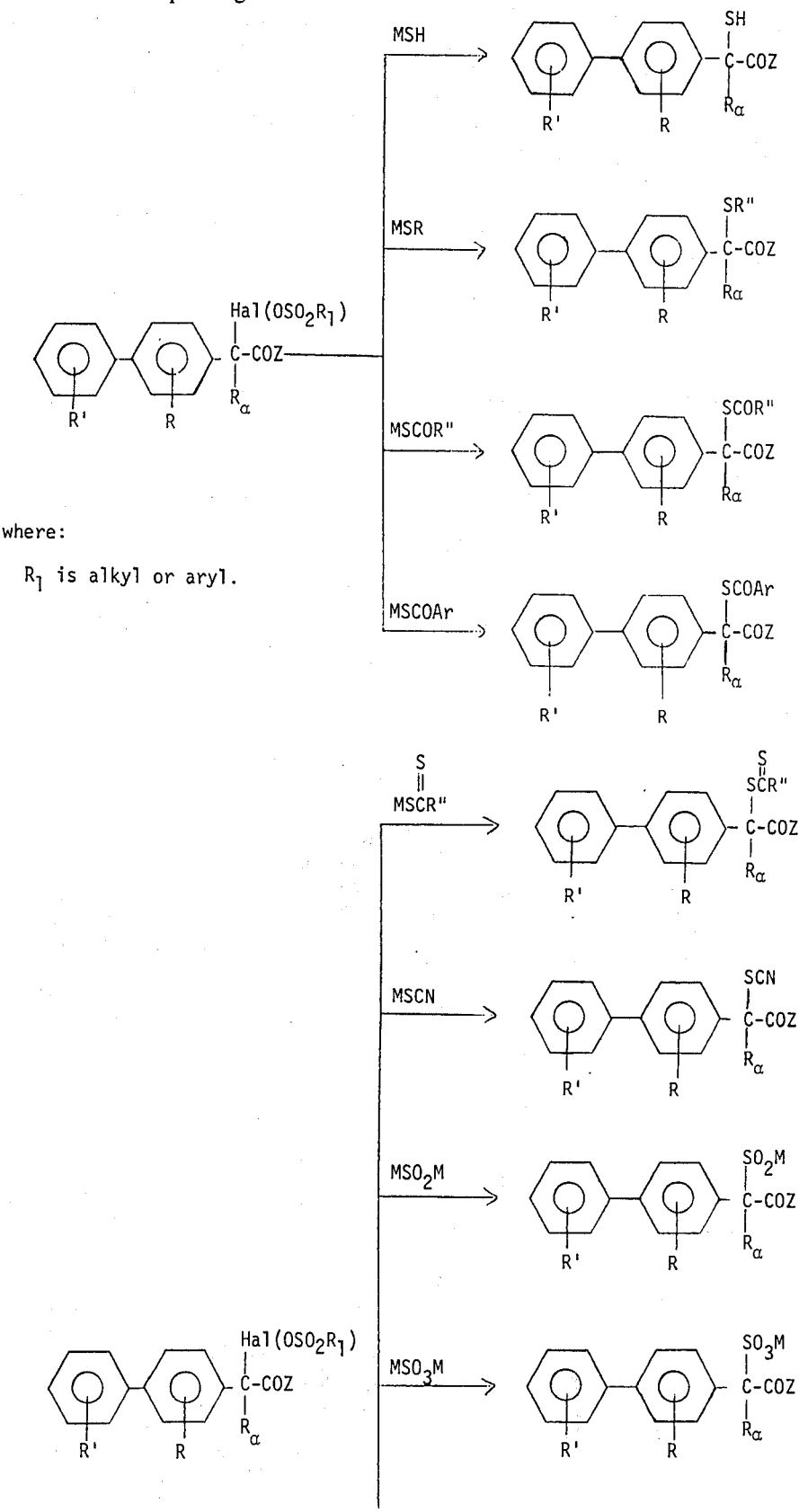
where:
$R_1$ is alkyl or aryl.

where:

M is an alkali metal salt;

R" is lower alkyl;

Ar is phenyl or tolyl;

$R_1$ is alkyl or aryl.

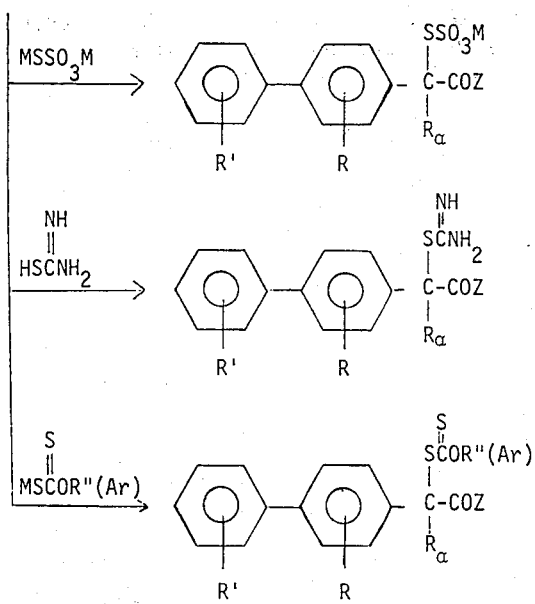

Of course it will be understood by one skilled in the art that variations in the above procedures can be employed which will give that sequence of reactions which will result in the desired R, R', X and Z substituents.

These and other equivalent methods for the preparation of the acid, ester, amide, salts and α-mercapto derivatives of the instant products will be apparent to those having ordinary skill in the art.

The products of this invention may be obtained as racemic mixtures of their dextro and levorotatory isomers. These may be separated by any of the various methods of resolution. One method that may be employed is combining the racemic compound with an optically active compound by salt formation, ester formation, or amide formation to form two diastereomeric products. If the instant acids are added to an optically active base, then two diastereomeric salts are produced which possess different properties and different solubilities and can be separated by fractional crystallization. When the salts have been completely separated by repeated crystallization, the base is split off by acid hydrolysis and the pure $d$ or $l$ acids are obtained. Preferably, an α-mercapto derivative of a p-biphenylylacetic acid is reacted in alcoholic or acetone solution with an equivalent amount of the optically primary, secondary or tertiary amine such as cinchonidine, cinchonine, quinine, ephedrine, α-methybenzylamine, sec-butylamine, secamylamine, etc. The diastereomeric amine salts produced thereby, are separated by fractional crystallization and each optically active salt is hydrolyzed with dilute mineral acid to produce the dextro or levo form of the -mercapto derivative of the p-biphenylylacetic acid. Alternatively, an α-mercapto derivative of a p-biphenylylacetate ester may be reacted with an optically active primary or secondary amine such as ephedrine, α-methylbenzylamine, sec-butylamine, etc., to produce a mixture of diastereomeric acetamides which may be separated by fractional crystallization. Each optically active amide may be hydrolyzed with mineral acid to its respective optically active acid.

Still alternatively, an α-mercapto derivative of a p-biphenylyl-acetate may be reacted with an optically active alcohol such as l-menthol or d-borneol, or $l$-α-methylbenzylalcohol, to produce a mixture of diastereomeric acetate esters which may be separated by fractional crystallization. Each optically active ester may be hydrolyzed with mineral acid or alkali to its respective optically active acid. The optically active acids can also be recovered from the α-methylbenzyl esters by hydrogenolysis in the presence of palladium.

The resolution may also be carried out as above on the glycolic acid, ester or amide. The optical isomer in turn may then be converted to the α-halo compound which is then reacted as above to give the α-mercapto derivatives.

The racemic chloroacetic acids, esters and amides may also be resolved into their optical isomers by the processes described for the α-mercapto acids, esters and amides.

We have found that the compounds of this invention exercise a useful degree of anti-inflammatory activity in mammals and are effective in the treatment of associated pain and fever and in like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or antipyretic agent.

For these purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/Kg. Comparative dosages may be used in topical, parenteral or rectal administration.

Dosage forms may be prepared according to any method known to the art of the manufacture of pharmaceutical compositions and such compositions may contain one or more agents; for example, sweetening agents, flavoring agents, coloring agents, preserving agents, etc. Further, the active α-mercapto-p-biphenylylacetic acids or their derivatives may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example, magnesium stearate, talc, etc., binding agents; for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally-occurring gums, etc., and non-irritating excipients; for example, cocoa butter and polyethylene glycols.

Various tests in animals can be carried out to show the ability of the α-mercapto-p-biphenylylacetic acids and derivatives of this invention to exhibit reactions that can be correlated with anti-inflammatory activity in humans. One such test is the Carrageenan paw edema test, which shows the ability of the instant compounds to inhibit edema niduced by injection of an inflammatory agent such as carrageenan into the tissues of the paw of a rat against non-inflammed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone and prednisolone. In view of the results of this test, the α-mercapto-p-biphenylylacetic acids and derivatives can be considered to be active anti-inflammatory agents.

One method for measuring the pain threshold of the α-mercapto-p-biphenylylacetic acids and derivatives is the Randall-Selitto test. Analgesic activity is shown by antinocieceptive testing of the inflammed foot of rats and a measurement of their pain response.

Antipyretic assay is carried out by yeast-induced fever tests of subcutaneously injected rats. The measurement of rectal temperature is carried out to determine the response by the test compounds.

In view of the results of the above tests, the αmercapto-p-biphenylacetic acids and derivatives of this invention are considered to have valuable analgesic and antipyretic properties.

Other tests which can be correlated to show significant activities are the "phenylquine writhing" test for analgesia, "polyarthritis in rats" and "ultra-violet erythema in guinea pigs."

The following are detailed examples which show the preparation of the compounds of this invention. They are to be construed as illustrations of said compounds and are not intended to be limitations thereof.

EXAMPLE 1

Ethyl 2'-chloro-4-biphenylylglyoxylate

2-Chlorobiphenyl 57 g. (0.33 mole) and 50.5 g. (0.37 mole) of ethyl oxalyl chloride are dissolved in 200 ml. of dry 1,1,2,2-tetrachloroethane. Anhydrous aluminum chloride 52 g. (0.39 mole) is added in small portions to the reaction mixture with stirring over 2 hours. During the addition, the temperature of the mixture is maintained between 16°–18°C. The mixture is stirred for an additional hour and allowed to stand overnight. The solution is then slowly poured into 1500 ml. of iced saline solution with stirring. After standing, two layers form. The aqueous layer is extracted with 500 ml. of ether and the ether extract is combined with the organic layer which is dissolved in 1500 ml. of ether and separated. The ether solution is washed with 10 × 100 ml. portions of a 1:1 mixture of saturated sodium chloride solution and 10% HCl solution, and 5 × 100 ml. portions of water. The ether solution is then dried over anhydrous magnesium sulfate for 1 hour and filtered. The solvents are removed by distillation under reduced pressure and the residue distilled to obtain ethyl 2'-chloro-4-biphenylylglyoxylate.

When 2-chlorobiphenyl in the above example is replaced with biphenyl, 4-chlorobiphenyl, 2-nitrobiphenyl, 4-nitrobiphenyl, 2-methylbiphenyl, 4-methylbiphenyl, 2-bromobiphenyl or 4-bromobiphenyl then the product obtained is ethyl 4-biphenylylglyoxyxlate, ethyl 4'-chloro-4-biphenylylglyoxylate, ethyl 2'-nitro-4-biphenylylglyoxylate, ethyl 4'-nitro-4-biphenylylglyoxylate, ethyl 2'-methyl-4-biphenylylglyoxylate, ethyl 4'-methyl-4-biphenylylglyoxylate, ethyl 2'-bromo-4-biphenylylglyoxylate or ethyl 4'bromo-4-biphenylylglyoxylate.

When ethyl oxalyl chloride in the above example is replaced with methyl oxalyl chloride, propyl oxalyl chloride, i-propyl oxalyl chloride, t-butyl oxalyl chloride, or benzyl oxalyl chloride then the product obtained is methyl 2'-chloro-4-biphenylylglyoxylate, propyl 2'-chloro-4-biphenylylglyoxylate, i-propyl 2'-chloro-4-biphenylylglyoxoylate, t-butyl 2'-chloro-4-biphenylylglyoxylate, or benzyl 2'-chloro-4-biphenylylglyoxylate.

EXAMPLE 2

Ethyl α-methyl-2'-chloro-4-biphenylylglycolate

A solution of methylmagnesium iodide is prepared from 6.7 g. (0.047 mole) of methyl iodide, 1.24 g (0.051 g-atom) of magnesium turnings and 40 ml. of anhydrous ether. This solution is added over a period of 1 hour to a solution of 14.4 g. (0.05 mole) of ethyl 2'-chloro-4-biphenylylglyoxylate. The addition is carried out with vigorous stirring at 0°–5°C. The mixture is then allowed to warm to room temperature over 10 hours. The mixture is poured into an ice-cold solution of 0.2 M-sulfuric acid. The ether layer is separated, extracted with 1% sulfuric acid, dried over magnesium sulfate, filtered and evaporated to obtain ethyl α-methyl-2'-chloro-4-biphenylylglycolate.

When ethyl 2'-chloro-4-biphenylylglyoxylate in the above example is replaced by the glyoxylates of Example 1, then the products prepared are:
ethyl α-methyl-4-biphenylylglycolate
ethyl α-methyl-4'-chloro-4-biphenylylglycolate
ethyl α-methyl-2'-nitro-4-biphenylylglycolate
ethyl α-methyl-4'-nitro-4-biphenylylglycolate
ethyl α-methyl-2'-methyl-4-biphenylylglycolate
ethyl α-methyl-4'-methyl-4-biphenylylglycolate
ethyl α-methyl-2'-bromo-4-biphenylylglycolate
ethyl α-methyl-4'-bromo-4-biphenylylglycolate When the Grignard reagent used is ethylmagnesium iodide, propylmagnesium iodide or butylmagnesium iodide, then the product prepared is
ethyl α-ethyl-2'-chloro-4-biphenylylglycolate
ethyl α-propyl-2'-chloro-4-biphenylylglycolate
ethyl α-butyl-2'-chloro-4-biphenylylglycolate

2'3

Ethyl 2'-chloro-4-biphenylylglycolate

Into a Paar hydrogenation bottle is added 41.5 g. (0.144 mole) of ethyl 2'-chloro-4-biphenylylglyoxylate, 2 ml. of 0.1 M-ferrous sulfate solution, 220 ml. of isopropionyl and 1.0 g. of 85.1% platinum oxide. The mixture is shaken for 2 hours at room temperature with hydrogen gas until 0.144 mole of hydrogen is absorbed. The catalyst is then filtered off and the solution is evaporated in vacuo and the residue fractionally distilled to obtain ethyl 2'-chloro-4-biphenylylglycolate.

When ethyl 2'-chloro-4-biphenylylglyoxylate in the above example is replaced by the glyoxylates of Example 1, then the products prepared are:
ethyl 4-biphenylylglycolate
ethyl 4'-chloro-4-biphenylylglycolate
ethyl-2'-nitro-4-biphenylylglycolate
ethyl 4'-nitro-4-biphenylylglycolate
ethyl 2'-methyl-4-biphenylylglycolate
ethyl 4'-methyl-4-biphenylylglycolate
ethyl 2'-bromo-4-biphenylylglycolate
ethyl 40'-bromo-4-biphenylylglycolate

EXAMPLE 4

Ethyl 3-chloro-4-biphenylylglyoxylate

Ethyl p-biphenylylglyoxylate 96.6 g. (0.38 mole) and 6.1 g. of iodine (0.048 mole) and dissolved in 100 ml. of carbon tetrachloride. To this solution is added a solution of 40.4 g. (0.57 mole) of chlorine dissolved in 365 ml. of carbon tetrachloride over a period of 2 hours. During the addition, the temperature of the reaction mixture is maintained at 0°C. The mixture is stirred for 3 hours and allowed to stand with gradual warming to room temperature over 15 hours. The solvent is removed by distillation under reduced pressure. The residue is fractionally distilled to obtain ethyl 3-chloro-4-biphenylylglyoxylate When bromine is used in place of chlorine in the above example then the product obtained is ethyl 3-bromo-4-biphenylylglyoxylate.

EXAMPLE 5

Ethyl 3-nitro-4-biphenylylglyoxylate

Ethyl p-biphenylylglyoxylate 16.7 g. (0.066 mole) is added to ice-cold concentrated sulfuric acid (18 ml.) and stirred with cooling for 5 minutes. Concentrated nitric acid (Sp. G. 1.51) (2.5 Ml.) is added dropwise, maintaining the temperature between 30° and 40° by water cooling if necessary. After addition of the nitric acid is complete, the mixture is stirred for ½ hour, then poured into water. The mixture is made alkaline with sodium hydroxide, then extracted with ether. The ether extract is washed, dried over sodium sulfate, evaporated and the residue is fractionally distilled to obtain ethyl 3-nitro-4-biphenylylglyoxylate.

EXAMPLE 6

When ethyl 3-chloro-4-biphenylylglyoxylate, ethyl 3-bromo-4-biphenylylglyoxylate and ethyl 3-nitro-4-biphenylylglyoxylate are used in place of ethyl 2'-chloro-4-biphenylylglyoxylate in Examples 2 and 3, then the products prepared are:
ethyl α-methyl-3-chloro-4-biphenylylglycolate
ethyl α-methyl-3-bromo-4-biphenylylglycolate
ethyl α-methyl-3-nitro-4-biphenylylglycolate
ethyl α-ethyl-3-chloro-4-biphenylylglycolate
ethyl α-ethyl-3-bromo-4-biphenylylglycolate
ethyl α-ethyl-3-nitro-4-biphenylylglycolate
ethyl α-propyl-3-chloro-4-biphenylylglycolate
ethyl α-propyl-3-bromo-4-biphenylylglycolate
ethyl α-propyl-3-nitro-4-biphenylylglycolate
ethyl α-butyl-3-chloro-4-biphenylylglycolate
ethyl α-butyl-3-bromo-4-biphenylylglycolate
ethyl α-butyl-3-nitro-4-biphenylylglycolate
ethyl 3-chloro-4-biphenylylglycolate
ethyl 3-bromo-4-biphenylylglycolate
ethyl 3-nitro-4-biphenylylglycolate

EXAMPLE 7

Ethyl 2'-trifluoromethyl-4-biphenylylglycolate

To a solution of 0.01 moles of ethyl 2'-bromo-4-biphenylylglycolate in 50 ml. of dimethylformamide is added 0.15 moles of trifluoromethyl iodide and 0.02 g. of copper powder. The reaction is shaken in a sealed tube for 5 hours at 140°C, cooled and then filtered and evaporated in vacuo. 200 ml. of water is added to the residue and extracted with ether. The ether extract is dried, evaporated to dryness and distilled to obtain ethyl 2'-trifluoromethyl-4-biphenylylglycolate.

When ethyl 3-bromo-4-biphenylylglycolate or ethyl 4'-bromo-4-biphenylylglycolate are used in the above procedure, then the products prepared are ethyl 3-trifluoromethyl-4-biphenylylglycolate or ethyl 4'-brifluoromethyl-4-biphenylylglycolate.

When ethyl α-methyl-2'-bromo-4-biphenylylglcolate, ethyl α-methyl-3-bromo-4-biphenylylglycolate or ethyl α-methyl-4'-bromo-4-biphenylylglycolate are used in the above procedure then the products prepared are ethyl α-methyl-2'-trifluoromethyl-4-biphenylylglycolate, ethyl 3-trifluoromethyl-4-biphenylylglycolate or ethyl 4'-trifluoromethyl-4-biphenylylglycolate.

EXAMPLE 8

Ethyl 2'-amino-4-biphenylylglycolate

A mixture of 15.3 g. (0.05 moles) of ethyl 2'-nitro-4-biophenylylglycolate in 100 ml. methanol containing 0.05 mole citric acid and 1.5 g. of 5% palladium-on-carbon is shaken with hydrogen at 2 atm. pressure and 27°C until 3 moles of hydrogen are absorbed. The mixture is filtered, washed with methanol and the filtrate concentrated in vacuo to obtain ethyl 2'-amino-4-biphenylylglycolate, isolated as the citrate salt.

When ethyl 3-nitro-4-biphenylylglycolate or ethyl 4'-nitro-4-biphenylylglycolate are used in the above example, then the products prepared are ethyl 3-amino-4-biphenylylglycolate or ethyl 4'-amino-4-biphenylylglycolate.

When ethyl α-methyl-2'-nitro-4-biphenylylglycolate, ethyl α-methyl-3-nitro-4-biphenylylglycolate or ethyl α-methyl-4'-nitro-4-biphenylylglycolate are used in the above example then the products prepared are ethyl α-methyl-2'-amino-4-biphenylylglycolate, ethyl α-methyl-3-amino-4-biphenylylglycolate or ethyl α-methyl-4'-amino-4-biphenylylglycolate.

EXAMPLE 9

Ethyl 2'-methylamino-4-biphenylylglycolate

To a solution of 0.01 moles of ethyl 2'-amino-4-biphenylylglycolate in 100 ml. of pyridine is added 0.1 moles of methyl iodide. The reaction mixture is stirred overnight at room temperature, filtered and concentrated. The residue is distilled to obtain ethyl 2'-methylamino-4-biphenylylglycolate.

When 0.01 moles of acetyl chloride is used in place of methyl iodide in the above example, then the product prepared is ethyl 2'-acetylamino-4-biphenylylglycolate.

When ethyl 3-amino-4-biphenylylglycolate or ethyl 4'-amino-4-biphenylylglycolate are used in the above procedures then the products prepared are ethyl 3-methylamino-4-biphenylylglycolate, ethyl 4'-methylamino-4-biphenylylglycolate, ethyl 3-acetylamino-4-biphenylylglycolate or ethyl 4'-acetylamino-4-biphenylylglycolate.

When ethyl α-methyl-2'-amino-4-biophenyllyglycolate, ethyl α-methyl-3-amino-4-biphenylylglycolate or ethyl α-methyl-4'-amino-4 are used in the above procedures then the products prepared are ethyl α-methyl-2'-methylamino-4-biphenylylglycolate, ethyl 60-methyl-3-methylamino-4-biphenylylglycolate, ethyl α-methyl-4'-methylamino-4-biphenylylglycolate, ethyl α-methyl-2'-acetylamino-4-biphenylylglycolate, ethyl α-methyl-3-acetylamino-4-biphenylylglycolate or ethyl α-methyl-4'-acetylamino-4-biphenylylglycolate.

EXAMPLE 10

Ethyl 2'-dimethylamino-4-biphenylylglycolate

A solution of 0.005 moles of ethyl 2'-nitro-4-biphenylylglycolate and 1.6 ml. of 37% formaldehyde in 50 ml. of methanol is shaken with hydrogen over 0.5 g. of 5% palladium-on-charcoal at 42 lbs. and 27°C until five moles of hydrogen are absorbed. The catalyst is filtered off and the filtrate is evaporated in vacuo. The residue is then distilled to obtain ethyl 2'-dimethylamino-4-biphenylylglycolate.

When ethyl 3-nitro-4-biphenylylglycolate or ethyl 4'-nitro-4-biphenylylglycolate are used in the above procedure then the product prepared is ethyl 3-dimethylamino-4-biphenylylglycolate or ethyl 4'-dimethylamino-4-diphenylylglycolate.

When ethyl α-methyl-2'-4-biphenylylglycolate, ethyl α-methyl-3-nitro-4-biphenylylglycolate or ethyl α-methyl-4'-nitro-4-biphenylglycolate are used in the above procedure then the product prepared is ethyl α-methyl-2'-dimethylamino-4-biphenylylglycolate, ethyl α-methyl-3-dimethylamino-4-biphenylylglycolate or ethyl α-methyl-4'-dimethylamino-4-biphenylylglycolate.

EXAMPLE 11

Benzyl 2'-cyano-4-biphenylylglycolate

To 29.4 g. (0.1 moles) of benzyl 2'-amino-4-biphenylylglycolate in 35 ml. of 28% hydrochloric acid and 100 ml. of cracked ice to maintain the temperature at 0°C is added a solution of 7.1 g (0.102 moles) of sodium nitrite in 20 ml. of water. The reaction mixture is then neutralized with sodium carbonate. This diazonium mixture is added to a cuprous cyanide solution (prepared from 31.5 g. of copper sulfate and 16.2 of sodium cyanide in 75 ml. of water). 250 ml. of toluene is also added and the mixture is stirred for ½ hour. The reaction is then allowed to stir an additional 2 hours while warming gradually to 50°C. This is then cooled and the toluene separated, dried over sodium sulfate and evaporated to dryness to obtain benzyl 2'-cyano-4-biphenylylglycolate.

When benzyl 3-amino-4-biphenylylglycolate or benzyl 4'-amino-4-biphenylylglycolate are used in the above procedure then the product prepared is benzyl 3-cyano-4-biphenylylglycolate or benzyl 4'-cyano-4-biphenylylglycolate.

When benzyl α-methyl-2'-amino-4-biphenylylglycolate, benzyl α-methyl-3-amino-4-biphenylylglycolate or benzyl α-methyl-4'-amino-4-biphenylylglycolate are used in the above procedure then the product prepared is benzyl α-methyl-2'-cyano-4-biphenylylglycolate, benzyl α-methyl-3-cyano-4-biphenylylglycolate or benzyl α-methyl-4'-cyano-4-biphenylylglycolate.

EXAMPLE 12

Ethyl 2'-fluoro-4-biphenylylglycolate

To 44.2 g. (0.15 moles) of ethyl 2'-amino-4-biphenylylglycolate is added at 0°C 44 ml. of 1.5 moles of concentrated hydrochloric acid. The reaction mixture is maintained at 0°C and the diazonium salt is prepared with 23.2 g. (0.32 moles) of 95% sodium nitrite in 80 ml. of water. To this mixutre is rapidly added a solution of 10.4 g. (0.17 moles) of boric acid dissolved in 22 g. (0.66 moles) of 60% hydrofluoric acid. The reaction mixture is then stirred for ½ hour and filtered, washed with 3 × 25 ml. of water, 2 × 25 ml. of methanol and 25 ml. of ether. The residual cake is then treated in vacuo. The treated cake is then placed in a distilling flask and heated to permit spontaneous decomposition. After the decomposition, the residue is then fractionally distilled to obtain ethyl 2'-fluoro-4-biphenylylglycolate.

When ethyl 3-amino-4-biphenylglycolate or ethyl 4'-amino-4-biphenylylglycolate are used in the above procedure then the products prepared are ethyl 3-fluoro-4-biphenylylglycolate or ethyl 4'-fluoro-4-biphenylylglycolate.

When ethyl α-methyl-2'-amino-4-biphenylylglycolate, ethyl α-methyl-3-amino-4-biphenylylglycolate or ethyl α-methyl-4'-amino-4-biphenylylglycolate are used in the above procedure then the products prepared are ethyl α-methyl-2'-fluoro-4-biphenylylglycolate, ethyl α-methyl-3-fluoro-4-biphenylylglycolate or ethyl α-methyl-4'-fluoro-4-biphenylylglycolate.

EXAMPLE 13

2'-Hydroxy-4-biphenylylglycolic acid

To 4.5 g. of ethyl 2'-amino-4-biphenylylglycolate supsension in 125 ml. of 80% hydrochloric acid and cooled to 0°C is added dropwise a solution of 1.2 g. of sodium nitrite in 15 ml. of water. After about 10 min., 200 ml. of 50% hydrochloric acid is added portion wise and stirred for 15 hours. The reaction mixture is then poured onto ice water and extracted with chloroform, dried over sodium sulfate and concentrated in vacuo. The residue is crystallized to obtain 3-hydroxy-4-biphenylylglycolic acid.

The ethyl ester of the product is formed by reaction with absolute ethanol containing a small amount of anhydrous hydrochloric acid.

When ethyl 3-amino-4-biphenylylglycolate or ethyl 4'-amino-4-biphenylylglycolate are used in the above procedure then the product prepared is 3-hydroxy-4- biphenylylglycolic acid or 4'-hydroxy-4-biphenylyl-glycolic acid.

EXAMPLE 14

Ethyl 2'-methoxy-4-biphenylylglycolate

To a stirred suspension of 0.01 moles of sodium hydride in 25 ml. of dry dimethylformamide which has been cooled to 0°C is added dropwise a solution of 0.01 moles of ethyl 2'-hydroxy-4-biphenylylglycolate in 10 ml. of dimethylformamide. The reaction mixture is stirred for 15 minutes and 0.015 moles of methyliodide is then added dropwise. The mixture is allowed to stir overnight at room temperature. 200 ml. of water is added and the resulting mixture is extracted well with ether. The ether extract is washed with water, dried over sodium sulfate, evaporated to dryness and distilled to obtain ethyl 2'-methoxy-4-biphenylylglycolate.

When the benzyl ester is used above and 0.01 moles of acetyl chloride is used in place of methyliodide then the product prepared is benzyl 2'-acetyloxy-4-biphenylylglycolate.

When ethyl 3-hydroxy-4-biphenylylglycolate or ethyl 4'-hydroxy-4-biphenylylglycolate are used in the above procedures then the products prepared are ethyl 3-methoxy-4-biphenylylglycolate; ethyl 4'-methoxy-4-biphenylylglycolate; benzyl 3-acetyloxy-4-biophenylylglycolate or benzyl 4'-acetyloxy-4-biphenylylglycolate.

When ethyl α-methyl-2'-hydroxy-4-biphenylylglycolate, ethyl α-methyl-3-hydroxy-4-biphenylylglycolate or ethyl α-methyl-4'-hydroxy-4-biphenylylglycolate are used in the above procedures then the products prepared are ethyl α-methyl-2'-methoxy-4-biphenylylglycolate, ethyl α-methyl-3-methoxy-4-biphenylylglycolate; ethyl α-methyl-4'-methoxy-4-biphenylylglycolate, benzyl α-methyl-2'-acetyloxy-4-biphenylylglycolate, benzyl α-methyl-3-acetyloxy-4-biphenylylglycolate or benzyl α-methyl-4'-acetyloxy-4-biphenylylglycolate.

EXAMPLE 15

2'-Bromo-4-biphenylylglycolic acid

To 11.1 g. (0.044 moles) of ethyl 2'-amino-4-biphenylylglycolate suspension in 225 ml. of 40% hydrobromic acid and cooled to 0°C is added dropwise a solution of 2.34 g. of sodium nitrite in 30 ml. of water. To this mixture is added a solution of 20 g. of cuprous bromide in 350 ml. of 40% hydrobromic acid added portion wise and stirred for 15 hours. The reaction mixture is then poured onto ice water, extracted with chloroform, dried over sodium sulfate and concentrated in vacuo. The residue is then crystallized to obtain 2'-bromo-4-biphenylylglycolic acid.

The ethyl ester of the product is formed by reaction with absolute ethanol containing a small amount of anhydrous hydrochloric acid.

When ethyl 3-amino-4-biphenylylglycolate or ethyl 4'-amino-4-biphenylylglycolate are used in the above procedure then the products prepared are 3-bromo-4-biphenylylglycolic acid or 4'-bromo-4-biphenylyl-glycolic acid.

When ethyl α-methyl-2'-amino-4-biphenylylglycolate, ethyl α-methyl-3-amino-4-biphenylylglycolate or ethyl α-methyl-4'-amino-4-biophenylylglycolate are used in the above procedure then the product prepared are α-methyl-2'-bromo-4-biphenylylglycolic acid, α-methyl-3-bromo-4-biphenylylglycolic acid or α-methyl-4'-bromo-4-biphenylylglycolic acid.

EXAMPLE 16

2'-Iodo-4-biphenylylglycolic acid

To 0.05 moles of ethyl 2'-amino-4-biphenylylglycolate dissolved in a mixture of 50 g. of ice water and .06 moles of concentrated sulfuric acid at 0°c is added a solution of 0.05 moles of 95% sodium nitrite in 8 ml. of water. Stirring is continued for ½ hour and then 1.5 ml. of concentrated sulfuric acid is added. This solution is poured into an ice cold solution of .06 moles of potassium iodide in 10 ml. of water. To this is added 0.075 g. copper bronze with stirring and the solution is warmed slowly on a water bath to about 80°C for 2 hours. After cooling to room temperature the reaction mixture is extracted thrice with 15 ml. portions of chloroform. This is then washed with dilute thiosulfate solution, water, dried over sodium sulfate and evaporated in vacuo. The residue is crystallized to obtain 2'-iodo-4-biphenylylglycolic acid.

The ethyl ester of the product is formed by reaction with absolute ethanol containing a small amount of anhydrous hydrochloric acid.

When ethyl 3-amino-4-biphenylylglycolate or ethyl 4'-amino-4-biphenylylglycolate are used in the above procedure then the product prepared is 3-iodo-4-biphenylylglycolic acid or 4'-iodo-4-biphenylylglycolic acid.

When ethyl α2'-amino-4-biphenylylglycolate, ethyl α-methyl-3-amino-4-biphenylylglycolate or ethyl α-methyl-4'-amino-4-biphenylylglycolate are used in the above procedure then the product prepared is 2'-iodo-4-biphenylylglycolic acid, α-methyl-3-iodo-4-biphenylylglycolic acid or α-methyl-4'-iodo-4-biphenylylglycolic acid.

EXAMPLE 17

2'-Mercapto-4-biphenylylglycolic acid

To 17.3 g. of ethyl 2'-amino-4-biphenylglycolate in 11.1 ml. of concentrated hydrochloric acid and 20 g. of ice is added 4.1 g. of sodium nitrite in 2 ml. of water. This mixture is stirred for 10 min. and then added gradually to an ice cold solution of 10.3 g. of potassium ethyl xanthate in 14 ml. of water. The reaction is gradually heated over 45 min. to 50°C and stirred an additional 45 minutes. The mixture is then cooled, extracted with ether which is then washed with water, dilute sodium hydroxide and water, dried over sodium sulfate and evaporated in vacuo. The residue is dissolved in 35 ml. of boiling ethanol to which is added gradually 13 g. of potassium hydroxide. The reaction is refluxed an additional hour and then evaporated to dryness in vacuo. The residue is dissolved in water and extracted with ether. The alkaline phase is acidified with 6N sulfuric acid and extracted with ether. The ether is washed with water, dried over sodium sulfate and evaporated to dryness to obtain 2'-mercapto-4-biphenylylglycolic acid.

The ethyl ester of the product is formed by reaction with absolute ethanol containing a small amount of anhydrous hydrochloric acid.

When ethyl 3-amino-4-biphenylylglycolate or ethyl 4'-amino-4-biphenylylglycolate are used in the above procedure then the product prepared is 3-mercapto-4-biphenylyglycolic acid or 4'-mercapto-4-biphenyly-glycolic acid.

When ethyl α-methyl-2'-amino-4-biphenylylglycolate, ethyl α-methyl-3-amino-4-biphenylylglycolate or ethyl α-methyl-4'-amino-4-biphenylylglycolate are used in the above procedure then the product prepared is α-methyl-2'-mercapto-4-biphenylylglycolic acid, α-methyl-3-mercapto-4-biphenylylglycolic acid or α-methyl-4'-mercapto-4-biphenylylglycolic acid.

EXAMPLE 18

Ethyl 2'-methylthio-4-biphenylylglycolate

To 3.85 g. of ethyl 2'-mercapto-4-biphenylylglycolate is 40 ml. of water containing 0.65 g. of sodium hydroxide is added 2 ml. of dimethyl sulfate with stirring. The reaction mixture is gradually warmed to 40°C and stirred for 2 hours. The mixture is cooled and extracted with ether which is washed with water, dried and evaporated in vacuo. The residue is distilled to obtain ethyl 2'-methylthio-4-biphenylylglycolate.

When the benzyl ester of 2'-methylthio-4-biphenylylglycolate is treated with 30% $H_2O_2$, then the resultant product is benzyl 2'-methylsulfinyl-4-biphenylylglycolate or benzyl 2'-methysulfonyl-4-biphenylylglycolate.

When an equimolar amount of acetyl chloride is used in place of dimethyl sulfate in the above reaction along with the benzyl ester, then the product prepared in benzyl 2'-acetylthio-4-biphenylylglycolate.

When ethyl 3-mercapto-4-biphenylylglycolate or ethyl 4'-mercapto-4-biphenylylglycolate are used in the above procedure then the products prepared are ethyl 3-methylthio-4-biphenylylglycolate, ethyl 4'-methylthio-4-biphenylylglycolate, benzyl 3-methylsulfinyl-4-biphenylylglycolate, benzyl 4'-methyl-sulfinyl-4-biphenylylglycolate, benzyl 3-methylsulfonyl-4-biphenylylglycolate, benzyl 4'-methylsulfonyl-4-biphenylylglycolate, benzyl 3-acetylthio-4-biphenylylglycolate or benzyl 4'-acetylthio-4-biphenylylglycolate.

When ethyl α-methyl-2'-mercapto-4-biphenylylglycolate, ethyl α-methyl-3-mercapto-4-biphenylylglycolate or ethyl α-methyl-4'-mercapto-4-biphenylylglycolate are used in the above procedures then the products prepared are ethyl α-methyl-2'-methylthio-4-biphenylylglycolate, ethyl α-methyl-3-methylthio-4-biphenylylglycolate, ethyl α-methyl-4'-methylthio-4-biphenylylglycolate, benzyl α-methyl-2'-methylsulfinyl-4-biphenylylgycolate, benzyl α-methyl-3-methylsulfiniyl-4-biphenylylglycolate, benzyl α-methyl-4'-methylsulfinyl-4-biphenyylglycolate, benzyl α-methyl-2'-methylsulfonyl-4-biphenylylglycolate, benzyl α-methyl-3-methylsulfonyl-4-biphenylylglycolate, benzyl α-methyl-4'-methylsulfonyl-4-biphenylylglycolate, benzyl α-methyl-2'-acetylthio-4-biphenylylglycolate, benzyl α-methyl-3-acetylthio-4-biphenylylglycolate or benzyl α-methyl-4'-acetylthio-4-biphenylylglycolate.

EXAMPLE 19

2'-Chloro-4-biphenylylglycolic acid

To a solution of 0.144 moles of ethyl 2'-chloro-4-biphenylylglycolate dissolved in 220 ml. of isopropanol is added 38 g. (0.7 mole) of potassium hydroxide. This mixture is then heated at reflux temperature in a nitrogen atmosphere. The solution is concentrated in vacuo to a viscous oil, which is then dissolved in 500 ml. of water and filtered. The filtrate is acidified with 10% HCl and the precipitate is taken up in ether. The ether layer is dried, filtered and the filtrate concentrated to dryness. Recrystallization of residue from benzene-cyclohexane 1:1 gives 2'-chloro-4-biphenylylglycolic acid.

EXAMPLE 20

When an equimolar amount of the glycolate compounds of Examples 2, 3 and 6 – 18 are used in Example 19, then the corresponding glycolic acid is prepared. A representative list of compounds is shown below.

4-biphenylylglycolic acid
4'-chloro-4-biphenylylglycolic acid
3-chloro-4-biphenylylglycolic acid
4'-bromo-4-biphenylylglycolic acid
2'-bromo-4-biphenylylglycolic acid
3-bromo-4-biphenylylglycolic acid
4'-nitro-4-biphenylyglycolic acid
2'-nitro-4-biphenylylglycolic acid
3-nitro-4-biphenylylglycolic acid
4'-methyl-4-biphenylylglycolic acid
2'-methyl-4-biphenylylglycolic acid
3-methyl-4-biphenylylglycolic acid
4'-trifluoromethyl-4-biphenylylglycolic acid
2'-trifluoromethyl-4-biphenylylglycolic acid
3-trifluoromethyl-4-biphenylylglycolic acid
4'-amino-4-biphenylylglycolic acid
2'-amino-4-biphenylylglycolic acid
3-amino-4-biphenylylglycolic acid
4'-methylamino-4-biphenylylglycolic acid
2'-methylamino-4-biphenylylglycolic acid
3-methylamino-4-biphenylylglycolic acid
4'-dimethylamino-4-biphenylylglycolic acid
2'-dimethylamino-4-biphenylylglycolic acid
3dimethylamino-4-biphenylylglycolic acid
4'-fluoro-4-biphenylylglycolic acid
2'-fluoro-4-biphenylyglycolic acid
3-fluoro-4-biphenylylglycolic acid
4'-hydroxy-4-biphenylylglycolic acid
2'-hydroxy-4-biphenylylglycolic acid
3-hydroxy-4-biphenylylglycolic acid
4'-methoxy-4-biphenylylglycolic acid
2'-methoxy-4-biphenylylglycolic acid
3-methoxy-4-biphenylylglycolic acid
4'-iodo-4-biphenylylglycolic acid
2'-iodo-4-biphenylyglycolic acid
3-iodo-4-biphenylylglycolic acid
4'-mercapto-4-biphenylylglycolic acid
2'-mercapto-4-biphenylylglycolic acid
3-mercapto-4-biphenylylglycolic acid
4'-methylthio-4-biphenylylglycolic acid
2'-methylthio-4-biphenylylglycolic acid
3-methylthio-4-biphenylylglycolic acid
α-methyl-4-biphenylylglycolic acid
α-methyl-4'-chloro-4-biphenylylglycolic acid
α-methyl-3-chloro-4-biphenylylglycolic acid
α-methyl-4'-bromo-4-biphenylylglycolic acid
α-methyl-2'-bromo-4-biphenylylglycolic acid
α-methyl-3-bromo-4-biphenylylglycolic acid
α-methyl-4'-nitro-4-biphenylylglycolic acid
α-methyl-2'-nitro-4-biphenylylglycolic acid
α-methyl-3-nitro-4-biphenylylglycolic acid
α,4'-dimethyl-4-biphenylylglycolic acid
α,2'-dimethyl-4-biphenylylglycolic acid
α,3-dimethyl-4-biphenylylglycolic acid
α-methyl-4'-trifluoromethyl-4-biphenylylglycolic acid
α-methyl-4'-trifluoromethyl-4-biphenylylglycolic acid
α-methyl-2'-trifluoromethyl-4-biphenylylglycolic acid α-methyl-3-trifluoromethyl-4-biphenylylglycolic acid
α-methyl-4'-amino-4-biphenylylglycolic acid
α-methyl-2'-amino-4-biphenylylglycolic acid
α-methyl-3-amino-4-biphenylylglycolic acid
α-methyl-4'-fluoro-4-biphenylylglycolic acid
α-methyl-2'-fluoro-4-biphenylylglycolic acid
α-methyl-3-fluoro-4-biphenylylglycolic acid
α-methyl-4'-mercapto-4-biphenylylglycolic acid
α-methyl-2'-mercapto-4-biphenylylglycolic acid
α-methyl-3-mercapto-4-biphenylylglycolic acid

EXAMPLE 21

2'-Cyano-4-biphenylylglycolic acid

A solution of 0.01 moles of benzyl 2'-cyano-4-biphenylylglycolate dissolved in 100 ml. of acetic acid and containing 0.01 mole of hydrogen chloride is shaken with hydrogen over a 5% Pd carbon catalyst until 0.01 moles of hydrogen is absorbed. The catalyst is then filtered and the solution is evaporated to dryness and crystallized to obtain 2'-cyano-4-biphenylylglycolic acid.

When the benzyl ester used is
benzyl 4'-cyano-4-biphenylylglycolate
benzyl 3-cyano-4-biphenylylglycolate
benzyl 4'-acetylamino-4-biphenylylglycolate
benzyl 2'-acetylamino-4-biphenylylglycolate
benzyl 3-acetylamino-4-biphenylylglycolate
benzyl 4'-acetylthio-4-biphenylylglycolate
benzyl 2'-acetylthio-4-biphenylylglycolate
benzyl 3-acetylthio-4-biphenylylglycolate
benzyl 4'-acetyloxy-4-biphenylylglycolate
benzyl 2'-acetyloxy-4-biphenylylglycolate
benzyl 3-acetyloxy-4-biphenylylglycolate
benzyl 4'-methylsulfinyl-4-biphenylylglycolate
benzyl 2'-methylsulfinyl-4-biphenylylglycolate
benzyl 3-methylsulfinyl-4-biphenylylglycolate
benzyl 4'-methylsulfonyl-4-biphenylylglycolate
benzyl 2'-methylsulfonyl-4-biphenylylglycolate
benzyl 3-methylsulfonyl-4-biphenylylglycolate
benzyl α-methyl-4'-cyano-4-biphenylylglycolate
benzyl α-methyl-3-cyano-4-biphenylylglycolate
benzyl α-methyl-4'-acetylamino-4-biphenylylglycolate
benzyl α-methyl-2'-acetylamino-4-biphenylylglycolate
benzyl α-methyl-3-acetylamino-4-biphenylylglycolate
benzyl α-methyl-4'-acetylthio-4-biphenylylglycolate
benzyl α-methyl-2'-acetylthio-4-biphenylylglycolate
benzyl α-methyl-3-acetylthio-4-biphenylylglycolate
benzyl α-methyl-4'-acetyloxy-4-biphenylylglycolate
benzyl α-methyl-2'-acetyloxy-4-biphenylylglycolate
benzyl α-methyl-3-acetyloxy-4-biphenylylglycolate
benzyl α-methyl-4'-methylsulfinyl-4-biphenylylglycolate
benzyl α-methyl-2'-methylsulfinyl-4-biphenylylglycolate
benzyl α-methyl-3-methylsulfinyl-4-biphenylylglycolate
benzyl α-methyl-4'-methylsulfonyl-4-biphenylylglycolate
benzyl α-methyl-2'-methylsulfonyl-4-biphenylylglycolate
benzyl α-methyl-3-methylsulfonyl-4-biphenylylglycolate
then the products obtained are
4'-cyano-4-biphenylylglycolic acid
3-cyano-4-biphenylylglycolic acid
4'-acetylamino-4-biphenylylglycolic acid
2'-acetylamino-4-biphenylylglycolic acid
3-acetylamino-4-biphenylylglycolic acid
4'-acetylthio-4-biphenylylglycolic acid
2'-acetylthio-4-biphenylylglycolic acid
3-acetylthio-4-biphenylylglycolic acid
4'-acetyloxy-4-biphenylylglycolic acid
2'-acetyloxy-4-biphenylylglycolic acid
3-acetyloxy-4-biphenylylglycolic acid
4'-methylsulfinyl-4-biphenylylglycolic acid
2'-methylsulfinyl-4-biphenylylglycolic acid
3-methylsulfinyl-4-biphenylylglycolic acid
4'-methylsulfonyl-4-biphenylylglycolic acid
2'-methylsulfonyl-4-biphenylylglycolic acid
3-methylsulfonyl-4-biphenylylglycolic acid
α-methyl-4'-cyano-4-biphenylylglycolic acid
α-methyl-2'-cyano-4-biphenylylglycolic acid
α-methyl-3-cyano-4-biphenylylglycolic acid
α-methyl-4'-acetylamino-4-biphenylylglycolic acid
α-methyl-2'-acetylamino-4-biphenylylglycolic acid
α-methyl-3-acetylamino-4-biphenylylglycolic acid
α-methyl-4'-acetylthio-4-biphenylylglycolic acid
α-methyl-2'-acetylthio-4-biphenylylglycolic acid
α-methyl-3-acetylthio-4-biphenylylglycolic acid
α-methyl-4'-acetyloxy-4-biphenylylglycolic acid
α-methyl-2'-acetyloxy-4-biphenylylglycolic acid
α-methyl-3-acetyloxy-4-biphenylylglycolic acid
α-methyl-4'-methylsulfinyl-4-biphenylylglycolic acid
α-methyl-2'-methylsulfinyl-4-biphenylylglycolic acid
α-methyl-3-methylsulfinyl-4-biphenylylglycolic acid
α-methyl-4'-methylsulfonyl-4-biphenylylglycolic acid
α-methyl-2'-methylsulfonyl-4-biphenylylglycolic acid
α-methyl-3-methylsulfonyl-4-biphenylylglycolic acid

EXAMPLE 22 l 2'-Chloro-4-biphenylylglycolic acid

To a boiling solution of 29.4 g. (0.10 mole) of cinchonidine in 1 liter of absolute ethanol is added a boiling solution of 26.9 g. (0.10 mole) of dl 2'-chloro-4-biphenylylglycolic acid in 500 ml. of absolute ethanol. The solution is stirred briefly then allowed to cool to room temperature overnight. The precipitate is collected and washed with 2 × 25 ml. of ethanol and air dried. Recrystallization from isopropanol gives white needle crystals. This material is hydrolyzed with 200 ml. of 1.2 N—HCl. The white solid is collected, washed with 3 × 50 ml. water and dried at 55°C overnight. Recrystallization from benzenecyclohexane 3:2 gives l 2'-chloro-4-biphenylylglycolic acid.

When modifications of the above resolution procedure is followed but dl 2'-chloro-4-cyclohexylphenylglycolic acid is replaced by an equimolar amount of the dl glycolic acids of Examples 19 – 21, then the corresponding l-isomer is prepared.

EXAMPLE 23 d 2'-Chloro-4-biphenylylglycolic acid

The combined ethanol and isopropanol filtrates from Example 22 are evaporated to dryness. This material is triturated with 1 liter of boiling acetone. The material which does not go into solution is filtered off. The filtrate is evaporated to dryness and hydrolyzed with 100 ml. of 1.2 N—HCl. The precipitate is collected, washed with 3 × 25 ml. of water, and dried at 55°C. Recrystallization from benzene-cyclohexane 3:2 gives d 2'-chloro-4-biphenylylglycolic acid.

When modifications of the above resolution procedure is followed but dl 2'-chloro-4-biphenylylglycolic acid is replaced by an equimolar amount of the dl glycolic acids of Examples 19 – 21, then the corresponding d-isomer is prepared.

EXAMPLE 24

2'-Chloro-4-biphenylylglycolic acid, sodium salt

A solution of 12.4 g. of sodium bicarbonate in 135 ml. of water is added dropwise to a stirred solution of 44.1 g. (0.164 moles) of 2'-chloro-4-biphenylylglycolic acid in 150 ml. of methanol. The solvent is removed in vacuo and the residue is dried by repeated distillations with anhydrous ethanol. The crystalline residue is triturated with ether (100 ml.), collected and washed with ether. The residue is dried in a vacuum desiccator to obtain 2'-chloro-4-biphenylylglycolic acid, sodium salt.

When an equimolar amount of sodium bicarbonate in the above reaction is replaced by the compounds of Table I below, then the corresponding salt of Table II below is prepared.

Table I sodium hydroxide
potassium hydroxide
calcium hydroxide
potassium carbonate
magnesium bicarbonate Table II 2'-chloro-4-biphenylylglycolic acid, sodium salt
2'-chloro-4-biphenylylglycolic acid, potassium salt
2'-chloro-4-biphenylylglycolic acid, calcium salt
2'-chloro-4-biphenylylglycolic acid, magnesium salt When the dl, d and l glycolic acid compounds of this invention are used in the above reaction, the corresponding salt is prepared.

EXAMPLE 25

2'-Chloro-4-biphenylylglycolic acid, diethylammonium salt

Anhydrous diethylamine (0.11 moles) is added dropwise to a stirred solution of 2'-chloro-4-biphenylylglycolic acid (0.10 moles) in 100 ml. of n-hexane at 0°C. The precipitated diethylammonium salt is collected on a filter washed with n-hexane and dried in a vacuum desiccator to obtain 2'-chloro-4-biphenylylglycolic acid, diethylammonium salt.

When diethylamine in the above reaction is replaced by an equimolar amount of the compounds of Table I, below, then the corresponding product of Table II, below is prepared.

Table I dimethylamine
α-methylbenzylamine
β-hydroxyethylamine
cyclohexylamine
piperazine
triethylamine
piperidine
phenethylamine Table II 2'-chloro-4-biphenylylglycolic acid, dimethylammonium salt
2'-chloro-4-biphenylylglycolic acid, β-hydroxyethylammonium salt
2'-chloro-4-biphenylylglycolic acid, piperazinium salt
2'-chloro-4-biphenylylglycolic acid, piperidinium salt
2'-chloro-4-biphenylylglycolic acid, α-methylbenzylammonium salt
2'-chloro-4-biphenylylglycolic acid, cyclohexylammonium salt
2'-chloro-4-biphenylylglycolic acid, triethylammonium salt
2'-chloro-4-biphenylylglycolic acid, phenethylammonium salt When the dl, d and l glycolic acids of this invention are used in the above reaction, then the corresponding salt is prepared.

EXAMPLE 26

N-isopropyl 2'-chloro-4-biphenylylglycolamide

Ethyl 2'-chloro-4-biphenylylglycolate 29.48 g. (0.1 mole) is stirred with 20 ml. of isopropylamine at about 35°C with stirring overnight and the temperature is then raised to reflux for 28 hours. The reaction mixture is evaporated in vacuo and the residue distilled to obtain N-isopropyl 2'-chloro-4-biphenylylglycolamide.

When isopropylamine in the above reaction is replaced by an equimolar amount of the compound of Table I, below then the corresponding product of Table II below is prepared.

Table I diethylamine
isothiazolidine
ethylmethylamine
piperidine
t-butylamine
morpholine
cyclopropylamine
N-methylpiperazine
N-methylhomopiperazine Table II N,N-diethyl-2'-chloro-4-biphenylylglycolamide
n-methyl-N-ethyl-2'-chloro-4-biphenylylglycolamide
N-t-butyl-2'-chloro-4-biphenylylglycolamide
N-cyclopropyl-2'-chloro-4-biphenylylglycolamide
N,N-pentamethylene-2'-chloro-4-biphenylylglycolamide
N,N-oxydiethylene-2'-chloro-4-biphenylylglycolamide
N,N-methylaminodiethylene-2'-chloro-4-biphenylylglycolamide
N,N-methylaminoethylenetrimethylene-2'-chloro-4-biphenylylglycolamide
N,N-thiotrimethylene-2'-chloro-4-biphenylylglycolamide When isopropylamine in the above reaction is replaced by ammonia, methylamine or dimethylamine and the reaction carried out in a bomb at 150°C, then the product prepared is 2'-chloro-4-biphenylylglycolamide, N-methyl-2'-chloro-4-biphenylylglycolamide or N,N-dimethyl-2'-chloro-4-biphenylylglycolamide.

When the dl, d or l glycolic acids of this invention are used in the above reaction, then the corresponding amide is prepared.

EXAMPLE 27

Ethyl α,2'-dichloro-4-biphenylylacetate

A mixture of 221.75 g. (0.747 mole) of ethyl 2'- chloro-4-biphenylylglycolate is stirred with 106.67 g. (0.895 mole) of thionyl chloride at room temperature for 24 hours and then heated to reflux for 6 hours. The cold reaction mixture is poured into 1125 ml. of ice-cold water with stirring. The mixture is extracted with 800 ml. of ether. The ethereal solution is washed with 450 ml. of cold saturated sodium hydrocarbonate solution followed by washing twice, each time with 250 ml. of cold water. The ethereal solution is dried over anhydrous sodium sulfate and filtered. The solvent is removed in vacuo to obtain ethyl α,2'-chloro-4-biphenylylacetate.

EXAMPLE 28

When the procedure of Example 27 is followed but ethyl 2'-chloro-4-biphenylylglycolate is replaced by the dl, d and l glycolates of this invention, then the corresponding dl, d and l α-chloroacetate products are prepared. A representative list of compounds obtained is shown below.

ethyl α-chloro-4-biphenylylacetate
ethyl α,4'-dichloro-4-biphenylylacetate
ethyl α,3-dichloro-4-biphenylylacetate
ethyl α-chloro-4'-bromo-4-biphenylylacetate
ethyl α-chloro-2'-bromo-4-biphenylylacetate
ethyl α-chloro-3-bromo-4-biphenylylacetate
ethyl α-chloro-4'-nitro-4-biphenylylacetate
ethyl α-chloro-2'-nitro-4-biphenylylacetate
ethyl α-chloro-3-nitro-4-biphenylylacetate
ethyl α-chloro-4'-methyl-4-biphenylylacetate
ethyl α-chloro-2'-methyl-4-biphenylylacetate
ethyl α-chloro-3-methyl-4-biphenylylacetate
ethyl α-chloro-4'-trifluoromethyl-4-biphenylylacetate
ethyl α-chloro-2'-trifluoromethyl-4-biphenylylacetate
ethyl α-chloro-3-trifluoromethyl-4-biphenylylacetate
ethyl α-chloro-4'-amino-4-biphenylylacetate
ethyl α-chloro-2'-amino-4-biphenylylacetate
ethyl α-chloro-3-amino-4-biphenylylacetate
ethyl α-chloro-4'-fluoro-4-biphenylylacetate
ethyl α-chloro-2'-fluoro-4-biphenylylacetate
ethyl α-chloro-3-fluoro-4-biphenylylacetate
ethyl α-chloro-4'-hydroxy-4-biphenylylacetate
ethyl α-chloro-2'-hydroxy-4-biphenylylacetate
ethyl α-chloro-3-hydroxy-4-biphenylylacetate
ethyl α-chloro-4'-methoxy-4-biphenylylacetate
ethyl α-chloro-2'-methoxy-4-biphenylylacetate
ethyl α-chloro-3-methoxy-4-biphenylylacetate
ethyl α-chloro-4'-iodo-4-biphenylylacetate
ethyl α-chloro-2'-iodo-4-biphenylylacetate
ethyl α-chloro-3-iodo-4-biphenylylacetate
ethyl α-chloro-4'-mercapto-4-biphenylylacetate
ethyl α-chloro-2'-mercapto-4-biphenylylacetate
ethyl α-chloro-3-mercapto-4-biphenylylacetate
ethyl α-chloro-4'-methylthio-4-biphenylylacetate
ethyl α-chloro-2'-methylthio-4-biphenylylacetate
ethyl α-chloro-3-methylthio-4-biphenylylacetate
benzyl α-chloro-4'-cyano-4-biphenylylacetate
benzyl α-chloro-2'-cyano-4-biphenylylacetate
benzyl α-chloro-3-cyano-4-biphenylylacetate
benzyl α-chloro-4'-acetylamino-4-biphenylylacetate
benzyl α-chloro-2'-acetylamino-4-biphenylylacetate
benzyl α-chloro-3-acetylamino-4-biphenylylacetate
benzyl α-chloro-4'-acetylthio-4-biphenylylacetate
benzyl α-chloro-2'-acetylthio-4-biphenylylacetate
benzyl α-chloro-3-acetylthio-4-biphenylylacetate
benzyl α-chloro-4'-acetyloxy-4-biphenylylacetate
benzyl α-chloro-2'-acetyloxy-4-biphenylylacetate
benzyl α-chloro-3-acetyloxy-4-biphenylylacetate
benzyl α-chloro-4'-methylsulfinyl-4-biphenylylacetate
benzyl α-chloro-2'-methylsulfinyl-4-biphenylylacetate
benzyl α-chloro-3-methylsulfinyl-4-biphenylylacetate
benzyl α-chloro-4'-methylsulfonyl-4-biphenylylacetate
benzyl α-chloro-2'-methylsulfonyl-4-biphenylylacetate
benzyl α-chloro-3-methylsulfonyl-4-biphenylylacetate
ethyl α-methyl-α,4'-dichloro-4-biphenylylacetate
ethyl α-methyl-α,2'-dichloro-4-biphenylylacetate
ethyl α-methyl-α,3-dichloro-4-biphenylylacetate
ethyl α-methyl-α-chloro-4'-bromo-4-biphenylylacetate
ethyl α-methyl-α-chloro-2'-bromo-4-biphenylylacetate
ethyl α-methyl-α-chloro-3-bromo-4-biphenylylacetate
ethyl α-methyl-α-chloro-4'-nitro-4-biphenylylacetate
ethyl α-methyl-α-chloro-2'-nitro-4-biphenylylacetate
ethyl α-methyl-α-chloro-3-nitro-4-biphenylylacetate
ethyl α-chloro-α,4'-dimethyl-4-biphenylylacetate
ethyl α-chloro-α,2'-dimethyl-4-biphenylylacetate
ethyl α-chloro-α,3-dimethyl-4-biphenylylacetate
ethyl α-chloro-α-methyl-4'-trifluoromethyl-4-biphenylylacetate
ethyl α-chloro-α-methyl-2'-trifluoromethyl-4-biphenylylacetate
ethyl α-chloro-α-methyl-3-trifluoromethyl-4-biphenylylacetate
ethyl α-chloro-α-methyl-4'-amino-4-biphenylylacetate
ethyl α-chloro-α-methyl-2'-amino-4-biphenylylacetate
ethyl α-chloro-α-methyl-3-amino-4-biphenylylacetate
ethyl α-chloro-α-methyl-4'-fluoro-4-biphenylylacetate
ethyl α-chloro-α-methyl-2'-fluoro-4-biphenylylacetate
ethyl α-chloro-α-methyl-3-fluoro-4-biphenylylacetate
ethyl α-chloro-α-methyl-4'-mercapto-4-biphenylylacetate
ethyl α-chloro-α-methyl-2'-mercapto-4-biphenylylacetate
ethyl α-chloro-α-methyl-3-mercapto-4-biphenylylacetate
benzyl α-chloro-α-methyl-4'-cyano-4-biphenylylacetate
benzyl α-chloro-α-methyl-2'-cyano-4-biphenylylacetate
benzyl α-chloro-α-methyl-3-cyano-4-biphenylylacetate
benzyl α-chloro-α-methyl-4'-acetylamino-4-biphenylylacetate
benzyl α-chloro-α-methyl-2'-acetylamino-4-biphenylylacetate
benzyl α-chloro-α-methyl-3-acetylamino-4-biphenylylacetate
benzyl α-chloro-α-methyl-4'-acetylthio-4-biphenylylacetate
benzyl α-chloro-α-methyl-2'-acetylthio-4-biphenylylacetate
benzyl α-chloro-α-methyl-3-acetylthio-4-biphenylyllacetate
benzyl α-chloro-α-methyl-4'-acetyloxy-4-biphenylylacetate
benzyl α-chloro-α-methyl-2'-acetyloxy-4-biphenylylacetate
benzyl α-chloro-α-methyl-3-acetyloxy-4-biphenylylacetate
benzyl α-chloro-α-methyl-4'-methylsulfinyl-4-biphenylylacetate
benzyl α-chloro-α-methyl-2'-methylsulfinyl-4-biphenylylacetate
benzyl α-chloro-α-methyl-3-methylsulfinyl-4-biphenylylacetate
benzyl α-chloro-α-methyl-4'-methylsulfonyl-4-biphenylylacetate
benzyl α-chloro-α-methyl-2'-methylsulfonyl-4-biphenylylacetate
benzyl α-chloro-α-methyl-3-methylsulfonyl-4-biphenylylacetate

EXAMPLE 29

When the procedure of Example 27 is followed but ethyl 2'-chloro-4-biphenylylglycolate is replaced by the amides of Example 26, then the corresponding α-chloroacetamide product is prepared.

N-methyl α,2'-dichloro-4-biphenylylacetamide
N,N-dimethyl α,2'-dichloro-4-biphenylylacetamide
N-isopropyl α,2'-dichloro-4-biphenylylacetamide
N,N-diethyl α,2'-dichloro-4-biphenylylacetamide
N-methyl-N-ethyl α,2'-dichloro-4-biphenylylacetamide
N-t-butyl α,2'-dichloro-4-biphenylylacetamide
N-cyclopropyl α,2'-dichloro-4-biphenylylacetamide
N,N-pentamethylene α,2'-dichloro-4-biphenylylacetamide
N,N-oxydiethylene α,2'-dichloro-4-biphenylylacetamide
N,N-methylaminodiethylene α,2'-dichloro-4-biphenylylacetamide
N,N-methylaminoethylenetrimethylene α,2'-dichloro-4-biphenylylacetamide
N,N-thiotrimethylene α,2'-dichloro-4-biphenylylacetamide When the dl, d and l glycolamides of this invention are used in the above reaction, then the corresponding amide is prepared.

EXAMPLE 30

α,2'-Dichloro-4-biphenylylacetic acid

A mixture of 52.5 g. (0.167 moles) of ethyl α,2'-dichloro-4-biphenylylacetate and 160 ml. of glacial acetic acid containing 40 ml. of 37% hydrochloric acid is refluxed for 20 hours. The mixture is concentrated under reduced pressure to give a gummy residue. The latter material is dissolved in 300 ml. of n-hexane, washed with ice-cold water (100 ml. total), dried over sodium sulfate and filtered. The hexane is removed to give α,2'-dichloro-4-biphenylylacetic acid.

EXAMPLE 31

When the procedure of Example 30 is followed but ethyl α,2'-dichloro-4-biphenylylacetate is replaced by the dl, d and l α-chloroacetates of this invention, then the corresponding dl, d and l α-chloroacetic acids are prepared. A representative list of products obtained is shown below.

α-chloro-4-biphenylylacetic acid
α,4'-dichloro-4-biphenylylacetic acid
α,3-dichloro-4-biphenylylacetic acid
α-chloro-4'-bromo-4-biphenylylacetic acid
α-chloro-2'-bromo-4-biphenylylacetic acid
α-chloro-3-bromo-4-biphenylylacetic acid
α-chloro-4'-nitro-4-biphenylylacetic acid
α-chloro-2'-nitro-4-biphenylylacetic acid
α-chloro-3-nitro-4-biphenylylacetic acid
α-chloro-4'-methyl-4-biphenylylacetic acid
α-chloro-2'-methyl-4-biphenylylacetic acid
α-chloro-3-methyl-4-biphenylylacetic acid
α-chloro-4'-trifluoromethyl-4-biphenylylacetic acid
α-chloro-2'-trifluoromethyl-4-biphenylylacetic acid
α-chloro-3-trifluoromethyl-4-biphenylylacetic acid
α-chloro-4'-amino-4-biphenylylacetic acid
α-chloro-2'-amino-4-biphenylylacetic acid
α-chloro-3-amino-4-biphenylylacetic acid
α-chloro-4'-fluoro-4-biphenylylacetic acid
α-chloro-2'-fluoro-4-biphenylylacetic acid
α-chloro-3-fluoro-4-biphenylylacetic acid
α-chloro-4'-hydroxy-4-biphenylylacetic acid
α-chloro-2'-hydroxy-4-biphenylylacetic acid
α-chloro-3-hydroxy-4-biphenylylacetic acid
α-chloro-4'-methoxy-4-biphenylylacetic acid
α-chloro-2'-methoxy-4-biphenylylacetic acid
α-chloro-3-methoxy-4-biphenylylacetic acid
α-chloro-4'-iodo-4-biphenylylacetic acid
α-chloro-2'-iodo-4-biphenylylacetic acid
α-chloro-3-iodo-4-biphenylylacetic acid
α-chloro-4'-mercapto-4-biphenylylacetic acid
α-chloro-2'-mercapto-4-biphenylylacetic acid
α-chloro-3-mercapto-4-biphenylylacetic acid
α-chloro-4'-methylthio-4-biphenylylacetic acid
α-chloro-2'-methylthio-4-biphenylylacetic acid
α-chloro-3-methylthio-4-biphenylylacetic acid
α-chloro-4'-cyano-4-biphenylylacetic acid
α-chloro-2'-cyano-4-biphenylylacetic acid
α-chloro-3-cyano-4-biphenylylacetic acid
α-chloro-4'-acetylamino-4-biphenylylacetic acid
α-chloro-2'-acetylamino-4-biphenylylacetic acid
α-chloro-3-acetylamino-4-biphenylylacetic acid
α-chloro-4'-acetylthio-4-biphenylylacetic acid
α-chloro-2'-acetylthio-4-biphenylylacetic acid
α-chloro-3-acetylthio-4-biphenylylacetic acid
α-chloro-4'-acetyloxy-4-biphenylylacetic acid
α-chloro-2'-acetyloxy-4-biphenylylacetic acid
α-chloro-3-acetyloxy-4-biphenylylacetic acid
α-chloro-4'-methylsulfinyl-4-biphenylylacetic acid
α-chloro-2'-methylsulfinyl-4-biphenylylacetic acid
α-chloro-3-methylsulfinyl-4-biphenylylacetic acid
α-chloro-4'-methylsulfonyl-4-biphenylylacetic acid
α-chloro-2'-methylsulfonyl--4-biphenylylacetic acid
α-chloro-3-methylsulfonyl-4-biphenylylacetic acid
α-methyl-α,4'-dichloro-4-biphenylylacetic acid
α-methyl-α,2'-dichloro-4-biphenylylacetic acid
α-methyl-α,3-dichloro-4-biphenylylacetic acid
α-methyl-α-chloro-4'-bromo-4-biphenylylacetic acid
α-methyl-α-chloro-2'-bromo-4-biphenylylacetic acid
α-methyl-α-chloro-3-bromo-4-biphenylylacetic acid
α-methyl-α-chloro-4'-nitro-4-biphenylylacetic acid
α-methyl-α-chloro-2'-nitro-4-biphenylylacetic acid
α-methyl-α-chloro-3-nitro-4-biphenylylacetic acid
α-chloro-α,4'-dimethyl-4-biphenylylacetic acid
α-chloro-α,2'-dimethyl-4-biphenylylacetic acid
α-chloro-α,3-dimethyl-4-biphenylylacetic acid
α-chloro-α-methyl-4'-trifluoromethyl-4-biphenylylacetic acid
α-chloro-α-methyl-2'-trifluoromethyl-4-biphenylylacetic acid
α-chloro-α-methyl-3-trifluoromethyl-4-biphenylylacetic acid α-chloro-α-methyl-4'-amino-4-biphenylylacetic acid
α-chloro-α-methyl-2'-amino-4-biphenylylacetic acid
α-chloro-α-methyl-3-amino-4-biphenylylacetic acid
α-chloro-α-methyl-4'-fluoro-4-biphenylylacetic acid
α-chloro-α-methyl-2'-fluoro-4-biphenylylacetic acid
α-chloro-α-methyl-3-fluoro-4-biphenylylacetic acid
α-chloro-α-methyl-4'-mercapto-4-biphenylylacetic acid
α-chloro-α-methyl-2'-mercapto-4-biphenylylacetic acid
α-chloro-α-methyl-3-mercapto-4-biphenylylacetic acid
α-chloro-α-methyl-4'-cyano-4-biphenylylacetic acid
α-chloro-α-methyl-2'-cyano-4-biphenylylacetic acid
α-chloro-α-methyl-3-cyano-4-biphenylylacetic acid
α-chloro-α-methyl-4'-acetylamino-4-biphenylylacetic acid
α-chloro-α-methyl-2'-acetylamino-4-biphenylylacetic acid
α-chloro-α-methyl-3-acetylamino-4-biphenylylacetic acid
α-chloro-α-methyl-4'-acetylthio-4-biphenylylacetic acid
α-chloro-α-methyl-2'-acetylthio-4-biphenylylacetic acid
α-chloro-α-methyl-3-acetylthio-4-biphenylylacetic acid
α-chloro-α-methyl-4'-acetyloxy-4-biphenylylacetic acid
α-chloro-α-methyl-2'-acetyloxy-4-biphenylylacetic acid
α-chloro-α-methyl-3-acetyloxy-4-biphenylylacetic acid
α-chloro-α-methyl-4'-methylsulfinyl-4-biphenylylacetic acid
α-chloro-α-methyl-2'-methylsulfinyl-4-biphenylylacetic acid
α-chloro-α-methyl-3-methylsulfinyl-4-biphenylylacetic acid
α-chloro-α-methyl-4'-methylsulfonyl-4-biphenylylacetic acid
α-chloro-α-methyl-2'-methylsulfonyl-4-biphenylylacetic acid
α-chloro-α-methyl-3-methylsulfonyl-4-biphenylylacetic acid

EXAMPLE 32

α,2'-Dichloro-4-biphenylylacetic acid, sodium salt

A solution of 12.4 g. of sodium bicarbonate in 135 ml. water is added dropwise to a stirred solution of 47.1 g. (0.164 moles) of α,2'-dichloro-4-biphenylylacetic acid in 150 cc. of methanol. The solvent is removed in vacuo and the residue is dried by repeated distillations with anhydrous ethanol. The crystalline residue is triturated with ether (100 cc.), collected on a filter, and washed with ether. Drying in a vacuum desiccator affords α,2'-dichloro-4-biphenylylacetic acid, sodium salt.

When a equimolar amount of sodium bicarbonate in the above reaction is replaced by the compounds of Table I below, then the corresponding salt of Table II below is prepared.

Table I
sodium hydroxide
potassium hydroxide
calcium hydroxide
potassium carbonate
magnesium bicarbonate Table II
α,2'-dichloro-4-biphenylylacetic acid, sodium salt
α,2'-dichloro-4-biphenylylacetic acid, potassium salt
α,2'-dichloro-4-biphenylylacetic acid, calcium salt
α,2'-dichloro-4-biphenylylacetic acid, magnesium salt When the dl, d and l α-chloroacetic acid compounds of this invention are used in the above reaction, the corresponding salt is prepared.

EXAMPLE 33

α,2'-Dichloro-4-biphenylylacetic acid, diethylammonium salt

Anhydrous diethylamine (0.11 moles) is added dropwise to a stirred solution of α,2'-dichloro-4-biphenylylacetic acid (0.10 moles) in 100 ml. of n-hexane at 0°C. The precipitate is collected on a filter, washed with n-hexane, and dried in a vacuum desiccator to obtain α,2'-dichloro-4-biphenylylacetic acid, diethylammonium salt.

When diethylamine in the above reaction is replaced by an equimolar amount of the compounds of Table I, below, then the corresponding product of Table II, below is prepared.

Table I
dimethylamine
β-hydroxyethylamine
piperazine
piperidine
α-methylbenzylamine
cyclohexylamine
triethylamine
phenethylamine Table II
α,2'-dichloro-4-biphenylylacetic acid, dimethylammonium salt
α,2'-dichloro-4-biphenylylacetic acid, β-hydroxyethylammonium salt
α,2'-dichloro-4-biphenylylacetic acid, piperazinium salt
α,2'-dichloro-4-biphenylylacetic acid, piperidinium salt
α,2'-dichloro-4-biphenylylacetic acid, α-methylbenzylammonium salt
α,2'-dichloro-4-biphenylylacetic acid, cyclohexylammonium salt
α,2'-dichloro-4-biphenylylacetic acid, triethylammonium salt
α,2'-dichloro-4-biphenylylacetic acid, phenethylammonium salt

EXAMPLE 34

N-isopropyl α,2'-Dichloro-4-biphenylyacetamide

A mixture of 5 g. (0.016 moles) of ethyl α,2'-dichloro-4-biphenylylacetate and 5.5 ml. of anhydrous isopropylamine are stirred over Linde 4A molecular sieve for 16 hours at room temperature. The reaction mixture is taken up in ether and washed 3 times with 15 ml. of 10% hydrochloric acid. The ether layer is dried over sodium sulfate, filtered, and the ether is removed. The residue is triturated with n-hexane and the precipitate is collected to obtain N-isopropyl α,2'-dichloro-4-biphenylylacetamide.

When isopropylamine in the above reaction is replaced by an equimolar amount of the compound of Table I, below then the corresponding product of Table II below is prepared.

Table I diethylamine
ethylmethylamine
t-butylamine
cyclopropylamine
isothiazolidine
piperidine
morpholine
N-methylpiperazine
N-methylhomopiperazine Table II N,N-diethyl-α,2'-dichloro-4-biphenylylacetamide
N-methyl-N-ethyl-α,2'-dichloro-4-biphenylylacetamide
N-t-butyl-α,2'-dichloro-4-biphenylylacetamide
N-cyclopropyl-α,2'-dichloro-4-biphenylylacetamide
N,N-pentamethylene-α,2'-dichloro-4-biphenylylacetamide
N,N-oxydiethylene-α,2'-dichloro-4-biphenylylacetamide
N,N-methylaminodiethylene-α,2'-dichloro-4-biphenylylacetamide
N,N-methylaminoethylenetrimethylene-α,2'-dichloro-4-biphenylylacetamide
N,N-thiotrimethylene-α,2'-dichloro-4-biphenylylacetamide When isopropylamine in the above reaction is replaced by ammonia, methylamine or dimethylamine and the reaction carried out in a bomb at 150°C, then the product prepared is α,2'-dichloro-4-biphenylylacetamide, N-methyl-α,2'-dichloro-4-biphenylylacetamide or N,N-dimethyl-α,2'-dichloro-4-biphenylylacetamide.

When the dl, d or l α-chloroacetates of this invention are used in the above reaction, then the corresponding amide is prepared.

EXAMPLE 35

Ethyl α-bromo-2'-chloro-4-biphenylylacetate

To 15.0 g. (0.0476 moles) of ethyl 2'-chloro-4-biphenylylglycolate there is added slowly with stirring at 40°–50°C 23 g. (0.053 moles) of phosphorus pentabromide. The mixture is stirred at room temperature for 16 hours, then diluted with 70 ml. of petroleum ether, and poured into 125 ml. of ice-cold water. The organic phase is separated, washed with saturated aqueous sodium hydrogen carbonate solution, dried over anhydrous sodium sulfate, filtered and the solvent removed in vacuo to obtain ethyl α-bromo-2'-chloro-4-biphenylylacetate.

When ethyl 2'-chloro-4-biphenylylglycolate in the above procedure is replaced by d ethyl 2'-chloro-4-biphenylylglycolate, l ethyl 2'-chloro-4-biphenylylglycolate or N-isopropyl 2'-chloro-4-biphenylylglycolamide, then the products prepared are d ethyl α-bromo-2'-chloro-4-biphenylylglycolate, l ethyl α-bromo-2'-chloro-4-biphenylylglycolate or N-isopropyl α-bromo-2'-chloro-4-biphenylylglycolamide.

When the above procedure is followed using the various glycolates and glycolamides of this invention, then the corresponding α-bromoacetates and α-bromoacetamides are prepared.

EXAMPLE 36

When the α-bromoacetates of Example 35 are hydrolyzed according to the procedures of Examples 30–31, then the corresponding dl, d and l α-bromo-2'-chloro-4-biphenylylacetic acid compounds and the various α-bromoacetic acids are prepared.

EXAMPLE 37

When the α-bromoacetic acid compounds are reacted according to the procedures of Examples 32–33, then the corresponding α-bromoacetic acid salts are prepared.

EXAMPLE 38

Ethyl α-fluoro-2'-chloro-4-biphenylylacetate

A mixture of 118 g. (0.33 moles) ethyl α-bromo-2'-chloro-4-biphenylylacetate is vigorously stirred at 130°–140°C with 29 g. (0.5 moles) of potassium fluoride in 100 ml. of ethylene glycol for 12 hours. The reaction mixture is cooled and 400 ml. of water is added and the crude product separates. The aqueous glycol mixture is extracted with ether, the ether is then dried, evaporated to dryness and upon distillation results in ethyl α-fluoro-2'-chloro-4-biphenylylacetate.

When ethyl α-bromo-2'-chloro-4-biphenylylacetate in the above procedure is replaced by d ethyl α-bromo-2'-chloro-4-biphenylylacetate, l ethyl α-bromo-2'-chloro-4-biphenylylacetate or N-isopropyl α-bromo-2'-chloro-4-biphenylylacetamide, then the products prepared are d ethyl α-fluoro-2'-chloro-4-biphenylylacetate, l ethyl α-fluoro-2'-chloro-4-biphenylylacetate or N-isopropyl-α-fluoro-2'-chloro-4-biphenylylacetamide.

When the above procedure is followed using the various α-bromoacetates and α-bromacetamides of this invention, then the corresponding α-fluoroacetates and α-fluoroacetamides are prepared.

EXAMPLE 39

When the α-fluoroacetates of Example 38 are hydrolyzed according to the procedures of Examples 30–31, then the corresponding dl, d and l α-fluoro-2'-chloro-4-biphenylylacetic acid compounds and the various α-fluoroacetic acids are prepared.

EXAMPLE 40

When the α-fluoroacetic acid compounds are reacted according to the procedures of Example 32–33, then the corresponding α-fluoroacetic acid salts are prepared.

EXAMPLE 41

Ethyl α-iodo-3-chloro-4-cyclohexylphenylacetate

A mixture of 40.5 g. (0.1 moles) of ethyl α-bromo-2'-chloro-4-biphenylylacetate and 150 g. of sodium iodide in 1 liter of anhydrous acetone is refluxed for 4 hours. The reaction mixture is then evaporated to dryness and extracted with ether. The ether is then washed with water, dried and evaporated to dryness to obtain ethyl α-iodo-2'-chloro-4-biphenylylacetate.

When ethyl α-bromo-2'-chloro-4-biphenylylacetate in the above procedure is replaced by d ethyl α-bromo-2'-chloro-4-biphenylylacetate, l ethyl α-bromo-2'-chloro-4-biphenylylacetate of N-isopropyl α-bromo-2'-chloro-4-biphenylylacetamide, then the products prepared are d ethyl α-iodo-2'-chloro-4-biphenylylacetate, l ethyl α-iodo-2'-chloro-4-biphenylylacetate or N-isopropyl α-iodo-2'-chloro-4-biphenylylacetamide.

When the above procedure is followed using the various α-bromacetates and α-bromacetamides of this invention, then the corresponding α-iodoacetates and α-iodacetamides are prepared.

EXAMPLE 42

When the α-iodoacetates of Example 41 are hydrolyzed according to the procedures of Examples 30–31, then the corresponding α-iodo-2'-chloro-4-biphenylylacetic acid compound and the various α-iodoacetic acids are prepared.

EXAMPLE 43

When the α-iodoacetic acid compounds are reacted according to the procedures of Examples 32–33, then the corresponding α-iodoacetic acid salts are prepared.

EXAMPLE 44

α-Mercapto-2'-chloro-4-biphenylylacetic acid

A mixture of 14 g. (.05 moles) of α,2'-dichloro-4-biphenylylacetic acid and 5 g. of sodium hydrosulfide in 100 ml. of absolute ethanol and under a nitrogen atmosphere is stirred for 15 hours. The mixture is then acidified with 6 N hydrochloric acid. The solvent is removed in vacuo and the residue is extracted into ether, washed with water, saturated sodium chloride solution, dried and evaporated to dryness to obtain α-mercapto-2'-chloro-4-biphenylylacetic acid.

When the α-chloroacetic acid, α-chloroacetates and α-chloroacetamides of this invention are used in the above reaction, then the corresponding α-mercaptoacetic acids, α-mercaptoacetates and α-mercaptoacetamides are prepared.

EXAMPLE 45

α-Methylthio-2'-chloro-4-biphenylylacetic acid

Methyl mercaptan is bubbled into a solution of 18.4 g. of potassium t-butoxide in 100 ml. of t-butanol for 3/4 hours and under a nitrogen atmosphere. To this is added 12 g. (0.041 moles) of α,2'-dichloro-4-biphenylylacetic acid in 60 ml of dry tetrahydrofuran. The mixture is then refluxed for 3 hours and allowed to stir at room temperature for 15 hours, acidified with 30 ml of 6 N hydrochloric acid. The solvent is removed in vacuo and the residue extracted into ether, washed with water, saturated sodium chloride solution, dried and evaporated to dryness to obtain α-methylthio-2'-chloro-4-biphenylylacetic acid.

When the α-chloroacetic acids, α-chloroacetates and α-chloroacetamides of this invention are used in the above reaction, then the corresponding α-methylthioacetic acids, α-methylthioacetates and α-methylthioacetamides are prepared.

EXAMPLE 46

α-Acetythio-2'-chloro-4-biphenylylacetic acid

To a solution of 600 ml. of anhydrous ethanol and 21 g. (0.317 moles) of potassium hydroxide is added 45 ml. of thioacetic acid dropwise. To this mixture is then added 70 g. (0.244 moles) of α,2'-dichloro-4-biphenylylacetic acid and stirring is continued for 15 hours. The solid which forms is filtered off and washed with ethanol. The filtrate is evaporated to dryness and the residue is dissolved in 500 ml. of ether and washed several times with water. Drying the ether and evaporation to dryness results in α-acetylthio-2'-chloro-4-biphenylylacetic acid.

In a similar manner, the α-propionylthio-2'-chloro-4-biphenylylacetic acid compounds are prepared.

When the α-chloroacetic acids, α-chloroacetates and α-chloroacetamides of this invention are used in the above reaction, then corresponding α-acetylthioacetic acids, α-acetylthioacetates and α-acetylthioacetamides are prepared.

EXAMPLE 47

α-Benzoylthio-2'-chloro-4-biphenylylacetic acid

To 17.5 ml. of 2N alcoholic potassium hydroxide solution (0.035 mole) is added 4.84 g. (0.035 mole) of thiobenzoic acid. The solution is cooled to room temperature and to this is added in small portions 10.05 g. (0.035 mole) of α,2'-dichloro-4-biphenylylacetic acid. The reaction mixture is stirred at room temperature for 25 hours, then the solvent is removed, the residue dissolved in ether, filtered and washed with cold water. The ethereal solution is then dried over magnesium sulfate and evaporated to dryness to obtain α-benzoylthio-2'-chloro-4-biphenylylacetic acid.

When the α-chloroacetic acid, α-chloroacetates and α-chloroacetamides of this invention are used in the above reaction, then the corresponding α-benzoylthioacetic acids, α-benzoylthioacetates and α-benzoylthioacetamides are prepared.

EXAMPLE 48

Ethyl α-thioacetylthio-2'-chloro-4-biphenylylacetate

A mixture of 0.2 moles of sodium dithioacetate and 38 g. (0.12 moles) of ethyl α,2'-dichloro-4-biphenylylacetate in 300 ml. of absolute ethanol is stirred at room temperature for 15 hours. The reaction mixture is filtered, washed with absolute ethanol and evaporated to dryness in vacuo. The residue is treated with ether, filtered and evaporated to dryness to obtain ethyl α-thioacetylthio-2'-chloro-4-biphenylylacetate.

When the α-chloroacetic acids, α-chloroacetates and α-chloroacetamides of this invention are used in the above reaction, then the corresponding α-thioacetylthioacetic acids, α-thioacetylthioacetates and α-thioacetylthioacetamides are prepared.

When sodium dithioformate is used in the above procedure in place of sodium dithioacetate then the product prepared is ethyl α-thioformylthio-2'-chloro-4-biphenylylacetate.

EXAMPLE 49

α-Thiocyanato-2'-chloro-4-biphenylylacetic acid

To a solution of 300 ml. of anhydrous ethanol and 0.15 moles of sodium thiocyanate is added 35 g. (0.12 moles) of α,2'-dichloro-4-biphenylylacetic acid and stirred for 15 hours. The reaction mixture is filtered and washed with absolute ethanol. The filtrate is evaporated to dryness, the residue is dissolved in 250 ml. of ether and washed several times with water. The ether is then dried and evaporated to dryness to obtain α-thiocyanato-2'-chloro-4-biphenylylacetic acid.

When the α-chloroacetic acids, α-chloroacetate and α-chloroacetamides of this invention are used in the above reaction, then the corresponding α-thiocyanatoacetic acids, α-thiocyanatoacetates and α-thiocyanatoacetamides are prepared.

EXAMPLE 50

α-Sulfo-2'-chloro-4-biphenylylacetic acid, disodium salt

To a solution of 250 ml. of anhydrous ethanol and 0.12 moles of sodium sulfite is added 29 g. (0.1 moles)

of α,2'-dichloro-4-biphenylylacetic acid, sodium salt. The reaction mixture is stirred for 15 hours, filtered and the residue worked with ethanol. The filtrate is evaporated to dryness to obtain α-sulfo-2'-chloro-4-biphenylylacetic acid, disodium salt.

When sodium sulfinate is used in the above procedure in place of sodium sulfite then the product obtained is α-sulfino-2'-chloro-4-biphenylylacetic acid, disodium salt.

When the α-chloroacetates and α-chloroacetamides of this invention are used in the above reactions, then the corresponding α-sulfo and α-sulfinoacetates and amides are prepared.

EXAMPLE 51

Ethyl α-thiosulfo-2'-chloro-4-biphenylylacetate, sodium salt

A mixture of 7.2 g. (.023 moles) of ethyl α,2'-dichloro-4-biphenylylacetate and 5.7 g. of sodium thiosulfate pentahydrate in 75 ml. of 40:45 water-alcohol mixture is refluxed for 2 hours. An additional 0.8 g. of sodium thiosulfate pentahydrate is then added and refluxing continued another ½ hour. The reaction mixture is then evaporated to dryness in vacuo, azeotroped with ethanol and evaporated to dryness in vacuo again. The residue is triturated with ether, filtered and evaporated to dryness. The residue is then triturated with hexane and the resultant gum is dissolved in alcohol and evaporated to dryness in vacuo to obtain ethyl α-thiosulfo-2'-chloro-4-biphenylylacetate, sodium salt.

When the α-chloroacetates and α-chloroacetamides of this invention are used in the above reaction, then the corresponding α-thiosulfoacetates and α-thiosulfoacetamides are prepared.

EXAMPLE 52

α-Amidinothio-2'-chloro-4-biphenylylacetic acid, hydrochloride

Thiourea 15.2 g. (0.2 moles) is dissolved in 150 ml. of absolute ethanol and to this is added 31.6 g. (0.11 moles) of α,2'-dichloro-4-biphenylylacetic acid. The mixture is stirred for 15 hours at 0°C. The mixture is then filtered to obtain α-amidinothio-2'-chloro-4-biphenylylacetic acid, hydrochloride.

When the α-chloroacetic acids, esters and amides of this invention are used in the above procedures then the corresponding α-amidinoacetic acids, esters and amides are prepared.

EXAMPLE 53

α-Ethoxythiocarbamylthio-2'-chloro-4-biphenylylacetic acid

Ethylxanthic acid, potassium salt, 3.63 g. (0.22 moles) is dissolved in 150 ml. of absolute ethanol with stirring. To this solution is added 3.16 g. (0.11 moles) of α,2'-dichloro-4-biphenylylacetic acid and the mixture stirred for 15 hours. The solid which collects is separated and washed with absolute ethanol. The solid is then treated with acetone and the insoluble material filtered off. The filtrate is concentrated to dryness to obtain α-ethoxythiocarbamylthio-2'-chloro-4-biphenylylacetic acid.

When the α-chloroacetic acids, esters and amides of this invention are used in the above procedure then the corresponding α-ethylxanthylacetic acids, esters and amides are prepared.

EXAMPLE 54

α-Ethoxycarbonylthio-2'-chloro-4-biphenylylacetic acid

A solution of α-mercapto-2'-chloro-4-biphenylylacetic acid 5.6 g. (0.02 moles) in 25 ml. of pyridine is cooled in an ice bath. To this is added dropwise 2.1 ml. (0.022 moles) of ethyl chloroformate. The mixture is basified with 10% sodium bicarbonate solution. The alkaline mixture is worked with ether, then acidified with 10% hydrochloric acid, washed with ether, dried and filtered. The solvent is removed and the residue is triturated with hexane to obtain α-ethoxycarbonylthio-2'-chloro-4-biphenylylacetic acid.

When the α-mercaptoacetic acids, esters and amides of this invention are used in the above procedure then the corresponding α-ethoxycarbonylthioacetic acids, esters and amides are prepared.

EXAMPLE 55

α-Diethylcarbamylthio-2'-chloro-4-biphenylylacetic acid

A solution of α-mercapto-2'-chloro-4-biphenylylacetic acid 5.6 g. (0.2 moles) in 25 ml. of pyridine is cooled in an ice bath. To this is added dropwise 0.022 moles of diethylcarbamyl chloride. The mixture is then stirred for 2 hours, diluted with ether and filtered. The mixture is then basified with 10% sodium bicarbonate solution. The alkaline mixture is washed with ether, acidified with 10% hydrochloric acid, extracted with ether which in turn is washed with cold water, dried and evaporated to dryness. Trituration with hexane results in α-diethylcarbamylthio-2'-chloro-4-biphenylylacetic acid.

When diethylcarbamylchloride is replaced in the above procedure by carbamyl chloride (prepared in situ from potassium cyanate and anhydrous hydrogen chloride in anhydrous chloroform), ethylcarbamyl chloride or dimethylcarbamyl chloride, then the products prepared are α-carbamylthio2'-chloro-4-biphenylylacetic acid, α-ethylcarbamylthio-2'-chloro-4-biphenylylacetic acid or α-dimethylcarbamylthio-2'-chloro-4-biphenylylacetic acid.

When the α-mercaptoacetic acids, acid, esters and amides of this invention are used in the above procedure then the corresponding α-carbamylthioacetic acids, esters and amides are prepared.

EXAMPLE 56

When the procedure of Example 66 is followed but diethylcarbonate is replaced by succinic anhydride, maleic anhydride or phthalic anhydride, then the products prepared are α-butyrylthio-2'-chloro-4-biphenylylacetic acid, α-butenoylthio-2'-chloro-4-biphenylylacetic acid and α-(τ-carboxybenzoylthio)-2'-chloro-4-biphenylylacetic acid.

When the various α-mercaptoacetic acids, esters and amides of this invention are used in the above procedure, then the corresponding product is obtained.

EXAMPLE 57

When α-methylthio-2'-chloro-4-biphenylylacetic acid is treated with 30% hydrogen peroxide, then the resultant product is α-methylsulfinyl-2'-chloro-4-biphenylylacetic acid or α-methylsulfonyl-2'-chloro-4-biphenylylacetic acid.

EXAMPLE 58

When the procedures of Examples 1–57 are followed but using the starting materials below, then the corresponding products are obtained.

| STARTING MATERIAL | PRODUCT | EXAMPLE |
|---|---|---|
| α-chloro-2'-fluoro-4-biphenylylacetic acid | α-acetylthio-2'-fluoro-4-biphenylylacetic acid | 46 |
| α-chloro-2'-bromo-4-biphenylylacetic acid | α-acetylthio-2'-bromo-4-biphenylylacetic acid | 46 |
| α-chloro-2'-iodo-4-biphenylylacetic acid | α-acetylthio-2'-iodo-4-biphenylylacetic acid | 46 |
| α-chloro-2'-nitro-4-biphenylylacetic acid | α-acetylthio-2'-nitro-4-biphenylylacetic acid | 46 |
| α-chloro-2'-trifluoromethyl-4-biphenylylacetic acid | α-acetylthio-2'-trifluoromethyl-4-biphenylylacetic acid | 46 |
| α-chloro-2'-mercapto-4-biphenylylacetic acid | α-acetylthio-2'-mercapto-4-biphenylylacetic acid | 46 |
| α-chloro-2'-acetylthio-4-biphenylylacetic acid | α-acetylthio-2'-acetylthio-4-biphenylylacetic acid | 46 |
| α-chloro-2'-methylmercapto-4-biphenylylacetic acid | α-acetylthio-2'-methylmercapto-4-biphenylylacetic acid | 46 |
| α-chloro-2'-methylsulfinyl-4-biphenylylacetic acid | α-acetylthio-2'-methylsulfinyl-4-biphenylylacetic acid | 46 |
| α-chloro-2'-methylsulfonyl-4-biphenylylacetic acid | α-acetylthio-2'-methylsulfonyl-4-biphenylylacetic acid | 46 |
| α-chloro-2'-cyano-4-biphenylylacetic acid | α-acetylthio-2'-cyano-4-biphenylylacetic acid | 46 |
| α-chloro-2'-amino-4-biphenylylacetic acid | α-acetylthio-2'-amino-4-biphenylylacetic acid | 46 |
| α-chloro-2'-acetylamino-4-biphenylylacetic acid | α-acetylthio-2'-acetylamino-4-biphenylylacetic acid | 46 |
| α-chloro-2'-methylamino-4-biphenylylacetic acid | α-acetylthio-2'-methylamino-4-biphenylylacetic acid | 46 |
| α-chloro-2'-dimethylamino-4-biphenylylacetic acid | α-acetylthio-2'-dimethylamino-4-biphenylylacetic acid | 46 |
| α-chloro-2'-hydroxy-4-biphenylylacetic acid | α-acetylthio-2'-hydroxy-4-biphenylylacetic acid | 46 |
| α-chloro-2'-acetyloxy-4-biphenylylacetic acid | α-acetylthio-2'-acetyloxy-4-biphenylylacetic acid | 46 |
| α-chloro-2'-methoxy-4-biphenylylacetic acid | α-acetylthio-2'-methoxy-4-biphenylylacetic acid | 46 |
| α-chloro-2'-acetoxy-4-biphenylylacetic acid | α-acetylthio-2'-acetoxy-4-biphenylylacetic acid | 46 |
| α-chloro-2'-methyl-4-biphenylylacetic acid | α-acetylthio-2'-methyl-4-biphenylylacetic acid | 46 |
| α,3-dichloro-4-biphenylylacetic acid | α-acetylthio-3-chloro-4-biphenylylacetic acid | 46 |
| α-chloro-3-fluoro-4-biphenylylacetic acid | α-acetylthio-3-fluoro-4-biphenylylacetic acid | 46 |
| α-chloro-3-bromo-4-biphenylylacetic acid | α-acetylthio-3-bromo-4-biphenylylacetic acid | 46 |
| α-chloro-3-nitro-4-biphenylylacetic acid | α-acetylthio-3-nitro-4-biphenylylacetic acid | 46 |
| α-chloro-3-trifluoromethyl-4-biphenylylacetic acid | α-acetylthio-3-trifluoromethyl-4-biphenylylacetic acid | 46 |
| α-chloro-3-cyano-4-biphenylylacetic acid | α-acetylthio-3-cyano-4-biphenylylacetic acid | 46 |
| α-chloro-3-methylsulfonyl-4-biphenylylacetic acid | α-acetylthio-3-methylsulfonyl-4-biphenylylacetic acid | 46 |
| α,4'-dichloro-4-biphenylylacetic acid | α-acetylthio-4'-chloro-4-biphenylylacetic acid | 46 |
| α-chloro-4'-fluoro-4-biphenylylacetic acid | α-acetylthio-4'-fluoro-4-biphenylylacetic acid | 46 |
| α-chloro-4'-bromo-4-biphenylylacetic acid | α-acetylthio-4'-bromo-4-biphenylylacetic acid | 46 |
| α-chloro-4'-nitro-4-biphenylylacetic acid | α-acetylthio-4'-nitro-4-biphenylylacetic acid | 46 |
| α-chloro-4'-trifluoromethyl-4-biphenylylacetic acid | α-acetylthio-4'-trifluoromethyl-4-biphenylylacetic acid | 46 |
| α-chloro-4'-cyano-4-biphenylylacetic acid | α-acetylthio-4'-cyano-4-biphenylylacetic acid | 46 |
| α-chloro-4'-methylsulfonyl-4-biphenylylacetic acid | α-acetylthio-4'-methylsulfonyl-4-biphenylylacetic acid | 46 |
| α-chloro-α-methyl-2'-fluoro-4-biphenylylacetic acid | α-acetylthio-α-methyl-2'-fluoro-4-biphenylylacetic acid | 46 |
| α,2'-dichloro-α-methyl-4-biphenylylacetic acid | α-acetylthio-α-methyl-2'-chloro-4-biphenylylacetic acid | 46 |
| α-chloro-α-methyl-2'-bromo-4-biphenylylacetic acid | α-acetylthio-α-methyl-2'-bromo-4-biphenylylacetic acid | 46 |
| α-chloro-α-methyl-2'-nitro-4-biphenylylacetic acid | α-acetylthio-α-methyl-2'-nitro-4-biphenylylacetic acid | 46 |
| α-chloro-α-methyl-2'-trifluoromethyl-4-biphenylylacetic acid | α-acetylthio-α-methyl-2'-trifluoromethyl-4-biphenylylacetic acid | 46 |
| α-chloro-α-methyl-2'-cyano-4-biphenylylacetic acid | α-acetylthio-α-methyl-2'-cyano-4-biphenylylacetic acid | 46 |
| α-chloro-α-methyl-2'-methylsulfonyl-4-biphenylylacetic acid | α-acetylthio-α-methyl-2'-methylsulfonyl-4-biphenylylacetic acid | 46 |
| α-chloro-α-methyl-3-fluoro-4-biphenylylacetic acid | α-acetylthio-α-methyl-3-fluoro-4-biphenylylacetic acid | 46 |
| α,3-dichloro-α-methyl-4-biphenylylacetic acid | α-acetylthio-α-methyl-3-chloro-4-biphenylylacetic acid | 46 |
| α-chloro-α-methyl-3-bromo-4-biphenylylacetic acid | α-acetylthio-α-methyl-3-bromo-4-biphenylylacetic acid | 46 |
| α-chloro-α-methyl-3-trifluoromethyl-4-biphenylylacetic acid | α-acetylthio-α-methyl-3-trifluoromethyl-4-biphenylylacetic acid | 46 |
| α-chloro-α-methyl-3-cyano-4-biphenylylacetic acid | α-acetylthio-α-methyl-3-cyano-4-biphenylylacetic acid | 46 |
| α-chloro-α-methyl-3-methylsulfonyl-4-biphenylylacetic acid | α-acetylthio-α-methyl-3-methylsulfonyl-4-biphenylylacetic acid | 46 |
| α-chloro-α-methyl-4'-fluoro-4-biphenylylacetic acid | α-acetylthio-α-methyl-4'-fluoro-4-biphenylylacetic acid | 46 |
| α,4'-dichloro-α-methyl-4-biphenylylacetic acid | α-acetylthio-4'-chloro-α-methyl-4-biphenylylacetic acid | 46 |
| α-chloro-α-methyl-4'-bromo-4-biphenylylacetic acid | α-acetylthio-α-methyl-4'-bromo-4-biphenylylacetic acid | 46 |
| α-chloro-α-methyl-4'-nitro-4-biphenylylacetic acid | α-acetylthio-α-methyl-4'-nitro-4-biphenylylacetic acid | 46 |
| α-chloro-α-methyl-4'-trifluoromethyl-4-biphenylylacetic acid | α-acetylthio-α-methyl-4'-trifluoromethyl-4-biphenylylacetic acid | 46 |
| α-chloro-α-methyl-4'-cyano-4-biphenylylacetic acid | α-acetylthio-α-methyl-4'-cyano-4-biphenylylacetic acid | 46 |
| α-chloro-α-methyl-4'-methylsulfonyl-4-biphenylylacetic acid | α-acetylthio-α-methyl-4'-methylsulfonyl-4-biphenylylacetic acid | 46 |
| α-chloro-2'-fluoro-4-biphenylylacetic acid | α-mercapto-2'-fluoro-4-biphenylylacetic acid | 44 |
| α-chloro-2'-bromo-4-biphenylylacetic acid | α-propionylthio-2'-bromo-4-biphenylylacetic acid | 46 |
| α-chloro-2'-nitro-4-biphenylylacetic acid | α-butyrylthio-2'-nitro-4-biphenylylacetic acid | 44,56 |
| α-chloro-2'-trifluoromethyl-4-biphenylylacetic acid | α-butenoythio-2'-trifluoromethyl-4-biphenylylacetic acid | 44,56 |
| α-chloro-2'-cyano-4-biphenylylacetic acid | α-benzoylthio-2'-cyano-4-biphenylylacetic acid | 47 |
| α-chloro-2'-dimethylsulfonyl-4-biphenylylacetic acid | α,2'-dimethylsulfonyl-4-biphenylylacetic acid | 45,57 |
| α-chloro-3-fluoro-4-biphenylylacetic acid | α-methylthio-3-fluoro-4-biphenylylacetic acid | 45 |
| α,3-dichloro-4-biphenylylacetic acid | α-diethylcarbamylthio-3-chloro-4-biphenylylacetic acid | 44,55 |
| α-chloro-3-bromo-4-biphenylylacetic acid | α-ethylcarbamylthio-3-bromo-4-biphenylylacetic acid | 44,55 |
| α-chloro-3-nitro-4-biphenylylacetic acid | α-i-propylthio-3-nitro-4-biphenylylacetic acid | 45 |
| α-chloro-3-trifluoromethyl-4-biphenylylacetic acid | α-thiosulfo-3-trifluoromethyl-4-biphenylylacetic acid | 51 |
| α-chloro-3-cyano-4-biphenylylacetic acid | α-thiocyanato-3-cyano-4-biphenylylacetic acid | 49 |
| α-chloro-4'-fluoro-4-biphenylylacetic acid | α-benzoylthio-4'-fluoro-4-biphenylylacetic acid | 47 |
| α,4'-dichloro-4-biphenylylacetic acid | α-benzoylthio-4'-chloro-4-biphenylylacetic acid | 47 |
| α-chloro-4'-bromo-4-biphenylylacetic acid | α-benzoylthio-4'-bromo-4-biphenylylacetic acid | 47 |
| α-chloro-4'-nitro-4-biphenylylacetic acid | α-sulfino-4'-nitro-4-biphenylylacetic acid | 50 |
| α-chloro-4'-trifluoromethyl-4-biphenylylacetic acid | α-sulfo-4'-trifluoromethyl-4-biphenylylacetic acid | 50 |
| α-chloro-4'-cyano-4-biphenylylacetic acid | α-amidinothio-4'-cyano-4-cyclohexylphenylacetic acid | 52 |
| α-chloro-α-methyl-2'-fluoro-4-biphenylylacetic acid | α-benzyloxycarbonylthio-α-methyl-2'-fluoro-4-biphenylylacetic acid | 44,54 |
| α,2'-dichloro-α-methyl-4-biphenylylacetic acid | α-methylsulfinyl-α-methyl-2'-chloro-4-biphenylylacetic acid | 45,57 |
| α,2'-dichloro-4-biphenylylacetic acid | α-methylsulfonyl-2'-chloro-4-biphenylylacetic acid | 45,57 |
| α,2'-dichloro-4-biphenylylacetic acid | α-(σ-carboxybenzoylthio)-2'-chloro-4-biphenylylacetic acid | 44,56 |
| α,2'-dichloro-4-biphenylylacetic acid | α-(σ-carboxybenzoylthio)-2'-chloro-4-biphenylylacetic acid | 44,56 |
| α,2'-dichloro-4-biphenylylacetic acid | α-thiosulfo-2'-chloro-4-biphenylylacetic acid | 51 |
| α,2'-dichloro-4-biphenylylacetic acid | α-methylsulfonyl-2'-chloro-4-biphenylylacetic acid | 45,57 |
| methyl α,2'-dichloro-4-biphenylylacetate | methyl α-acetylthio-2'-chloro-4-biphenylylacetate | 46 |
| ethyl α,2'-dichloro-4-biphenylylacetate | ethyl α-acetyltio-2'-chloro-4-biphenylylacetate | 46 |
| benzyl α,2'-dichloro-4-biphenylylacetate | benzyl α-acetyltio-2'-chloro-4-biphenylylacetate | 46 |

-continued

| STARTING MATERIAL | PRODUCT | EXAMPLE |
|---|---|---|
| N-methyl α,2'-dichloro-4-biphenylylacetamide | N-methyl α-acetylthio-2'-chloro-4-biphenylylacetamide | 46 |
| N,N-dimethyl α,2'-dichloro-4-biphenylylacetamide | N,N-dimethyl α-acetylthio-2'-chloro-4-biphenylylacetamide | 46 |
| N,N-diethyl α,2'-dichloro-4-biphenylylacetamide | N,N-diethyl α-acetylthio-2'-chloro-4-biphenylylacetamide | 46 |
| N,N-ethylmethyl α,2'-dichloro-4-biphenylylacetamide | N,N-ethylmethyl α-acetylthio-2'-chloro-4-biphenylylacetamide | 46 |
| N-isopropyl α,2'-dichloro-4-biphenylylacetamide | N-isopropyl α-acetylthio-2'-chloro-4-biphenylylacetamide | 46 |
| N-cyclopropyl α,2'-dichloro-4-biphenylylacetamide | N-cyclopropyl α-acetylthio-2'-chloro-4-biphenylylacetamide | 46 |
| N,N-pentamethylene α,2'-dichloro-4-biphenylylacetamide | N,N-pentamethylene α-acetylthio-2'-chloro-4-biphenylylacetamide | 46 |
| N,N-oxydiethylene α,2'-dichloro-4-biphenylylacetamide | N,N-oxydiethylene α-acetylthio-2'-chloro-4-biphenylylacetamide | 46 |
| N,N-methylaminoethylenetrimethylene α,2'-dichloro-4-biphenylylacetamide | N,N-methylaminoethylenetrimethylene α-acetyltio-2'-chloro-4-biphenylylacetamide | 46 |
| N,N-thiotrimethylene α,2'-dichloro-4-biphenylylacetamide | N,N-thiotrimethylene α-acetylthio-2'-chloro-4-biphenylylacetamide | 46 |
| α-acetylthio-2'-chloro-4-biphenylylacetic acid | α-acetylthio-2'-chloro-4-biphenylylacetic acid, sodium salt | 32 |
| α-acetylthio-2'-chloro-4-biphenylylacetic acid | α-acetylthio-2'-chloro-4-biphenylylacetic acid, potassium salt | 32 |
| α-acetylthio-2'-chloro-4-biphenylylacetic acid | α-acetylthio-2'-chloro-4-biphenylylacetic acid, calcium salt | 32 |
| α-acetylthio-2'-chloro-4-biphenylylacetic acid | α-acetylthio-2'-chloro-4-biphenylylacetic acid, aluminum salt | 32 |
| α-acetylthio-2'-chloro-4-biphenylylacetic acid | α-acetylthio-2'-chloro-4-biphenylylacetic acid, dimethylammonium salt | 33 |
| α-acetylthio-2'-chloro-4-biphenylylacetic acid | α-acetylthio-2'-chloro-4-biphenylylacetic acid, diethylammonium salt | 33 |
| α-acetylthio-2'-chloro-4-biphenylylacetic acid | α-acetylthio-2'-chloro-4-biphenylylacetic acid, β-hydroxyethylammonium salt | 33 |
| α-acetylthio-2'-chloro-4-biphenylylacetic acid | α-acetylthio-2'-chloro-4-biphenylylacetic acid, piperazinium salt | 33 |
| α-acetylthio-2'-chloro-4-biphenylylacetic acid | α-acetylthio-2'-chloro-4-biphenylylacetic acid, piperidinium salt | 33 |
| α-acetylthio-2'-chloro-4-biphenylylacetic acid | α-acetylthio-2'-chloro-4-biphenylylacetic acid, α-methylbenzylammonium salt | 33 |
| α-acetylthio-2'-fluoro-4-biphenylylacetic acid | d α-acetylthio-2'-fluoro-4-biphenylylacetic acid | 23 |
| α-acetylthio-2'-fluoro-4-biphenylylacetic acid | l α-acetylthio-2'-fluoro-4-biphenylylacetic acid | 22 |
| α-acetylthio-2'-chloro-4-biphenylylacetic acid | d α-acetylthio-2'-chloro-4-biphenylylacetic acid | 23 |
| α-acetylthio-2'-chloro-4-biphenylylacetic acid | l α-acetylthio-2'-chloro-4-biphenylylacetic acid | 22 |
| α-acetylthio-2'-bromo-4-biphenylylacetic acid | d α-acetylthio-2'-bromo-4-biphenylylacetic acid | 23 |
| α-acetylthio-2'-bromo-4-biphenylylacetic acid | l α-acetylthio-2'-bromo-4-biphenylylacetic acid | 22 |
| α-acetylthio-2'-nitro-4-biphenylylacetic acid | d α-acetylthio-2'-nitro-4-biphenylylacetic acid | 23 |
| α-acetylthio-2'-nitro-4-biphenylylacetic acid | l α-acetylthio-2'-nitro-4-biphenylylacetic acid | 22 |
| α-acetylthio-2'-trifluoromethyl-4-biphenylylacetic acid | d α-acetylthio-2'-trifluoromethyl-4-biphenylylacetic acid | 23 |
| α-acetylthio-2'-trifluoromethyl-4-biphenylylacetic acid | l α-acetylthio-2'-trifluoromethyl-4-biphenylylacetic acid | 22 |
| α-acetylthio-2'-cyano-4-biphenylylacetic acid | d α-acetylthio-2'-cyano-4-biphenylylacetic acid | 23 |
| α-acetylthio-2'-cyano-4-biphenylylacetic acid | l α-acetylthio-2'-cyano-4-biphenylylacetic acid | 22 |
| α-acetylthio-2'-methylsulfonyl-4-biphenylylacetic acid | d α-acetylthio-2'-methylsulfonyl-4-biphenylylacetic acid | 23 |
| α-acetylthio-2'-methylsulfonyl-4-biphenylylacetic acid | l α-acetylthio-2'-methylsulfonyl-4-biphenylylacetic acid | 22 |
| α-acetylthio-3-fluoro-4-biphenylylacetic acid | d α-acetylthio-3-fluoro-4-biphenylylacetic acid | 23 |
| α-acetylthio-3-fluoro-4-biphenylylacetic acid | l α-acetylthio-3-fluoro-4-biphenylylacetic acid | 22 |
| α-acetylthio-3-chloro-4-biphenylylacetic acid | d α-acetylthio-3-chloro-4-biphenylylacetic acid | 23 |
| α-acetylthio-3-chloro-4-biphenylylacetic acid | l α-acetylthio-3-chloro-4-biphenylylacetic acid | 22 |
| α-acetylthio-3-bromo-4-biphenylylacetic acid | d α-acetylthio-3-bromo-4-biphenylylacetic acid | 23 |
| α-acetylthio-3-bromo-4-biphenylylacetic acid | l α-acetylthio-3-bromo-4-biphenylylacetic acid | 22 |
| α-acetylthio-3-nitro-4-biphenylylacetic acid | d α-acetylthio-3-nitro-4-biphenylylacetic acid | 23 |
| α-acetylthio-3-nitro-4-biphenylylacetic acid | l α-acetylthio-3-nitro-4-biphenylylacetic acid | 22 |
| α-acetylthio-3-trifluoromethyl-4-biphenylylacetic acid | d α-acetylthio-3-trifluoromethyl-4-biphenylylacetic acid | 23 |
| α-acetylthio-3-trifluoromethyl-4-biphenylylacetic acid | l α-acetylthio-3-trifluoromethyl-4-biphenylylacetic acid | 22 |
| α-acetylthio-3-cyano-4-biphenylylacetic acid | d α-acetylthio-3-cyano-4-biphenylylacetic acid | 23 |
| α-acetylthio-3-cyano-4-biphenylylacetic acid | l α-acetylthio-3-cyano-4-biphenylylacetic acid | 22 |
| α-acetylthio-3-methylsulfonyl-4-biphenylylacetic acid | d α-acetylthio-3-methylsulfonyl-4-biphenylylacetic acid | 23 |
| α-acetylthio-3-methylsulfonyl-4-biphenylylacetic acid | l α-acetylthio-3-methylsulfonyl-4-biphenylylacetic acid | 22 |
| α-acetylthio-4'-fluoro-4-biphenylylacetic acid | d α-acetylthio-4'-fluoro-4-biphenylylacetic acid | 23 |
| α-acetylthio-4'-fluoro-4-biphenylylacetic acid | l α-acetylthio-4'-fluoro-4-biphenylylacetic acid | 22 |
| α-acetylthio-4'-chloro-4-biphenylylacetic acid | d α-acetylthio-4'-chloro-4-biphenylylacetic acid | 23 |
| α-acetylthio-4'-chloro-4-biphenylylacetic acid | l α-acetylthio-4'-chloro-4-biphenylylacetic acid | 22 |
| α-acetylthio-4'-bromo-4-biphenylylacetic acid | d α-acetylthio-4'-bromo-4-biphenylylacetic acid | 23 |
| α-acetylthio-4'-bromo-4-biphenylylacetic acid | l α-acetylthio-4'-bromo-4-biphenylylacetic acid | 22 |
| α-acetylthio-4'-nitro-4-biphenylylacetic acid | d α-acetylthio-4'-nitro-4-biphenylylacetic acid | 23 |
| α-acetylthio-4'-nitro-4-biphenylylacetic acid | l α-acetylthio-4'-nitro-4-biphenylylacetic acid | 22 |
| α-acetylthio-4'-trifluoromethyl-4-biphenylylacetic acid | d α-acetylthio-4'-trifluoromethyl-4-biphenylylacetic acid | 23 |
| α-acetylthio-4'-trifluoromethyl-4-biphenylylacetic acid | l α-acetylthio-4'-trifluoromethyl-4-biphenylylacetic acid | 22 |
| α-acetylthio-4'-cyano-4-biphenylylacetic acid | d α-acetylthio-4'-cyano-4-biphenylylacetic acid | 23 |
| α-acetylthio-4'-cyano-4-biphenylylacetic acid | l α-acetylthio-4'-cyano-4-biphenylylacetic acid | 22 |
| α-acetylthio-4'-methylsulfonyl-4-biphenylylacetic acid | d α-acetylthio-4'-methylsulfonyl-4-biphenylylacetic acid | 23 |
| α-acetylthio-4'-methylsulfonyl-4-biphenylylacetic acid | l α-acetylthio-4'-methylsulfonyl-4-biphenylylacetic acid | 22 |
| α-mercapto-2'-chloro-4-biphenylylacetic acid | d α-mercapto-2'-chloro-4-biphenylylacetic acid | 23 |
| α-mercapto-2'-chloro-4-biphenylylacetic acid | l α-mercapto-2'-chloro-4-biphenylylacetic acid | 22 |
| α-butyrylthio-2'-nitro-4-biphenylylacetic acid | d α-butyrylthio-2'-nitro-4-biphenylylacetic acid | 23 |
| α-butyrylthio-2'-nitro-4-biphenylylacetic acid | l α-butyrylthio-2'-nitro-4-biphenylylacetic acid | 22 |
| α-diethylcarbamylthio-3-chloro-4-biphenylylacetic acid | d α-diethylcarbamylthio-3-chloro-4-biphenylylacetic acid | 23 |
| α-diethylcarbamylthio-3-chloro-4-biphenylylacetic acid | l α-diethylcarbamylthio-3-chloro-4-biphenylylacetic acid | 22 |
| α-i-propylthio-3-nitro-4-biphenylylacetic acid | d α-i-propylthio-3-nitro-4-biphenylylacetic acid | 23 |
| α-i-propylthio-3-nitro-4-biphenylylacetic acid | l α-i-propylthio-3-nitro-4-biphenylylacetic acid | 22 |
| α-propionylthio-4'-chloro-4-biphenylylacetic acid | d α-propionylthio-4'-chloro-4-biphenylylacetic acid | 23 |
| α-propionylthio-4'-chloro-4-biphenylylacetic acid | l α-propionylthio-4'-chloro-4-biphenylylacetic acid | 22 |
| α-sulfino-4'-nitro-4-biphenylylacetic acid | d α-sulfino-4'-nitro-4-biphenylylacetic acid | 23 |
| α-sulfino-4'-nitro-4-biphenylylacetic acid | l α-sulfino-4'-nitro-4-biphenylylacetic acid | 22 |
| methyl α-acetylthio-2'-chloro-4-biphenylylacetic acid | d methyl α-acetylthio-2'-chloro-4-biphenylylacetic acid | 23 |
| methyl α-acetylthio-2'-chloro-4-biphenylylacetic acid | l methyl α-acetylthio-2'-chloro-4-biphenylylacetic acid | 22 |
| benzyl α-acetylthio-2'-chloro-4-biphenylylacetic acid | d benzyl α-acetylthio-2'-chloro-4-biphenylylacetic acid | 23 |
| benzyl α-acetylthio-2'-chloro-4-biphenylylacetic acid | l benzyl α-acetylthio-2'-chloro-4-biphenylylacetic acid | 22 |
| N-methyl α-acetylthio-2'-chloro-4-biphenylylacetic acid | d N-methyl α-acetylthio-2'-chloro-4-biphenylylacetic acid | 23 |
| N-methyl α-acetylthio-2'-chloro-4-biphenylylacetic acid | l N-methyl α-acetylthio-2'-chloro-4-biphenylylacetic acid | 22 |
| N,N-diethyl α-acetylthio-2'-chloro-4-biphenylylacetic acid | d N,N-diethyl α-acetylthio-2'-chloro-4-biphenylylacetic acid | 23 |
| N,N-diethyl α-acetylthio-2'-chloro-4-biphenylylacetic acid | l N,N-diethyl α-acetylthio-2'-chloro-4-biphenylylacetic acid | 22 |
| N,N-pentamethylene α-acetylthio-2'-chloro-4-biphenylylacetic acid | d N,N-pentamethylene α-acetylthio-2'-chloro-4-biphenylylacetic acid | 23 |
| N,N-pentamethylene α-acetylthio-2'-chloro-4- | l N,N-pentamethylene αacetylthio-2'-chloro-4- | |

| STARTING MATERIAL | PRODUCT | EXAMPLE |
|---|---|---|
| biphenylylacetic acid | biphenylylacetic acid | 22 |
| N,N-oxydiethylene α-acetylthio-2'-chloro-4-biphenylyl-acetic acid | d N,N-oxydiethylene α-acetylthio-2'-chloro-4-biphenylyl acetic acid | 23 |
| N,N-oxydiethylene α-acetylthio-2'-chloro-4-biphenylyl-acetic acid | l N,N-oxydiethylene α-acetylthio-2'-chloro-4-biphenylyl acetic acid | 22 |
| α-acetylthio-2'-chloro-4-biphenylylacetic acid, sodium salt | d α-acetylthio-2'-chloro-4-biphenylylacetic acid, sodium salt | 23 |
| α-acetylthio-2'-chloro-4-biphenylylacetic acid, sodium salt | l α-acetylthio-2'-chloro-4-biphenylylacetic acid, sodium salt | 22 |
| α-acetylthio-2'-chloro-4-biphenylylacetic acid, diethylammonium salt | d α-acetylthio-2'-chloro-4-biphenylylacetic acid, diethylammonium salt | 23 |
| α-acetylthio-2'-chloro-4-biphenylylacetic acid, diethylammonium salt | l α-acetylthio-2'-chloro-4-biphenylylacetic acid, diethylammonium salt | 22 |
| α-acetylthio-2'-chloro-4-biphenylylacetic acid, piperazinium salt | d α-acetylthio-2'-chloro-4-biphenylylacetic acid, piperazinium salt | 23 |
| α-acetylthio-2'-chloro-4-biphenylylacetic acid, piperazinium salt | l α-acetylthio-2'-chloro-4-biphenylylacetic acid, piperazinium salt | 22 |

We claim:
1. A compound of the formula:

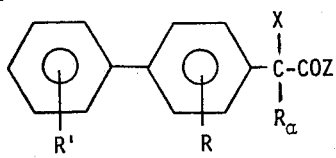

where:
$R_\alpha$ is hydrogen or loweralkyl;
R' and R are hydrogen or not more than one of R or R' at the same time is
halo,
nitro,
amino,
acylamino,
mono- and diloweralkylamino,
mercapto,
acylthio,
loweralkylthio,
loweralkylsulfinyl,
loweralkylsulfonyl,
hydroxy,
loweralkoxy,
acyloxy,
haloloweralkyl,
cyano,
acetyl or
loweralkyl;
X is
thiosulfo;
and
Z is —OH or
—OM where M is an alkali, alkaline earth or aluminum metal or an ammonium salt.

2. A compound according to claim 1 which is dextrorotatory.

3. A compound according to claim 1 which is levorotatory.

4. A compound according to claim 1 of the formula

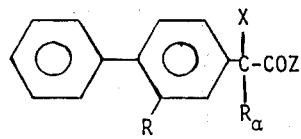

5. A compound according to claim 1 of the formula

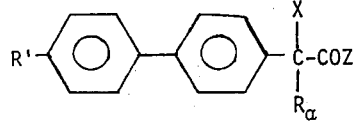

6. A compound according to claim 1 of the formula

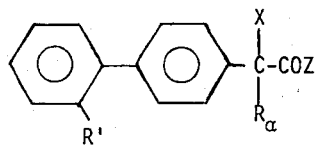

7. A compound according to claim 6 where:
$R_\alpha$ is hydrogen or loweralkyl;
R' is
halo,
nitro,
loweralkylsulfonyl,
haloloweralkyl or
cyano;
X is
thiosulfo, and
Z is —OH or
—OM.

8. A compound of the formula:

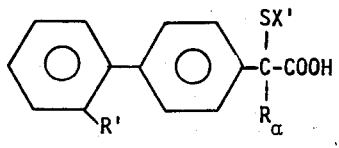

where:
$R_\alpha$ is
hydrogen,
methyl or
ethyl,
R' is
chloro,
bromo,
nitro,
methylsulfonyl,
trifluoromethyl or
cyano;
X' is
sulfo;
and the alkali, alkaline earth, aluminum metal or ammonium salts thereof.

9. A compound according to claim 8 where:
R is methyl.

10. A compound according to claim 8 where:
R is hydrogen.

11. A compound which is α-thiosulfo-2'-chloro-4-biphenylylacetic acid and its alkali, alkaline earth or aluminum metal or ammonium salts.

* * * * *